US005994108A

United States Patent [19]
Gaynor et al.

[11] Patent Number: 5,994,108
[45] Date of Patent: Nov. 30, 1999

[54] MUTANT TAR VIRUS AND TRANSDOMINANT TAT MUTANTS AS PHARMACOLOGICAL AGENTS

[75] Inventors: Richard B. Gaynor, Dallas; David Harrich, Carrollton, both of Tex.

[73] Assignee: Board of Regents, The University of Texas System, Austin, Tex.

[21] Appl. No.: 08/286,874

[22] Filed: Aug. 5, 1994

Related U.S. Application Data

[63] Continuation-in-part of application No. 07/910,867, Jul. 2, 1992, Pat. No. 5,597,895, and application No. 07/788,266, Nov. 5, 1991, Pat. No. 5,350,835.

[51] Int. Cl.$^6$ ............................ C12N 15/48; C12N 15/10; C12N 5/10; C12N 7/01
[52] U.S. Cl. .................................. 435/172.3; 435/235.1; 435/236; 435/369
[58] Field of Search ............................... 435/69.1, 240.2, 435/235.1, 236, 320.1, 172.1, 172.3, 369

[56] References Cited

U.S. PATENT DOCUMENTS 5,350,835   9/1994   Gaynor et al. .......................... 530/358

OTHER PUBLICATIONS

Harrich et al., "Differential Growth Kinetics Are Exhibits by Human Immunodeficiency Virus Type 1 TAR Mutants," *J Virol*, 68(9):5899–5910, Sep. 1994.

Li, Ching et al., "Cloning of a Cellular Factor, Interleukin Binding Factor, That Binds to NFAT–Like Motifs in the Human Immunodeficiency Virus Long Terminal Repeat," *Proc. Natl. Acad. Sci. USA*, 88:7739–7743, 1991, published in USA.

Calnan, Barbara J. et al., "Analysis of Arginine–Rich Peptides from the HIV Tat Protein Reveals Unusual Features of RNA–Protein Recognition," *Genes and Development*, 5:201–210, 1991, published in USA.

Modesti, Nidia et al., "Trans–Dominant Tat Mutants with Alterations in the Basic Domain Inhibit HIV–1 Gene Expression," *The New Biologist*, 3(8):759–768, 1991, published in USA.

Pearson, Lori et al., "A Transdominant Tat Mutant That Inhibits Tat–Induced Gene Expression from the Human Immunodeficiency Virus Long Terminal Repeat," *Proc. Natl. Acad. Sci. USA*, 87:5079–5083, 1990, published in USA.

Brake, David A. et al., "Characterization of Murine Monoclonal Antibodies to the Tat Protein from Human Immunodeficiency Virus Type 1," *Journal of Virology*, 64(2):962–965, 1990, published in USA.

Dayton, Andrew I. et al., "The Trans–Activator Gene of the Human T Cell Lymphotropic Virus Type III Is Required for Replication," *Cell*, 44:941–947, 1986, published in USA.

Feng, Sandy and Holland, Eric C., "HIV–1 Tat Trans–Activation requires the Loop Sequence within Tar," *Nature*, 334:165–167, 1988, published in Great Britain.

Fisher, Amanda G., et al., "The Trans–Activator Gene of HTLV–III Is Essential for Virus Replication," *Nature*, 320:367–371, 1986, published in Great Britain.

Frankel, Alan D. et al., "Tat Protein from Human Immunodeficiency Virus Forms a Metal–Linked Dimer," *Science*, 240:70–73, 1988, published in USA.

Friedman, Alan D. et al., "Expression of a Truncated Viral Trans–Activator Selectively Impedes Lytic Infection by Its Cognate Virus," *Nature*, 335:452–454, 1988, published in Great Britain.

Garcia, Joseph A. et al., "Functional Domains required for Tat–Induced Transcriptional Activation of the HIV–1 Long Terminal Repeat," *The EMBO Journal*, 7(10):3143–3147, 1988, published in Great Britain.

Garcia, Joseph A. et al., "Human Immunodeficiency Virus Type 1 LTR TATA and TAR Region Sequences Required for Transcriptional Regulation," *The EMBO Journal*, 8(3):765–778, 1989, published in Great Britain.

Glenn, Gary M. and Ricciardi, Robert P., "An Adenovirus Type 5 E1A Protein with a Single Amino Acid Substitution Blocks Wild–Type E1A Transactivation," *Molecular and Cellular Biology*, 7(3):1004–1011, 1987, published in USA.

Gorman, Cornelia M. et al., "Recombinant Genomes Which Express Chloramphenicol Acetyltransferase in Mammalian Cells," *Molecular and Cellular Biology*, 2(9):1044–1051, 1982, published in USA.

Harrich, David et al., "TAR Independent Activation of the Human Immunodeficiency Virus in Phorbol Ester Stimulated T Lymphocytes," *The EMBO Journal*, 9:13):4417–4434, 1990, published in Great Britain.

Hauber, Joachim et al., "Mutational Analysis of the Conserved Basic Domain of Human Immunodeficiency Virus Tat Protein," *Journal of Virology*, 63(3):1181–1187, 1989, published in USA.

Jones, Katherine A. et al., "Activation of the AIDS Retrovirus Promoter by the Cellular Transcription Factor, Spl," *Science*, 232:755–759, 1986, published in USA.

(List continued on next page.)

*Primary Examiner*—David Guzo
*Attorney, Agent, or Firm*—Denise L. Mayfield

[57] ABSTRACT

Transdominant HIV tat substitution and truncated gene mutants of 72 amino acid residues or less are disclosed. The mutated genes encode mutant Tat proteins which are capable of inhibiting the expression of the HIV-1 virus in the presence of an equimolar concentration of the wild type Tat protein in vitro. Therapeutic agents which include fused protein forms of the mutant proteins are also disclosed, as well as methods of preparing and using the therapeutic agents in the treatment of HIV infection and HIV-related injections in an animal. Recombinant vectors which express the mutant HIV Tat proteins described are also disclosed, as well as cell lines which product high yields of the mutant HIV. Also provided are cell lines that express enhanced levels of TAR mutant viruses relative to other TAR mutant infected cell lines. Levels of production are enhanced by the use of cell lines that express a transactivator protein, such as adenovirus transactivator EIA and/or EIB protein. Methods of preparing these cell lines, as well as vaccines from virus produced by these cell lines, are also disclosed.

12 Claims, 27 Drawing Sheets

OTHER PUBLICATIONS

Malim, Michael H. et al., "Functional Dissection of the HIV–1 Rev Trans–Activator–Derivation of a Trans–Dominant Repressor of Rev Function," *Cell*, 58:205–214, 1989, published in USA.

Rice, Andrew P. and Carlotti, Franco, "Mutational Analysis of the Conserved Cysteine–Rich Region of the Human Immunodeficiency Virus Type 1 Tat Protein," *Journal of Virology*, 64(4):1864–1868, 1990, published in USA.

Rosen, Craig A. et al., "The Location of Cis–Acting Regulatory Sequences in the Human T Cell Lymphotropic Virus Type III (HTLV–III/LAV) Long Terminal Repeat," *Cell*, 41:813–823, 1985, published in USA.

Ruben, Steven et al., "Structural and Functional Characterization of Human Immunodeficiency Virus Tat Protein," *Journal of Virology*, 63(1):1–8, 1989, published in USA.

Sadaie, M. Reza et al., "Site–Directed Mutagenesis of Two Trans–Regulatory Genes (tat–III, trs) of HIV–1," *Science*, 239:910–913, 1988, published in USA.

Selby, Mark J. et al., "Structure, Sequence, and Position of the Stem–Loop in tar Determine Transcriptional Elongation by tat Through the HIV–1 Long Terminal Repeat," *Genes & Development*, 3:547–558, 1989, published in USA.

Siomi, Haruhiko et al., "Effects of a Highly Basic Region of Human Immunodeficiency Virus Tat Protein on Nucleolar Localization," *Journal of Virology*, 64(4):1803–1807, 1990, published in USA.

Wu, Foon et al., "tat Regulates Binding of the Human Immunodeficiency Virus Trans–Activating Region RNA Loop–Binding Protein TRP–185," *Genes & Development*, 5:2128–2140, 1991, published in USA.

Mann, David A. and Frankel, Alan D., "Endocytosis and Targeting of Exogenous HIV–1 Tat Protein," *The EMBO Journal*, 10(7):1733–1739, 1991, published in Great Britain.

Elroy–Stein, Orna et al., "Cap–Independent Translation of mRNA Conferred by Encephalomyocarditis Virus 5' Sequence Improves the Performance of the Vaccinia Virus/ Bacteriophage T7 Hybrid Expression System," *Proc. Natl. Acad. Sci. USA*, 86:6126–6130, 1989, published in USA.

Templeton, Dennis J., "Nuclear Binding of Purified Retinoblastoma Gene Product Is Determined by Cell Cycle–Regulated Phosphorylation," *Molecular and Cellular Biology*, 12(2):435–443, 1992, published in USA.

Marciniak, Robert A. et al., "HIV–1 Tat Protein Trans–Activates Transcription in Vitro," *Cell*, 63:791–802, 1990, published in USA.

Gaynor, Richard et al., "Specific Binding of a HeLa Cell Nuclear Protein to RNA Sequences in the Human Immunodeficiency Virus Transactivating Region," *Proc. Natl. Acad. Sci. USA*, 86:4858–4862, 1989, published in USA.

Hauber, Joachim et al., "Trans–Activation of Human Immunodeficiency Virus Gene Expression Is Mediated by Nuclear Events," *Proc. Natl. Acad. Sci. USA*, 84:6364–6368, 1987, published in USA.

Selby, Mark J. and Peterlin, B. Matija, "Trans–Activation by HIV–1 Tat via a Heterologous RNA Binding Protein," *Cell*, 62:769–776, 1990, published in USA.

Weeks, Kevin M. et al., "Fragments of the HIV–1 Tat Protein Specifically Bind TAR RNA," *Science*, 249:1281–1285, 1990, published in USA.

Gentz, Reiner et al., "Bioassay for Trans–Activation Using Purified Human Immunodeficiency Virus Tat–Encoded Protein: Trans–Activation Requires mRNA Synthesis," *Proc. Natl. Acad. Sci. USA*, 86:821–824, 1989, published in USA.

Gaynor, R.B. et al., "Repeated B Motifs in the Human Immunodeficiency Virus Type I Long Terminal Repeat Enhancer Region Do Not Exhibit Cooperative Factor Binding," *Proc. Natl. Acad. Sci. USA*, 85:9406–9410, 1988, published in USA.

Berkhout and Jeang, "trans Activation of Human Immunodeficiency Virus Type 1 Is Sequence Specific for Both the Single–Stranded Bulge and Loop of the trans–Acting–Responsive Hairpin: a Quantitative Analysis," *Journal of Virology*, 63(12):5501–5504, 1989.

Berkhout et al., "Tat Trans–Activates the Human Immunodeficiency Virus through a Nascent RNA Target," *Cell*, 59:273–282, 1989.

Dingwall et al., "HIV–1 tat protein stimulates by binding to a U–rich bulge in the stem of the TAR RNA structure," *The EMBO Journal*, 9(12):4145–4153, 1990.

Harrich et al., "Role of SP1–Binding Domains in In Vivo Transcriptional Regulation of the Human Immunodeficiency Virus Type 1 Long Terminal Repeat," *Journal of Virology*, 63(6):2585–2591, 1989.

Hauber and Cullen,"Mutational Analysis of the trans–Activation–Responsive Region of the Human Immunodeficiency Virus Type I Long Terminal Repeat," *Journal of Virology*, 62(3):673–679, 1988.

Jakobovits et al., "A Discrete Element 3' of Human Immunodeficiency Virus 1 (HIV–1) and HIV–2 mRNA Initiation Sites Mediates Transcriptional Activation by an HIV trans Activator," *Molecular and Cellular Biology*, 8(6):2555–2561, 1988.

Kliewer et al., "Multiple Transcriptional Regulatory Domains in the Human Immunodeficiency Virus Type 1 Long Terminal Repeat Are Involved in Basal and E1A/ E1B–Induced Promoter Activity," *Journal of Virology*, 63(11):4616–4625, 1989.

Nabel et al., "Alternative Mechanisms for Activation of Human Immunodeficiency Virus Enhancer in T Cells," *Science*, 239:1299–1302, 1988.

FIGURE 1

SEQ ID NO:2

```
MET Glu Pro Val Asp Pro Asn Leu Glu Pro Trp Lys His Pro Gly Ser Gln Pro Arg Thr Ala
ATG GAG CCA GTA GAT CCT AAT CTA GAG CCC TGG AAG CAT CCA GGA AGT CAG CCT AGG ACT GCT

Cys Asn Asn Cys Tyr Cys Lys Lys Cys Phe His Cys Tyr Ala Cys Phe Thr Arg Lys Gly Leu
TGT AAC AAT TGC TAT TGT AAA AAG TGT TTT CAT TGC TAC GCG TGT TTC ACA AGA AAA GGC TTA
                                                                  A      B      C
                                                            Arg Arg│Gln  Arg Arg  Ala│Pro Gln Asp Ser Gln Thr
Gly Ile Ser Tyr Gly Arg Lys Lys │Arg CGG  AGA│CAG  CGA AGA  GCT│CCT CAG GAC AGT CAG ACT
GGC ATC TCC TAT GGC AGG AAG AAG│AGA       
                                49  50  51  52   53  54   55   56   57   58

His Gln Ala Ser Leu Ser Lys Gln
CAT CAA GCT TCT CTA TCA AAG CAG TAA
```

FIGURE 2A
FIGURE 2B
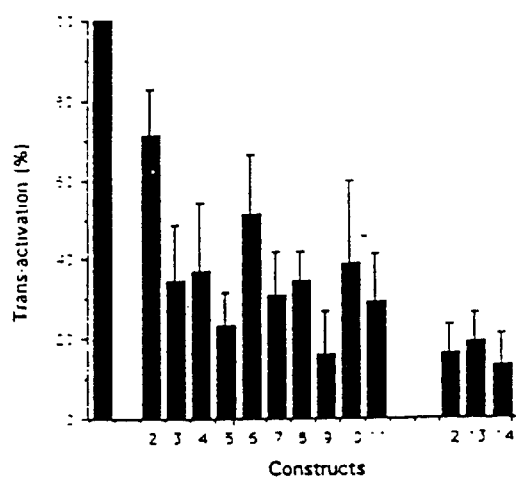
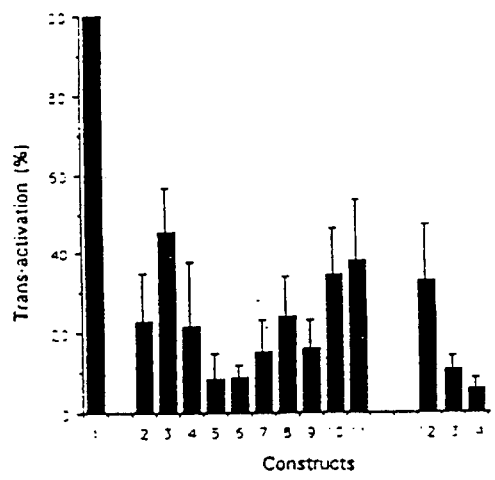

FIGURE 3A
FIGURE 3B
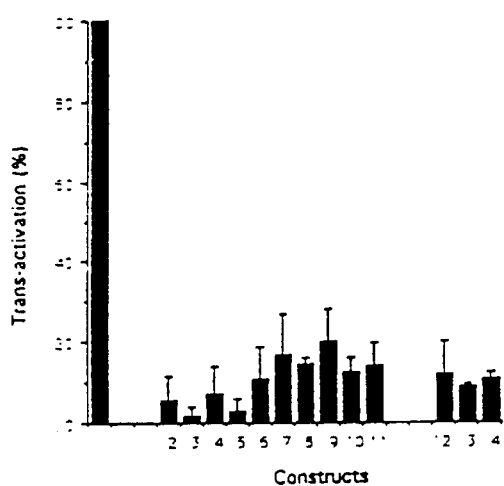
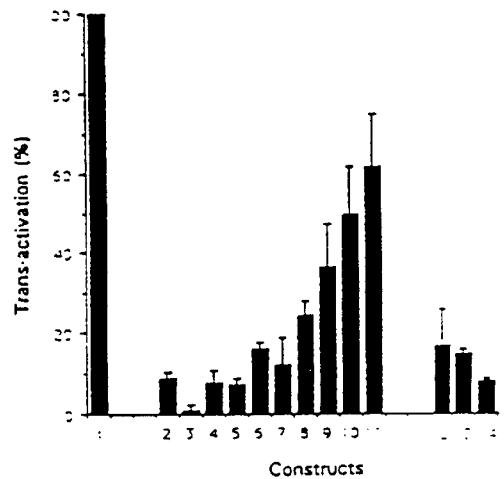

FIGURE 6E
FIGURE 6F
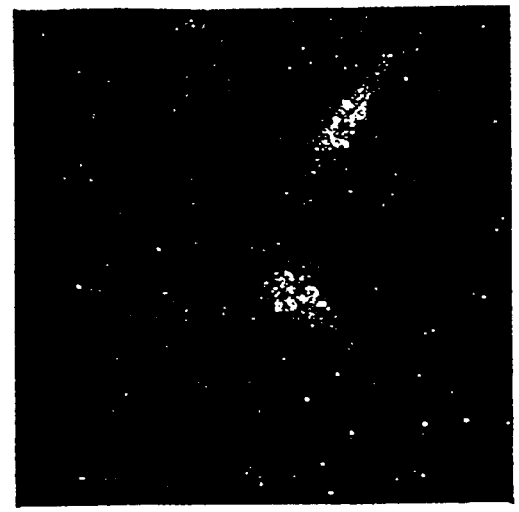
FIGURE 6G
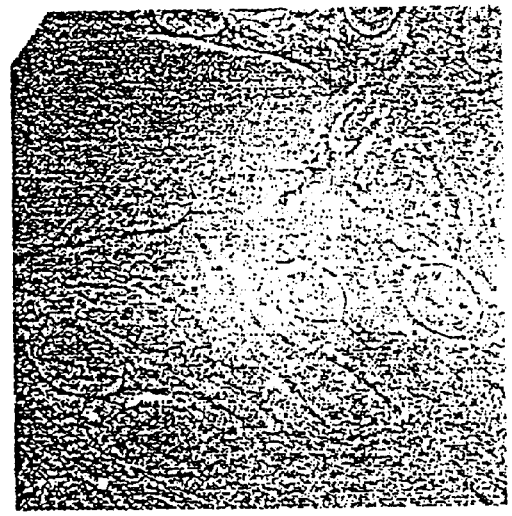

FIGURE 7A

SEQ ID NO:1

```
MET Glu Pro Val Asp Pro Asn Leu Glu Pro Trp Lys His Pro Gly Ser Gln Pro Arg Thr Ala
ATG GAG CCA GTA GAT CCT AAT CTA GAG CCC TGG AAG CAT CCA GGA AGT CAG CCT AGG ACT GCT

Cys Asn Asn Cys Tyr Cys Lys Lys Cys Cys Phe His Cys Tyr Ala Cys Phe Thr Arg Lys Gly Leu
TGT AAC AAT TGC TAT TGT AAA AAG TGT TGC TTT CAT TGC TAC GCG TGT TTC ACA AGA AAA GGC TTA

Gly Ile Ser Tyr Gly Arg Lys Lys Gly Gly Ala Gly Gly Gly Ala Pro Gln Asp Ser Gln Thr
GGC ATC TCC TAT GGC AGG AAG AAG GGG GGA GCC GGC GGA GGA GCT CCT CAG GAC AGT CAG ACT
                  49  50  51  52  53  54  55  56  57  58

His Gln Ala Ser Leu Ser Lys Gln
CAT CAA GCT TCT CTA TCA AAG CAG TAA
```

FIGURE 7B

SEQ ID NO:3

MET Glu Pro Val Asp Pro Asn Leu Glu Pro Trp Lys His Pro Gly Ser Gln Pro Arg Thr Ala
ATG GAG CCA GTA GAT CCT AAT CTA GAG CCC TGG AAG CAT CCA GGA AGT CAG CCT AGG ACT GCT

Cys Asn Asn Cys Tyr Cys Lys Lys Cys Phe His Cys Tyr Ala Cys Phe Thr Arg Lys Gly Leu
TGT AAC AAT TGC TAT TGT AAA AAG TGT TTT CAT TGC TAC GCG TGT TTC ACA AGA AAA GGC TTA

Gly Ile Ser Tyr Gly Arg Lys Lys Arg Arg Ala Gly Gly Gly Ala Pro Gln Asp Ser Gln Thr
GGC ATC TCC TAT GGC AGG AAG AAG CGG AGA GCC GGC GGA GGA GCT CCT CAG GAC AGT CAG ACT 49 50 51 52 53 54 55 56 57 58

His Gln Ala Ser Leu Ser Lys Gln
CAT CAA GCT TCT CTA TCA AAG CAG TAA

FIGURE 7C

SEQ ID NO:5

```
MET Glu Pro Val Asp Pro Asn Leu Glu Pro Trp Lys His Pro Gly Ser Gln Pro Arg Thr Ala
ATG GAG CCA GTA GAT CCT AAT CTA GAG CCC TGG AAG CAT CCA GGA AGT CAG CCT AGG ACT GCT

Cys Asn Asn Cys Tyr Cys Lys Lys Cys Phe His Cys Tyr Ala Cys Phe Thr Arg Lys Gly Leu
TGT AAC AAT TGC TAT TGT AAA AAG TGT TTT CAT TGC TAT GCG TGT TTC ACA AGA AAA GGC TTA

Gly Ile Ser Tyr Gly Arg Lys Lys Arg Arg Gln   Gly Ala Gly Gly Pro   Gln Asp Ser Gln Thr
GGC ATC TCC TAT GGC AGG AAG AAG CGG AGA CAG   GGA GCC GGC GGT CCT   CAG GAC AGT CAG ACT
                49  50  51  52  53  54        55  56  57  58

His Gln Ala Ser Leu Ser Lys Gln
CAT CAA GCT TCT CTA TCA AAG CAG TAA
```

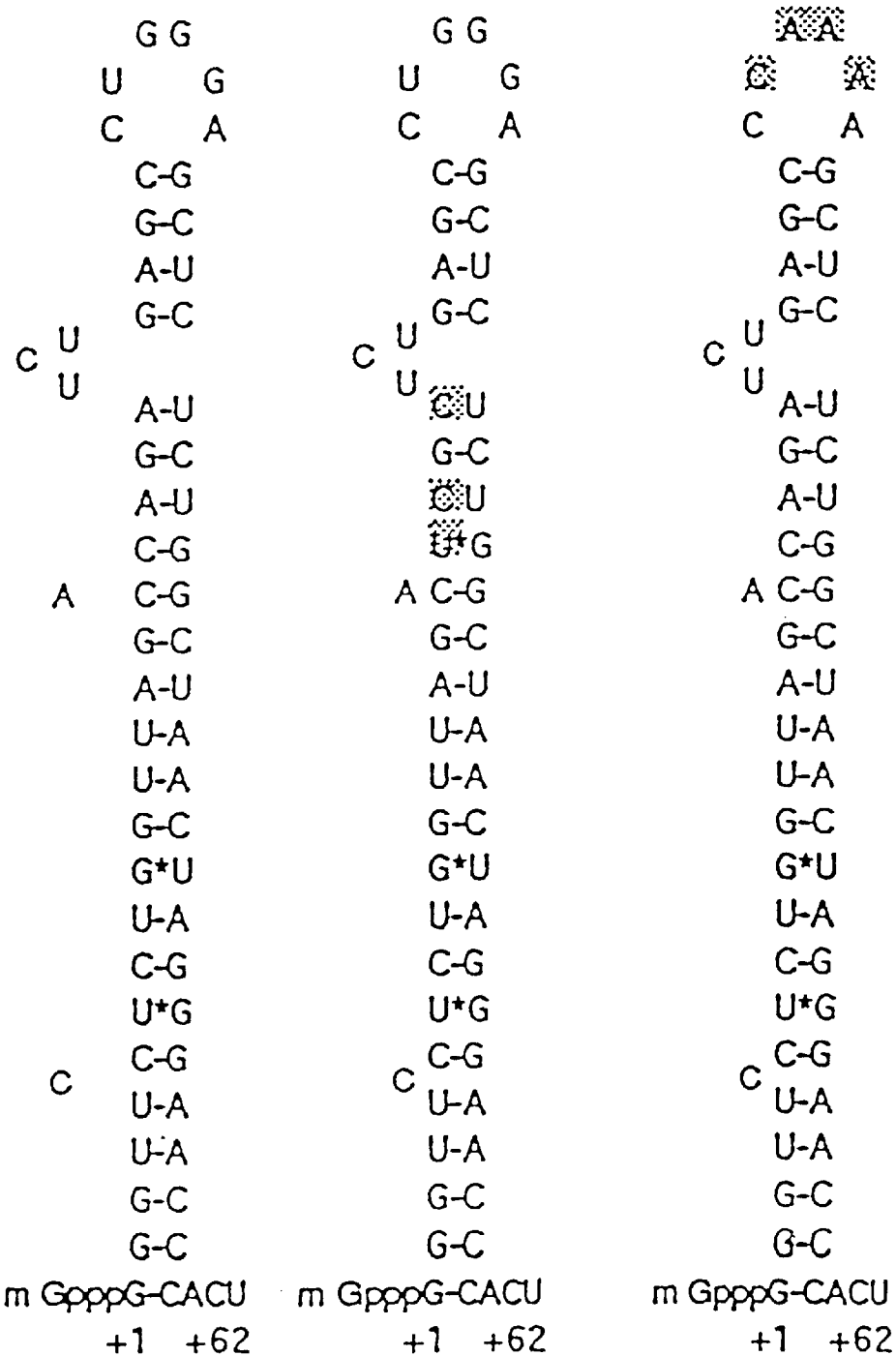

SEQ ID NO: 28

SEQ ID NO: 29

SEQ ID NO: 30

SEQ ID NO: 31

SEQ ID NO: 32

SEQ ID NO: 33

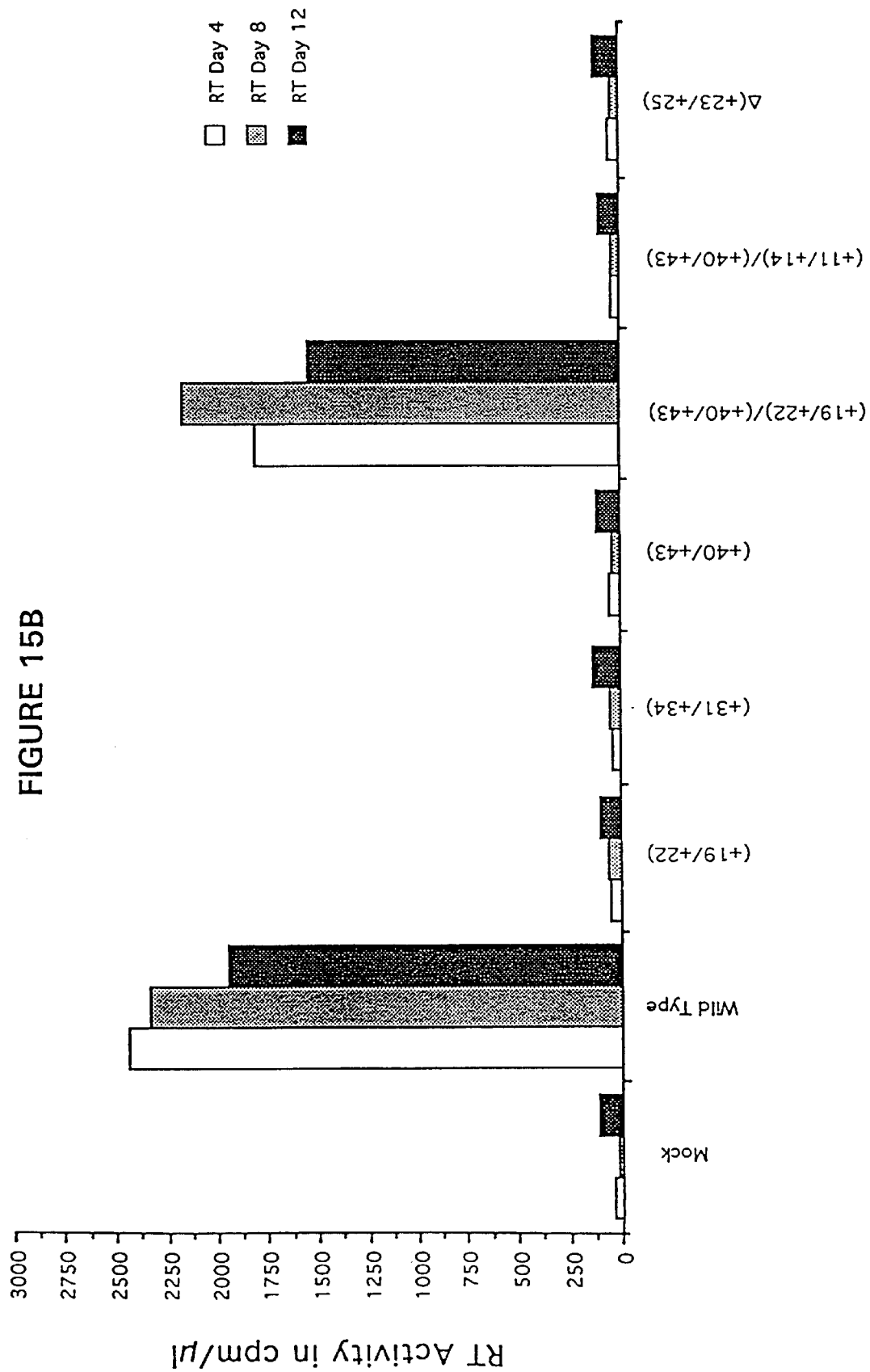

1. mock
2. wild-type
3. (+19/+22)
4. (+31/+34)
5. (+40/+43)
6. (+19/+22/+40/+43)
7. (+11/+14/+40/+43)
8. (+23/+25)

MUTANT TAR VIRUS AND TRANSDOMINANT TAT MUTANTS AS PHARMACOLOGICAL AGENTS

This application is a continuation-in-part of Ser. No. 07/910,867 filed Jul. 2, 1992, now U.S. Pat. No. 5,597,895 and a continuation-in-part of Ser. No. 07/788,266, filed Nov. 5, 1991, now U.S. Pat. No. 5,350,835.

The government has rights in the present invention as research relevant to the development thereof was supported by NIH grant # AI25288.

BACKGROUND OF THE INVENTION

1. Field of the Invention

The present invention relates to the field of viral proteins, particularly those proteins involved in HIV gene regulation and mutants thereof. The gene which encodes the viral factor is also related to the field of the present invention. Recombinant vectors and host cells including a gene of interest, such as the gene for the viral nucleic acid binding factor is also related to the present disclosure. The present invention also relates to the field of methods for regulating the expression of cellular and viral genes, particularly HIV gene expression, and to methods of treatment, and therapeutic agents for treating acquired immunodeficiency disease and other HIV related diseases or symptoms incident an HIV or AIDS infection. The invention further relates to TAR mutants and cell lines infected with TAR mutants, as well as methods for preparing and producing mutant TAR virus.

2. Background of the Related Art

The regulation of HIV-1 gene expression is dependent on multiple cis-acting control elements in the long terminal repeat (Gaynor, R., 1992). Both DNA and RNA elements in the HIV-1 LTR serve as binding sites for cellular factors. In addition, viral regulatory proteins such as Tat and Rev are involved in the activation of gene HIV-1 expression. The mechanisms by which cellular factors interact with Tat and Rev to increase HIV-1 gene expression are not understood.

The human immunodeficiency virus (HIV) is the causative agent of AIDS (Berkhout et al., 1989; Roy et al., 1990b). In common with other retroviruses (Friedman et al., 1988), HIV contains two long terminal repeats (LTRs) and three conserved genes, gag, pol, and env. It also contains a number of critical regulatory genes including tat and rev which, in conjunction with cellular polymerases and transcription factors, are necessary for the activation of viral gene expression (Feng et al., 1988; Gorman et al., 1982; Pearson et al. 1990). Once HIV-1 integrates into the host cell genome, its gene expression is regulated by cellular transcription factors in a manner similar to that of endogenous cellular genes (Friedman et al., 1988). Unlike cellular genes, unique features in the DNA and RNA regulatory regions of the HIV-1 LTR make it a target for the viral transactivator protein, Tat. The activities of several of the cellular transcription factors which bind to the HIV-1 LTR are altered by parameters such as activation or differentiation of lymphocytes or macrophages, the action of lymphokines, and alterations of signal transduction pathways (Garcia et al., 1988, Weeks et al., 1990). Thus, HIV is subject to many of the same regulatory signals that are important in controlling cellular gene expression.

A variety of viral transactivators including the adenovirus E1A, cytomegalovirus immediate early, and the human T-cell leukemia virus tax proteins are able to activate HIV-1 gene expression (Dingwall et al., 1990; Sodroski et al., 1985). These proteins activate HIV-1 through different regulatory elements including the TATA box, USF binding site, and NF-kB sites respectively (Dingwall et al., 1990; Sodroski et al., 1985). In contrast to these viral transactivator proteins whose activity is relatively permissive, activation by the Tat protein is specific for HIV. Disruption of the tat gene prevents viral replication indicating its essential role in the HIV-1 life cycle (Gorman et al., 1982; Pearson et al., 1990). The Tat protein is known to possess at least three functional domains (Sadaie et al., 1988). These include an amino-terminal activation domain, a cysteine-rich domain which may function in dimerization, and a basic domain which is important in nuclear localization and RNA binding (Fisher et al., 1986; Frankel et al., 1988; Garcia et al., 1988; Harrich et al., 1990; Hauber et al., 1987; Sadaie et al., 1988). Despite knowledge of these details, the mechanism of Tat activation remains open to question, and thus an identification of potential interactions between Tat and cellular factors is important for understanding Tat function.

A number of cis-acting regulatory elements in the HIV-1 LTR are critical for basal and Tat-induced gene expression. These include the enhancer, SP1 (Gentz et al.; Modesti et al., 1991), TATA (Sadaie et al., 1988; Selby et al., 1990; Marciniak et al., 1990), and TAR elements (Brake et al., 1990; Malim et al., 1989; Selby et al., 1990; Templeton, 1992). Each of these elements serves as a binding site for cellular transcription factors. Though the SP1 and TATA elements influence the basal level of HIV-1 gene expression, they also play a role in determining the level of activation by the transactivator protein Tat (Modesti et al., 1991). The TAR element which forms a stable stem-loop RNA structure extending from +1 to +60 is critical for Tat activation (Brake et al., 1990; Malim et al., 1989; Rosen et al., 1985; Templeton 1992). A number of studies using fusions of Tat to other known DNA or RNA binding proteins indicate that Tat is able to activate HIV-1 gene expression when bound to either DNA or RNA (Mann et al., 1991; Modesti et al., 1991). Thus it is likely that factors binding to both DNA and RNA regulatory elements influence the degree of Tat activation.

One HIV-1 regulatory element, TAR, is critical for tat activation (Rosen et al., 1985). TAR forms a stable stem loop RNA structure (Lu et al., 1993; Okamoto and Wong-Staal, 1986) that contains three critical elements. These include a three nucleotide bulge between +23 and +25 (Berkhout and Jeang, 1989; Calnan et al., 1991; Dingwall et al., 1990; Roy et al., *Genes & Dev.,* 1990; Roy et al., *J. Virol.,* 1990), a six nucleotide loop between +30 and +35 (Berkhout and Jeang, 1989; Feng and Holland, 1988; Garcia et al., 1989; Roy et al., *Genes & Dev.,* 1990; Roy et al., *J. Virol.,* 1990; Wu et al., 1991), and the upper stem structure between +18 and +43 (Feng and Holland, 1988; Garcia et al., 1989; Hauber and Cullen, 1988; Jakobovits et al., 1988; Roy et al., *J. Virol.,* 1990; Selby et al., 1989). Tat binds directly to the TAR RNA bulge (Calnan et al., 1991; Dingwall et al., 1989; Dingwall et al., 1990; Roy et al., *Genes & Dev.,* 1990; Weeks and Crothers, 1991) while a cellular factor designated TRP-185/TRP-1 binds to the loop sequences (Sheline et al., 1991; Roy et al., *J. Virol.,* 1990) and other proteins have been found to bind to the stem (Gatignol et al., 1991). In addition, TAR DNA serves as the binding site for a variety of proteins (Garcia et al., 1987; Jones et al., 1988; Kato et al., 1991; Wu et al., 1988) which may be involved in the generation of short transcripts from the HIV-1 LTR (Ratnasabapathy et al., 1990; Sheldon et al., 1993). Heterologous constructs containing TAR fused to a variety of different promoters are capable of being activated by tat indicating the critical role of this element (Berkhout et al., 1992; Muesing et al., 1987; Peterlin et al., 1986; Ratnasabapathy et al., 1990; Wright et al., 1986). Thus TAR is a complex regulatory element which is important in modulating tat-mediated gene expression from the HIV-1 LTR.

The function of the TAR element has been studied by transient expression assays of wild-type and mutant HIV-1 LTR templates in both the presence and absence of tat (Berkhout and Jeang, 1989; Feng and Holland, 1988; Garcia et al., 1989; Hauber and Cullen, 1988; Jakobovits et al., 1988; Rosen et al., 1985; Roy et al., *J. Virol.*, 1990; Selby et al., 1989). In addition, transient transfection assays of wild-type and TAR mutant proviral constructs have also been used to demonstrate a critical role for TAR in regulating HIV-1 gene expression (Hauber and Cullen, 1988). However, it has not previously been possible to generate high titer stocks of TAR mutant viruses to study the effects of these mutations on gene expression and growth properties. Viral mutants in other HIV-1 regulatory elements such as NF-κB and SP1 have been constructed and the effects of these mutations on viral growth properties have been analyzed (Leonard et al., 1989; Lu et al., 1989; Parrott et al., 1991; Ross et al., 1991). These studies indicated that viral growth properties were affected by both the specific mutation introduced and the cell type on which viral growth was analyzed.

Mutagenesis has localized a region of TAR RNA between +18 and +44 as an essential element for activation by Tat (Brake et al., 1990; Calnan et al., 1991; Dayton et al., 1986; Glen et al., 1987; Malim et al., 1989; Selby et al., 1990; Elroy-Stein et al., 1989). Several elements in this RNA region including the bulge (+23/+25), the loop (+30/+35), and the stem structure are required for complete Tat-activation (Brake et al., 1990; Dayton et al., 1986; Glen et al., 1987; Malim et al., 1989; Selby et al., 1990; Elroy-Stein et al., 1989). The function of the stem structure is likely to maintain the position of the bulge and loop structures. The bulge region in TAR RNA serves as the binding site for Tat though the loop sequences also influence Tat binding (Fisher et al., 1986; Frankel et al., 1988; Garcia et al., 1988; Hauber et al., 1987). In addition, cellular factors are also capable of binding to the bulge sequences. The interaction between Tat and the TAR RNA bulge is very specific in that a change of one nucleotide at +23 in the bulge is sufficient to disrupt Tat binding (Fisher et al., 1986; Frankel et al., 1988; Garcia et al., 1988; Hauber et al., 1987). The basic domain of Tat is necessary and sufficient for binding to the TAR RNA bulge (Fisher et al., 1986; Frankel et al., 1988; Garcia et al., 1988; Hauber et al., 1987). Extensive mutagenesis of the Tat protein indicates that arginine residues at positions 52 and 53 of Tat are especially critical for interacting with phosphate groups in the TAR RNA bulge (Frankel et al., 1988). The Tat binding to the TAR RNA bulge is thus highly specific and of great affinity.

In contrast to the bulge which binds a viral protein, the loop sequences serve as a binding site for cellular factors that may cooperate with Tat in activating HIV-1 gene expression (Selby et al., 1989; Siomi et al., 1990). Fractionation of HeLa nuclear extract and gel retardation and UV crosslinking using TAR RNA probes indicate that two different cellular proteins p68 and TRP-185 bind to the TAR RNA loop sequences. TRP-185 is a ubiquitously expressed 185 kDa protein whose binding to TAR RNA is regulated by additional cofactor proteins. These cofactors likely function by post-translational modification of TRP-185 i.e., phosphorylation. TRP-185 binding to TAR RNA requires wild-type loop sequences and an intact bulge structure. The binding of TRP-185 to TAR RNA, unlike that of Tat, is not markedly influenced by the primary sequences of the bulge region.

Both Tat and TRP-185 activate HIV-1 LTR gene expression in in vitro transcription assays, but whether these proteins directly interact is not known. These results indicate that Tat activation via the TAR element may require interactions between Tat and cellular transcription factors.

Activation of the HIV-1 LTR by Tat proteins with an altered basic domain has previously been demonstrated to be strongly dependent on the concentration of transfected DNA (Ruben et al., 1989; Hauber et al., 1989). However, how this finding relates to the overall activation of the HIV-1 LTR remains to be determined.

It is critical to determine how Tat modulates the transcriptional apparatus to increase HIV-1 gene expression. Tat stimulates steady state RNA levels synthesized from the HIV-1 LTR approximately 20 to 50-fold. Nuclear run-on experiments using the HIV-1 LTR indicate that Tat stimulates transcriptional initiation. However another effect of Tat function is seen when nascent RNA is measured at various positions downstream of the HIV-1 LTR initiation site in both the presence and absence of Tat (Jones et al., 1986). Though several studies demonstrate an increased number of RNA molecules synthesized from proximal portions of the HIV-1 LTR (near the initiation site) in the presence of Tat, the predominant effect of Tat appears to be a marked increase in the level of RNA synthesized at promoter distal sites (between 500 to 1000 nucleotides from the initiation site) (Jones et al., 1986). In vitro analysis of Tat transactivation also supports an effect on transcriptional elongation. The ability of Tat to increase the number of elongated transcripts may be one explanation for the decrease in the number of short transcripts which are synthesized from the HIV-1 LTR in the absence of Tat. These short transcripts terminate around +60 in the TAR element and may reflect the products of poorly processive transcription complexes. Thus, Tat may function at multiple steps in the transcriptional pathway to increase both the initiation and elongation of transcripts from the HIV LTR.

Mutations in a number of HIV-1 genes including tat (Pearson et al. (1990)), rev ((Malin et al. (1989)), and gag (Trono et al. (1989)) result in proteins with a dominant negative or transdominant phenotype that interfere with the function of the corresponding wild-type proteins. Recently, a Δtat mutation has been described by the present inventors. The Δtat mutant gene therein encoded a 54 amino acid length HIV protein having truncated basic domain (Pearson et al. (1990)). The "basic domain" of the tat gene includes 9 amino acids and is defined by amino acid residues 49–57 of the first 72 amino acids encoding the Tat protein (Pearson et al. (1990)). Three (3) of the amino acid residues of the basic domain of the HIV Tat protein were eliminated in the Δtat to provide the final protein product, leaving six (6) of the residues of the basic domain unchanged. While the Δtat-encoded protein was found to inhibit Tat activation of the HIV-1 LTR when the vector expressing it was present in a 5- to 30-fold molar excess over a vector expressing the wild-type Tat, the mutations were not found to result in a transdominant phenotype.

Further characterization of the precise mechanisms controlling HIV gene expression in regard to the role of the "basic domain" of the tat gene has not been explored, despite the impact such would have in providing more potent and effective therapeutic agents for treating HIV infections.

Previous data have demonstrated that Tat protein is capable of entering cells in culture when added to the tissue culture media (Rice et al., 1990). Though the mechanism of entry is not understood it appears to be a result of endocytosis. To develop transdominant Tat mutant peptides for potential therapeutic use it would be important to develop transdominant mutants of minimal size. This is due to the fact that the amount of partial products and the yield of peptides decrease significantly as their size is increased. A construct which encoded a peptide capable of providing defective activation of HIV LTR gene expression and an ability to antagonize wild-type Tat function, and which was of sufficiently small size to optimize partial product and peptide yield would enable the production of an entirely new class of therapeutic agents used in the treatment and potential cure of HIV infections.

A number of elements in the HIV-1 LTR are critical for the regulation of gene expression. Previous studies have revealed that the enhancer, SP1, TATA and TAR regions are all critical for both basal and tat-induced gene expression (Gaynor, R., 1992). Mutations in the enhancer, SP1, and TATA elements have been inserted into HIV-1 proviral constructs and their effects on gene expression and viral growth assayed (Harrich et al., 1989; Leonard et al., 1989; Lu et al., 1993; Parrott et al., 1991; Ross et al., 1991). These studies indicated that both the specific regulatory element which was mutated and the cell-type which was infected were determinants of the level of viral gene expression. Mutations of some regulatory elements such as the enhancer have very different effects on viral growth than seen with transient assays. Mutation of NF-κB motifs are very deleterious to HIV-1 gene expression when assayed by transient expression (Nabel et al. 1987), but viruses containing these same mutations exhibit only slight decreases in viral growth properties (Leonard et al. 1989; Ross et al., 1991). Thus it is critical to determine how mutations of different HIV-1 regulatory regions alter gene expression following both transient assays and in the context of virus. Since TAR is critical for tat-activation, studies of viruses containing mutations in this regulatory element are critical for a better understanding of the factors controlling HIV-1 gene expression. It has not been possible, before the present invention, to assay the effects of TAR mutations on viral growth and gene expression because of the inability to generate such proviruses.

SUMMARY OF THE INVENTION

Genetic mutants of the Tat protein, particularly non-truncated mutants with an included carboxy terminus, have been constructed that are able to antagonize the function of the corresponding wild-type protein. These transdominant mutant proteins provide powerful tools in the definition of the mechanisms by which these regulatory proteins activate HIV-1 gene expression and inhibit the infection of animal cells by HIV. Thus, these pharmacologically active agents may be formulated in physiologically acceptable adjuvants suitable for administration to an animal, such as a human, to provide potent anti-HIV therapeutic agents and methods of treatment. These mutant proteins more specifically, according to methods set forth by the present inventors, may be employed as therapeutic agents to inhibit HIV-1 growth.

The inventors' laboratory has successfully constructed a series of transdominant Tat mutant proteins which inhibit wild-type Tat function. These mutants may be introduced into HIV-1 infected cells to inhibit HIV viral gene expression and to effectively antagonize wild-type Tat function.

The scope of the present invention includes:

(1) Tat transdominant mutants which inhibit wild-type Tat function;

(2) the construction of HIV-1 proviruses containing transdominant tat mutants for use as vectors to inhibit HIV-1 gene expression;

(3) the production of wild-type and transdominant Tat mutant proteins in both bacterial and vaccinia expression systems for in vitro and in vivo uses in inhibiting HIV-1 gene expression;

(4) the definition of the interaction which occurs between common cellular proteins with wild-type and transdominant Tat proteins in the determination of cellular targets of Tat action;

(5) the proposition of unique potentially useful compositions and methods for the treatment of HIV and related infections;

(6) the definition of particular TAR mutant constructs and cell lines expressing substantially wild-type levels of mutant TAR virus; and (7) methods for enhanced production of mutant TAR virus through construction of cell lines that express both a transactivator protein and that are infected with a mutant TAR virus.

With the work disclosed herein regarding the Tat mutant protein, the present inventors demonstrate that cell lines in the presence of the mutant Tat protein are protected against HIV infection. It is therefore proposed that cell lines that stably express the specific transdominant mutant Tat protein can be made "immune" to subsequent viral, particularly HIV-1, infection. Transdominant mutant genes may thus be used to provide a method for "intracellular immunization" as a means of preventing viral infection.

The present invention provides potent transdominant Tat mutants and characterizes the mechanism by which these mutants inhibit tat gene activation of the HIV-1 LTR.

The inventors' previous mutagenesis of the tat gene has provided for the identification of a truncated tat mutant, wherein the carboxy terminus was deleted, known as Δtat, which inhibited wild-type tat gene activation of the HIV-1 LTR in transfection assays only when present at a 5 to 20-fold molar excess over wild-type tat (*Proc. Natl. Acad. Sci.*, 87:5079–5083 (1991)). The transdominant phenotype of this mutant, which resulted from a truncation in the basic domain of Tat at amino acid 54, was eliminated by second site mutations in either the amino-terminus or cysteine region.

The present work of the inventors provides for the construction of transdominant substitution Tat mutants which have the surprising and unexpected effect of inhibiting wild-type tat gene function at equimolar concentrations, and thereby are significantly more potent than the truncated Δtat mutant. Such transdominant mutants were constructed by substituting neutral amino acids at specific amino acid residues, preferably the substitution of more than two positively changed amino acids, in the basic domain of Tat. The substitution Tat mutants are shown to inhibit tat gene expression to a much greater degree and at low (equimolar) concentrations in the presence of wild-type Tat. For example, the substitution mutants of the present invention inhibit tat gene expression at an equimolar or 3-fold excess over wild-type in vitro, while the truncated Δtat mutant inhibits wild-type expression only when present at a 10- to 20-fold excess, relative to wild-type, in vitro.

Most specifically, the present invention provides for a transdominant mutant HIV Tat protein which is capable of inhibiting HIV gene expression comprising a protein encoded by a particularly substituted mutant tat gene having a substituted basic domain. Preferred forms of these mutant Tat proteins are encoded by a non-truncated amino acid sequence. Examples of the specific nucleotide and protein sequences of substituted mutant tat genes encoding the mutant Tat protein of the invention are provided at FIGS. 7A–7C, that depict a tat mutant A (tat 52/57) (SEQ ID NO: 1; nucleotide, protein) a tat mutant B (tat 54/57) (SEQ ID NO: 3; nucleotide, protein) and a tat mutant C (tat 55/58) (SEQ ID NO: 5; nucleotide, protein).

The transdominant mutant HIV Tat proteins of the present invention may be further defined as proteins encoded by a substituted mutant tat gene having an amino sequence with an overall neutral or positive charge. In order to provide a protein with an overall neutral or positive charge, the amino acid sequence encoding the mutant Tat protein will include an amino acid substitution of a glycine and/or alanine amino acid at the basic domain region of the protein. The transdominant mutant HIV Tat protein may also take the form of a fusion protein. Because the particular mutant Tat proteins are themselves shown to be significantly more potent than other mutant Tat proteins in the presence of wild-type Tat, fusion proteins that include the claimed mutant Tat protein will provide a more potent inhibitory agent against HIV infection. Preservation of the carboxy terminus of the Tat protein, a structural domain recognized by those of skill in the art as important in maintaining the activity of Tat protein, further suggest an enhanced inhibitory activity, as well as enhanced stability of these fusion proteins as compared to fusion protein constructs that include carboxy terminus truncated forms of a mutant Tat protein.

Particular examples of the transdominant mutant HIV Tat protein include those proteins which are encoded by a tat 52/57 mutant (having a nucleotide sequence depicted in SEQ ID NO: 1), a tat 54/57 mutant (having a nucleotide sequence depicted in SEQ ID NO: 3) or a tat 55/58 mutant sequence (having a nucleotide sequence depicted in SEQ ID NO: 5). The designation "tat" is employed to define the tat gene which includes the nucleotide sequence of each of the mutants, while the designation "Tat" is used to designate the amino acid sequence of the mutant protein. Where the tat mutant is tat 52/57, the sequence of the mutant gene may be further defined as encoding the amino acid sequence Gly-Gly-Ala-Gly-Gly-Gly (SEQ ID NO: 4) at amino acid positions 52–57 in the mutant Tat protein. Where the particular tat mutant is the herein described tat 54/57 mutant, the nucleotide sequence encoding said mutant protein may be further defined as encoding an amino acid sequence Ala-Gly-Gly-Gly (SEQ ID NO: 6) at amino acids 54–57 of the mutant protein. Where the transdominant mutant HIV Tat protein is encoded by the tat 55/58 mutant, the tat mutant gene is further described as included a nucleotide sequence which encodes an amino acid sequence Gly-Ala-Gly-Gly (SEQ ID NO: 7) at amino acids 55–58 of the mutant Tat protein.

However, substitutions of any of the amino acids between amino acids 52 and 58 which disrupt the basic charge of the protein may provide a transdominant tat mutant having the capability of inhibiting HIV gene expression in the presence of an equimolar concentration of a wild type Tat protein.

The tat 52/57 mutant, tat 54/57 mutant and tat 55/58 mutant encode HIV Tat proteins which include 72 or less amino acids. These 3 particular mutant tat gene constructs are also referred to throughout the present specification as mutant A, mutant B, and mutant C, respectively.

The referenced mutant HIV Tat constructs are shown by the present inventors to be capable of inhibiting HIV gene expression in the presence of an equimolar concentration of a wild-type Tat protein in vitro. Slight variations of these mutant protein constructs are also expected to provide the same inhibition of HIV gene expression at equimolar concentrations, and are therefore considered to be within the spirit and scope of the present invention.

More generally speaking, the transdominant mutant HIV Tat protein(s) of the present invention may be described as being encoded by a transdominant mutant tat gene which includes four or six amino acid codon substitutions within the basic domain of the Tat protein. The basic domain of the tat gene is defined as encoding a mutant protein having a mutated amino acid sequence within the sequence which encodes amino acids 49–57 of the first 72 amino acids of the native Tat protein (see FIG. 1). It is at this basic domain where specific substitutions of amino acids having a neutral or negative charge are inserted to provide the potent, HIV Tat protein-inhibiting agents of the present invention.

In still another aspect of the present invention, specific truncated mutant HIV Tat proteins are provided which are also demonstrated to be capable of inhibiting HIV gene expression in the presence of an equimolar concentration of a wild type Tat protein in vitro. These particular truncated HIV Tat mutants may be further described as consisting essentially of less than the first 54 amino acids of the native Tat protein, or as consisting essentially of between 55 and 72 of the first 72 amino acids of the native Tat protein. In a most preferred embodiment, the transdominant mutant HIV Tat protein is defined as consisting essentially of 52 amino acids, wherein the 52 amino acids are the first 52 amino acids of the native Tat protein (see FIG. 1). Another most preferred embodiment of the truncated HIV mutant Tat proteins of the invention may be described as consisting essentially of 56 amino acids, again where the 56 amino acids consist essentially of the first 56 amino acids of the native Tat protein.

The particular transdominant mutant HIV Tat proteins may also within the scope of the present invention constitute proteins which are encoded by either or both a truncated or substituted basic domain tat gene mutant. For example, a truncated mutant of 57 amino acids in length may be prepared wherein the particular nucleotide substitutions defined herein for mutant tat B are included within the nucleotide sequence encoding a mutant Tat protein having a length of 57 amino acids. Similarly, a truncated and substituted Tat mutant of 57 amino acids may be prepared wherein the particular basic domain nucleotide substitution described for tat mutant A (52/57) is included within the nucleotide sequence. Ultimately, a truncated and substituted mutant Tat protein may be constructed which is encoded by a sequence of 58 amino acids, wherein a particular nucleotide substitution as defined for tat mutant C 55/58, is included within the nucleotide sequence encoding the mutant protein. Other permutations of the specific embodiments may also be envisioned, and would be expected to inhibit wild-type Tat function at equimolar concentrations in vitro, as well as in vivo.

The transdominant mutant HIV Tat proteins of the present invention may be even further described as constituting a substituted transdominant mutant tat gene as included within an expression vector. By way of example, such an expression vector may constitute any expression vector which contains an SV40 or cytomegalovirus promoter. For example, such an expression vector may be pDEX.

The mechanism of transdominant inhibition of wild-type Tat function has also been clarified in the present disclosure. Contrary to results reported in a previous work (*Proc. Natl. Acad. Sci.,* 87:5079–5083 (1991), it has been found that particular transdominant Tat mutants do not inhibit the ability of wild-type Tat to localize to the nucleus, indicating that it did not alter nuclear localization. Furthermore the particular transdominant Tat mutant 52/57 of the present invention was found to be able to inhibit the ability of R17-Tat fusions to activate gene expression from HIV-1 constructs containing R17 binding sites in place of TAR, thus indicating that intact TAR RNA is not required for inhibition. Attempts to demonstrate dimer formation between Tat and the transdominant mutant have proven unsuccessful. Thus, the most likely mechanism of transdominant Tat inhibition is the interaction with a cellular intermediate required for wild-type Tat function.

Though studies on the positive effects of Tat on HIV-1 gene expression have been useful in determining its function, studies concerning the inhibition of Tat function will be as, if not more, important in not only determining the effects of Tat on HIV gene expression, but in also formulating compounds and therapeutic agents for effectively controlling HIV-1 gene expression in vivo.

Pharmacologically active agents of the mutant Tat protein and tat sequence and methods of using them are shown to protect animal cells against HIV infection. Thus, these preparations are expected to further constitute therapeutic agents for treating HIV and related diseases as provided in forms suitable for administration to a human. By way of example, such infections include AIDS and ARC.

Most specifically, a therapeutic agent for the treatment of an HIV infection comprising a transdominant mutant HIV Tat protein capable of inhibiting HIV gene expression in the presence of an equimolar concentration of a wild type Tat protein in vitro is provided. As a therapeutic agent, the transdominant mutant HIV Tat protein is most preferably included within a pharmaceutically acceptable adjuvant. The particular mutant HIV Tat proteins of the therapeutic agents to be used in the treatment of HIV infection may be defined as a Tat protein comprising a non-truncated sequence of 72 amino acids or less. These 72 amino acids in preferred embodiments include at least one of the following amino acid sequences within the basic domain region of the protein: Gly-Gly-Ala-Gly-Gly-Gly (SEQ ID NO: 4), Ala-Gly-Gly-Gly (SEQ ID NO: 6), or Gly-Ala-Gly-Gly (SEQ ID NO: 7). Among these, the most common preferred amino acid sequence substitution to be included within the particular mutant Tat protein is the sequence Gly-Gly-Ala-Gly-Gly-Gly (SEQ ID NO: 4). However, other amino acid substitutions may also be useful to create transdominant Tat proteins of the present invention.

Examples of the substituted mutant tat gene which encode the particular mutant Tat protein to be included within the herein described therapeutic agents may be further described as a tat 52/57, a tat 54/57 or a tat 55/58 gene mutant. The most preferred of these mutant tat genes which encode the mutant Tat proteins to be used in preparing the described therapeutic agent is the tat 52/57 gene mutant.

The therapeutic agents of the present invention may be further defined as comprising a fused bacterial-viral protein, a cellular ligand-viral protein or a viral epitope CD viral protein. These fusion proteins may be generally defined as bacterial or cellular fusions with the viral protein. More specifically, the tat protein may be fused to histidine residues (from 4 to 8) to aid in the purification of the transdominant tat protein from bacteria using nickel chromatograph (Gentz et al.). In addition, fusion of the transdominant Tat protein to a variety of ligands, such as IL-2 CD product in bacteria, can be considered to specifically target the fusion protein. The pharmaceutically acceptable adjuvant to be included with the transdominant mutant HIV Tat protein may comprise any adjuvant which is suitable for use in an animal, most particularly a human. By way of example, delivery may be in normal saline, albumin, or liposomes for intravenous administration.

The therapeutic agents of the present invention include a transdominant mutant HIV Tat protein which may be further defined as either a substituted transdominant mutant HIV Tat protein or a truncated transdominant mutant HIV Tat protein. In addition, it is contemplated that combinations of the herein described truncated transdominant mutant HIV Tat proteins and substituted transdominant mutant HIV Tat proteins may constitute still another embodiment of the present invention. The therapeutic agents of the present invention may also include substituted forms of the truncated transdominant Tat mutant proteins described herein. For example, a truncated mutant having 57 amino acids may include the particular amino acid sequence substitutions between amino acid residues 54–57, as described herein for Tat mutant B (54/57) or the substitutions between amino acids 52 to –57 as described for Tat mutant A (tat 52/57). Truncated forms of the mutant proteins in most preferred embodiments are not truncated at the carboxy terminus of the amino acid sequence of the Tat protein.

Turning now to a more specific description of the particular truncated transdominant Tat mutants of the present invention, therapeutic agents which include a transdominant Tat protein of 54 amino acids or less, referring to the first 54 amino acids of the Tat protein, may be employed as the therapeutic agent of choice, together in a pharmaceutically acceptable adjuvant. Particularly preferred truncated Tat mutant proteins which include less than 54 amino acids may be further defined as consisting essentially of 49, 50, 51, 52 or 53 amino acids. Therefore, the particular transdominant mutant tat gene would most preferably include sufficient amino acid codons directed to encoding these particular length proteins. Of the aforedescribed truncated transdominant mutant Tat proteins, one of the most preferred is a 50 amino acid length transdominant mutant Tat protein encoded by the corresponding appropriate transdominant mutant tat gene.

The therapeutic agent of the invention is to be formulated so as to be suitable for administration to an animal. By way of example, where the therapeutic agent constitutes the mutant Tat protein, the protein should be formulated so as to be suitable for administration by an intravenous route. Where the therapeutic agent constitutes the transdominant tat gene, it is contemplated that the therapeutic agent will take the form of a retroviral vector to include at least one of the mutant tat genes described herein, or an HIV vector which includes at least one of the mutant tat genes described herein.

Most preferably, the therapeutic agent as described as including either the mutant Tat protein or mutant tat gene will be formulated so as to be suitable for administration to a human.

In still another embodiment of the therapeutic agent, a mutant Tat truncated protein consisting essentially of 55, 56, 57 or 58 amino acids is provided. Such truncated Tat proteins are encoded by a corresponding truncated transdominant mutant tat gene. Again, the mutant protein is not truncated to exclude the carboxy terminus. The mutant Tat protein is formulated together in a pharmaceutically acceptable adjuvant. Of the described truncated mutant Tat proteins, a mutant Tat protein consisting essentially of 56 amino acids constitutes a preferred embodiment of the protein, and is encoded by a corresponding transdominant mutant tat gene.

In still another aspect of the present invention, a recombinant vector comprising a DNA sequence encoding the mutant Tat proteins herein described is provided. The various HIV vectors may also be employed in a method for producing the mutant Tat proteins. For example, the HIV vectors may be used to infect 293 cells which may in turn be cultured and the killed infected cells used as a source of vaccine. In this manner, both the method of delivery of the transdominant mutant, and the ability to produce the vector are unique. The DNA sequence may encode either the transdominant Tat substitution mutant proteins or the transdominant Tat truncated mutant proteins, or a combination thereof. In a most preferred embodiment, the recombinant vector comprises a nucleotide sequence of SEQ ID NO: 1, SEQ ID NO: 3, or SEQ ID NO: 5. The recombinant vector is to be constructed so as to be capable of replication within a host.

Retroviral vectors may also be used as a recombinant vector. In one aspect of the invention, the retroviral vectors are those which do not replicate. The retroviral vectors, in accordance with the present invention, will be used to produce stable cell lines which contain the transdominant tat gene mutant A, B or C nucleotide sequence. Specifically, the retroviral vector preferably is to include a nucleotide sequence as defined for SEQ ID NO: 1, SEQ ID NO: 3 or SEQ ID NO: 5. By way of example, human bone marrow cells can be infected with the aforedescribed retroviral vectors. These infected cells would thereby become resistant to HIV-1 gene expression.

One particular example of the HIV vector which the present inventors have constructed which delivered the transdominant tat gene mutant to cells was prepared by a unique method involving a pBR322 plasmid vector. A drug resistance gene, such as for puromycin or G418 resistance, is most preferably introduced into the HIV genome. These drug resistance genes provide protection against puromycin and G418. These resistance genes are most preferably inserted into the HIV genome at the nef open reading frame.

The above-described retroviral vectors, which by way of example include the pBRHIV-Δ NEF, pBRHIV-puro, and pBRHIV-neo vectors detailed herein in the examples, may then be used to infect permanent cell lines. By way of example, the present inventors have grown these HIV vector constructs on a cell line known as 293. 293 cells are CD4⁻ human embryonic kidney cells that express E1a and E1b proteins from adenovirus. Prior difficulties associated with this cell line of short lived low mutated viral production upon infection, and rapid and elimination from cell pools, were overcome using the inventors techniques of selecting for a purified population of cells which produce the herein described recombinant HIV. The infected cell lines of the present invention provide for the production of the mutant HIV virus, most particularly HIV virus which produce the mutant Tat protein, in large quantities. This technique is particularly novel in light of the above-described difficulties described in the art because it allows for both the production of mutant HIV virus in large quantities. Such may potentially be used, in killed form, as a vaccine. In addition, both the method of delivery of the transdominant mutant, and the technique used to produce the vector are unique.

In still another aspect of the present invention, a recombinant host bearing the recombinant vector described above is provided. The recombinant host will be prepared so as to be capable of expressing the mutant Tat protein of the present invention which is capable of inhibiting HIV gene expression. The transdominant mutant HIV Tat protein is again encoded by a substituted mutant tat gene which may be selected from those presented at FIG. 7. The recombinant host of the present invention will also be capable of expressing at least one of the mutant Tat proteins described herein. By way of example, the recombinant host may be further defined as a *Saccharomyces cerevisiae, E. coli* Baculovirus or a Vaccinia virus host.

The present invention also provides a method of inhibiting HIV infection of an animal cell comprised treating cells with a pharmacologically active amount of the mutant Tat protein described herein. By way of example, such cells are human cells.

In still another aspect of the present invention, a method of inhibiting HIV replication in an animal is provided. The method comprises treating the animal with a therapeutically effective amount of those therapeutic agents described herein. By way of example, such therapeutic agents include a transdominant Tat mutant protein formulated together with a pharmaceutically acceptable adjuvant. Again, the transdominant Tat mutant protein may constitute either truncated or substituted mutant Tat proteins, and, by way of example, may be those particular Tat mutant proteins encoded by the substituted tat mutant genes A (tat 52/57), B (tat 54/57) or C (tat 55/58).

In addition, the transdominant Tat mutant proteins may comprise those truncated mutants described herein, which, by way of example, include those proteins having less than 54 amino acids, most preferably between 49 and 53 amino acids, or having between 55 and 58 amino acids. Again, the reference number of amino acids in the protein, in regard to the truncated transdominant Tat mutant proteins refers to the first 58 amino acids of the native Tat protein. (See FIG. 1). Most preferably, the therapeutic agent should be formulated so as to be suitable for administration to an animal intravenously. However intramuscular administration may be possible. It is contemplated that the therapeutically effective amount of the Tat mutant protein will vary depending upon the particular transdominant Tat mutant protein selected.

In a most preferred embodiment, the therapeutic agent is to be administered intravenously in the case of purified transdominant Tat proteins and also in the case of retroviral vectors or recombinant HIV vectors containing the transdominant tat gene mutant. In the case of these later viral vectors, it may be desirable to harvest patient cells, infect them in tissue culture and then infuse those cells into the patient. Such may provide a method of immunizing the patient to HIV. Most preferably, the methods and therapeutic agents employed in the present invention will be formulated so as to be suitable for the treatment of a human.

The inventors' laboratory has been successful in constructing transdominant Tat mutants which antagonize the activity of wild type Tat. While transdominant mutants of other viral transactivator proteins, including the adenovirus E1A protein, the herpesvirus VP16 protein (Rosen et al., 1985), and the HTLV tax proteins have been constructed, never before have the specific transdominant mutants of the Tat protein been described. Transdominant mutants of viral transactivator proteins must usually be present in a several molar excess over the wild-type protein to suppress gene expression. Moreover, these mutants possess very defective activation phenotypes. In contrast, the presently described mutant Tat proteins are demonstrated to be effective in modulating gene expression at equimolar concentrations, making them superior viral gene suppressing agents to those previously available.

Still another aspect of the present invention provides for specifically modified cell lines that express substantially wild-type levels of HIV-1 TAR mutant virus. Such cell lines are particularly efficacious in the production of usable and commercially important amounts of TAR mutant virus for use, for example, in the preparation of vaccines, most particularly vaccines useful in the treatment of HIV and other diseases related to this virus such as AIDS and ARC. In preferred embodiments, the cell line comprises a mammalian cell line that expresses a transactivator protein as well as a mutant TAR virus. More specifically, the particular TAR mutation may be defined as a mutation occurring in the loop sequence or bulge sequence of the region TAR.

By way of example, mutations of the TAR mutant viruses described may be defined as a mutant +31/+34, this mutant including a mutation in the loop sequence of TAR. In alternative aspects, a mutation of the bulge sequence may be defined as a +23 or ▲ (+23/+25) viral mutant.

While it is expected that any mammalian cell line susceptible to infection with a mutant TAR virus and capable of expressing a transactivator protein may be employed in the practice of the present invention, most preferred mammalian cell lines include the 293 cell line or a cell line engineered to produce a transactivator protein.

Particularly exemplified TAR mutations examined in the examples provided herewith include a +19/+22, +31/+34, +23, +40/+43, (+11/+14)/(+40/+43), ▲+23/+25, ▲(+23/+25)/(+37/+39), and (+19/+22)/(+40/+43).

The enhanced levels of TAR mutant viruses yielded with the herein described methods and cell lines are in part made possible by the unique combination of a concomitant expression of transactivator protein together with the particular TAR mutant within the same cell line. Several transactivator proteins are known to those of skill in the art, including HTLV1 Tax, VPI6 and CMV immediate early protein. Most preferably, the transactivator protein employed in conjunction with the present invention is an adenovirus transactivator protein, such as the E1A protein or the E1A and E1B proteins. In particularly preferred embodiments, the cell expresses both adenovirus transactivation E1A and E1B protein.

Among the various TAR mutant viruses examined, the (+11/+14)/(+40/+43) mutant and (+30/+34) mutant provided the most strikingly enhanced TAR mutant virus production levels relative to others examined.

In still another aspect, the present invention provides a method for producing TAR mutant viruses at substantially wild-type levels in a stably transfected mammalian cell line. In one embodiment, the method comprises transfecting a cell line expressing a transactivator protein with a virus having an HIV-1 TAR mutation to provide a stable TAR mutant infected cell line; and collecting the HIV TAR mutant virus expressed by the stably infected cell line, the improvement in the claimed method therefore lies in the use of a cell line expressing a transactivator protein when transfecting the cell line with a mutant TAR virus of choice. According to this method, the stably infected cell line expresses transactivator protein and elevated levels of TAR virus. As used in the description of the present invention, the term "elevated" is defined as an amount or number of mutant TAR virus that is at least 20% greater than the amount or number of TAR mutant virus produced by transfected cell lines that do not express transactivator protein.

In preferred embodiments of the claimed method, the HIV-1 TAR mutant includes a mutation in the loop sequence or the bulge sequence of TAR by way of example, TAR mutations in the loop sequence include the +31/+34 mutant herein described, while a mutation in the bulge sequence is characteristic of the +23 or Δ(+23/+25) mutant described herein. Again, while it is contemplated that virtually any mammalian cell line that is capable of expressing a transactivator protein and as being infected by a TAR mutant virus while retaining replication competency, a most preferred cell line is the 293 cell line. In addition, the various TAR mutant viruses previously described herein may be used with equal efficacy in conjunction with the claimed method. Most preferably, the transactivator protein is an adenovirus transactivator E1A, or both E1B and E1A proteins.

The following abbreviations are used throughout the description of the present invention:

AIDS—Acquired Immunodeficiency disease
CAT—CHLORAMPHENICOL ACETYLTRANSFERASE
HIV—human immunodeficiency virus
TAR—trans-activation response element
Tat—a viral regulatory protein
LTR—long terminal repeat
RSV—Rous sarcoma virus
tat—a gene which encodes part or mutated forms of the Tat protein

BRIEF DESCRIPTION OF THE DRAWINGS

FIG. 1—Construction of Tat mutants. The first 72 amino acids of Tat are indicated (SEQ ID NO: 2). The position of stop codons introduced at amino acids 49, 50, 51, 52, 53, 54, 55, 56, 57, and 58 are indicated. The boxed regions (solid line, A [tat 52/57]; broken line, B [tat 54/57]; and hatched line, C [tat 57/58]) indicate amino acid substitutions with either glycine or alanine for each of the respective mutants.

FIGS. 2A–2B—Transdominant mutants inhibit trans-activation by Tat. (2A) A vector (0.1 μg) expressing wild-type Tat alone (lane 1) or in the presence of equimolar concentrations of a vector expressing transdominant Tat mutants with truncations at amino acid 49 (lane 2), 50 (lane 3), 51 (lane 4), 52 (lane 5), 53 (lane 6), 54 (lane 7), 55 (lane 8), 56 (lane 9), 57 (lane 10), 58 (lane 11) or containing multiple amino acid substitutions, tat 55/58 (lane 12), tat 54/57 (lane 13), and tat 52/57 (lane 14), were transfected into HeLa cells with 5 μg of HIV-1 LTR CAT plasmid. The final concentration of the RSV constructs in each transfection was kept constant (5 μg) by the incorporation of RSV-β-globin. 100% conversion reflects the CAT activity obtained from the HIV-1 LTR CAT construct in the presence of wild-type Tat. The percentage of trans-activation for each Tat mutant was calculated relative to wild-type Tat. The results show the average of four independent experiments. (2B) The same constructs were transfected as in (A), except that there was a 20-fold molar excess of the vector expressing a transdominant Tat mutant (2 μg) over the vector expressing wild-type Tat (0.1 μg).

FIGS. 3A–3B—Trans-activation by transdominant Tat mutants. (3A) A vector (0.1 μg) expressing Tat alone (lane 1), or a vector (0.1 μg) expressing the transdominant mutants alone, including mutants with truncations at amino acid 49 (lane 2), 50 (lane 3), 51 (lane 4), 52 (lane 5), 53 (lane 6), 54 (lane 7), 55 (lane 8), 56 (lane 9), 57 (lane 10), 58 (lane 11) or with substitutions, tat 55/58 (lane 12), tat 54/57 (lane 13), and tat 52/57 (lane 14), were transfected into HeLa cells with 5 μg of HIV-1 LTR CAT construct. The final concentration of the RSV promoter in each transfection was kept constant (5 μg). 100% conversion reflects the CAT activity obtained from HIV-1 LTR CAT construct in the presence of wild-type Tat. The percentage of trans-activation for each Tat mutant was calculated relative to wild-type Tat. The results shows the average of four independent experiments. (3B) The same constructs were transfected as in (A) only using 2.0 µg of each tat construct.

FIGS. 4A–4B—Transdominant inhibition of TAR mutant constructs. (4A) The wild-type HIV-1 LTR CAT plasmid was transfected into HeLa cells in the absence (lane 1) or presence of a vector expressing Tat (lane 2). In addition, the HIV-1 LTR CAT constructs containing mutations in the TAR loop (+31/+34) (lane 3), stem (+19/+22) (lane 4), stem (+40/+43) (lane 5) stem restoration (+19/+22)/(+40/+43) (lane 6), or a bulge mutation (+23) (lane 7) in the presence of a vector expressing wild-type Tat were transfected into HeLa cells and CAT activity was determined. (4B) The same constructs as in (A) were transfected with a 5-fold excess of the tat 52/57 construct over wild-type tat.

FIGS. 5A–5B—Transdominant inhibition of Tat-R17 fusion proteins. (5A) An HIV-1 construct containing an R17 recognition element in place of the TAR element was cotransfected with an expression vector containing the R17 gene (lane 1), the wild-type tat gene (lane 2), the Tat-R17 fusion protein alone (lane 3), tat 52/57 alone (lane 4) or with either an equimolar (lane 5) or 5-fold molar excess of tat 52/57 alone (lane 6), the Tat-R17 fusion protein with a deletion of amino acids 49/57 in the basic domain (lane 7), or this construct with either an equimolar (lane 8) or 5-fold excess of tat 52/57 (lane 9). (5B) An HIV-1-LTR CAT construct was transfected in the absence (lane 1) or presence of a vector expressing wild-type Tat (lane 2), with the Tat-R17 fusion protein alone (lane 3) or this construct in the presence of an equimolar (lane 4) or 5-fold excess of tat 52/57 (lane 5). DNA concentrations were adjusted as described in Materials and Methods.

FIGS. 6A–6G—Examination of the cellular localization of wild-type Tat and transdominant Tat mutants by indirect immunofluorescence. HeLa cells were fixed and stained as indicated in the description of the preferred embodiments. (6A, 6B) Cells were transfected with a vector expressing wild-type Tat. 6A: Localization of the Tat protein was detected by indirect immunofluorescence staining with the use of a mouse monoclonal antibody to the basic domain of Tat (Brake et al., 1991) as the primary antibody and a rhodamine-conjugated goat antibody to mouse IgG as a second antibody. 6B: Examination of the same field by phase-contrast microscopy. (6C) Cells were transfected with a vector expressing the tat 52/57 protein. Indirect immunofluorescence staining was used to detect the protein, with a rabbit polyclonal antibody to amino acids 1 to 17 of the Tat protein (Pearson et al., 1990) being used as the primary antibody and fluorescein-conjugated goat antibody to rabbit IgG as the secondary antibody. 6D: Examination of the same field by phase-contrast microscopy. (6E–6G) Cells were transfected with a vector expressing wild-type Tat and with a 5-fold molar excess of the vector expressing tat 52/57 protein. Localization of the Tat proteins was detected by double-indirect immunofluorescence staining, with the monoclonal antibody that reacts with wild-type Tat followed by rhodamine-conjugated goat antibody to mouse IgG (6E), and with the polyclonal antibodies that react with both wild-type Tat and tat 52/57, followed by the fluorescein-conjugated goat antibody to rabbit IgG (6F). 6G shows the same field examined by phase contrast microscopy.

FIGS. 7A–7C—(7A) demonstrates the Tat mutant A (tat 52/57), which is also referred to as SEQ ID NO: 1 (nucleic acid, protein sequence). (7B) demonstrates the Tat mutant B (tat 54/57), which is also referred to as SEQ ID NO: 3 (nucleic acid, protein sequence). (7C) demonstrates the Tat mutant C (tat 55/58), which is also referred to as SEQ ID NO: 5 (nucleic acid, protein sequence). The new mutants which may be used in conjunction with the present recombinant HIV vector, will be those described previously (Malim et al. (1989) Cell, 58:205–214).

FIG. 8 shows transdominant inhibition of HIV-1. Twenty nanograms of p24 antigen from wild type HIV-1 was used to infect $10^7$ H9 lymphoid cells containing either vector alone (pBabe), ▲tat (Stop 3 of Pearson et al.) or 52/57 (of the present application, also named TDN 3) constructs. Reverse transcriptase assays were performed every 4 days. The figure legend is as follows:
pBabe mock—control vector without HIV,
pBabe w/HIV-1—control vector with HIV,
TDN 3 Mock—52/57 construct
TDN 3 w/HIV-1—52/57 construct with HIV
Stop 3 Mock—▲tat construct
Stop 3 w/HIV-1—▲tat construct with HIV FIGS. 9A–9I. Schematic of different HIV-1 LTR TAR mutations (SEQ ID NO:25–33). A portion of the HIV-1 LTR TAR element extending from +1 to +62 is shown. The position of mutations in TAR RNA are indicated for (9A) wild-type, (9B)(+19/+22), (9C)(+31/+34), (9D)(+40/+43), (9E)(+19/+22)/(+40/+43), (9F)(+11/+14)/(+40/+43), (9G)(+23), (9H)Δ(+23/+25), (9I)Δ(+23/+25)/(+37/+39).

FIG. 10. Production of HIV-1 TAR mutant viruses. A schematic of the procedure used to generate HIV-1 TAR mutant viruses is shown. An HIV-1 molecular proviral clone (pBRDH2-neo) was linearized with the restriction enzyme Mro I, transfected into 293 cells, and the cells were split into media containing G418. Foci were isolated, expanded, and supernatants were assayed for the production of p24 Ag and RT activity prior to their use for infection of both T-cell lines and PBMCs.

FIGS. 11A–11B—Assays of viral gene expression in 293 cells. The amounts of secreted (11A) p24 Ag (ng/ml) and (11B) reverse transcriptase detected in culture supernatants following an overnight incubation in fresh media are indicated for both uninfected 293 cells and 293 cells containing wild-type HIV-1 or TAR mutant viruses (+19/+22), (+31/−34), (+40/+43), (+19/+22)/(+40/+43), (+11/+14)/(+40/+43), (+23), Δ(+23/+25), and Δ(+23/+25)/(+37/39). The results were obtained for three consecutive days from the same freshly confluent plate of 293 cells and the standard deviation was calculated.

FIGS. 12A–12B—PCR analysis of single cycle infection of Jurkat cells by wild-type and TAR mutant viruses. A two hour infection of $10^6$ Jurkat cells was performed with $2 \times 10^6$ cpm $^{32}$P-RT obtained from 293 cell lines containing either wild-type or TAR mutants. Total DNA was isolated from the infected cells and subjected to 25 cycles of PCR using $^{32}$P labeled specific primers. (12A) The presence of a 139 bp specific amplified band from the HIV-1 LTR was determined for (+19/+22) (lane 1), (+31/+34) (lane 2), (+40/+43) (lane 3), (+19/+22)/(+40/+43) (lane 4), (+11/+14)/(+40/+43) (lane 5), Δ(+23/+25) (lane 6), wild-type virus (lane 7), heat inactivated wild-type virus (lane 8), or uninfected Jurkat cells (lane 9). HIV-1 standards which represent a molecular clone present at 0 copies (lane 10), 10 copies (lane 11), $10^2$ copies (lane 12), $10^3$ copies (lane 13) or $10^4$ (lane 14) are also shown. (12B) The 110 bp specific band produced by PCR with a primer pair corresponding to the human β-globin gene was used as a control for the amount of DNA in part A (lanes 1–9). Also shown is PCR analysis using the β-globin primer pair with either 0 µg (lane 10), 0.02 µg (lane 11), 0.1 µg (lane 12), or 0.5 µg (lane 13) of Jurkat chromosomal DNA.

FIGS. 13A–13C. Assay of p24 antigen following infection of human T-lymphocytes with wild-type and TAR mutant viruses. (13A) H9, (13B) Jurkat or (13C) Jurkat-tat cells were infected with 293 (Δ) mock supernatant or supernatants containing approximately $1 \times 10^6$ $^{32}$P-RT cpm of either (+) wild-type, ▯ (+19/+22), (▲) (+31/+34), (♦) (+40/+43), (○) (+19/+22)/(+40/+43), ■ (+11/+14)/(+40/+43), (◇) (+23), (■)Δ(+23/+25), or (□)Δ(+23/+25)/(+37/+39). The infections were performed three times and assayed for viral expression by an ELISA for secreted p24 Ag present in cell free culture supernatant. Results were similar in each of the three experiments.

FIG. 14. Assay of p24 antigen following infection of human PBMCs with wild-type and TAR mutant viruses. $2\times10^6$ PHA activated PBMCs were infected with $1\times10^6$ $_{32}$P-cpm of RT for two hours at 37° C., the cells washed three times, and maintained in complete media supplemented with 30 U/ml of IL-2. The p24 Ag levels were determined by ELISA every third day for (Δ) mock infection, infection with (+) wild-type HIV-1, or TAR mutant viruses ▫ (+19/+22), (▲) (+31/+34), (◆) (+40/+43), (○) (+19/+22)/(+40/+43), ▪ (+11/+14)/(+40/+43), (◇) (+23) (□)(+23/+25)/(+37/+39), or (■)Δ(+23/+25). The infections were performed three times with similar results.

FIGS. 15A–15B—Assay of p24 antigen levels following isolation of G418 resistant Jurkat cells containing TAR mutant viruses. Approximately $4\times10^5$ G418 resistant Jurkat cells containing different HIV-1 TAR mutants were grown for four days an then assayed preceding each passage for p24 Ag and RT levels. (15A) The amount of secreted p24 Ag in cell free culture supernatants from G418 selected Jurkat cells following passage one (4 days), passage two (8 days), and passage three (12 days) for cells either mock-infected, infected with HIV-1 wild-type, or TAR mutant viruses (+19/+22), (+31/+34), (+40/+43), (+19/+22)/(+40/+43), (+11/+14)/(+40/+43), and Δ(+23/+25) are shown. (15B) The $^{32}$P reverse transcriptase activity in cpm/ml detected in the same culture supernatants are also indicated.

FIGS. 16A–16C—Northern analysis of RNA isolated from G418 resistant Jurkat cells containing TAR mutant viruses. (16A and 16B) Northern blot analysis of 30 μg of total RNA from either uninfected Jurkat cells (lane 1), Jurkat cells infected with either wild-type HIV-1 (lane 2) or TAR mutant viruses (+19/+22) (lane 3), (+31/+34) (lane 4), (+40/+43) (lane 5), (+19/+22)/(+40/+43) (lane 6), (+11/+14)/(+40/+43) (lane 7), and Δ(+23/+25) (lane 8) was performed with an HIV-1 probe extending from 8050 to 8385. (16A) A six day exposure and (16B) an overnight exposure of the Northern blot is shown and the sizes of the 10, 5.1 and 2.8 kB markers are indicated. (16C) The 28S and 18S ribosomal RNA species from an ethidium bromide stained 1% formaldehyde gel used for the Northern blot analysis is also shown.

FIG. 17—Western blot analysis of cell lysates prepared from G418 resistant Jurkat cells containing TAR mutant viruses. Western blot analysis was performed with anti-HIV-1 IgG and detected by ELC. Whole cell lysates were prepared from uninfected Jurkat cells (lane 1), Jurkat cells infected with either HIV-1 wild-type (lane 2), or TAR mutant viruses (+19/+22) (lane 3), (+31/+34) (lane 4), (+40/+43) (lane 5), (+19/+22)/(+40/+43) (lane 6), (+11/+14)/(+40/+43) (lane 7), and Δ(+23/+25) (lane 8).

FIGS. 18A–18B—PCR analysis of proviral load in chromosomal DNA isolated from G418 selected Jurkat cells. (18A) Approximately 0.1 μg of chromosomal DNA isolated from G418 selected Jurkat cells was subjected to 25 cycles of PCR using $^{32}$P labeled specific primers for the HIV-1 R and U5 regions. The presence of the 139 bp specific amplified band is indicated for (+19/+22) (lane 1), (+31/+34) (lane 2), (+40/+43) (lane 3), (+19/+22)/(+40/+43) (lane 4), (+11/+14)/(+40/+43) (lane 5), Δ(+23/+25) (lane 6), wild-type virus (lane 7), or uninfected Jurkat cells (lane 8). A standard is shown representing an HIV-1 molecular clone present at 0 (lane 9), 10 (lane 10), $10^2$ (lane 11), $10^3$ (lane 12), or $10^4$ copies (lane 13). (18B) The 110 bp specific band was generated by PCR using a primer pair to the human β-globin gene to control for DNA content in part A (lanes 1–8).

DETAILED DESCRIPTION OF THE PREFERRED EMBODIMENTS

Figure 4A:
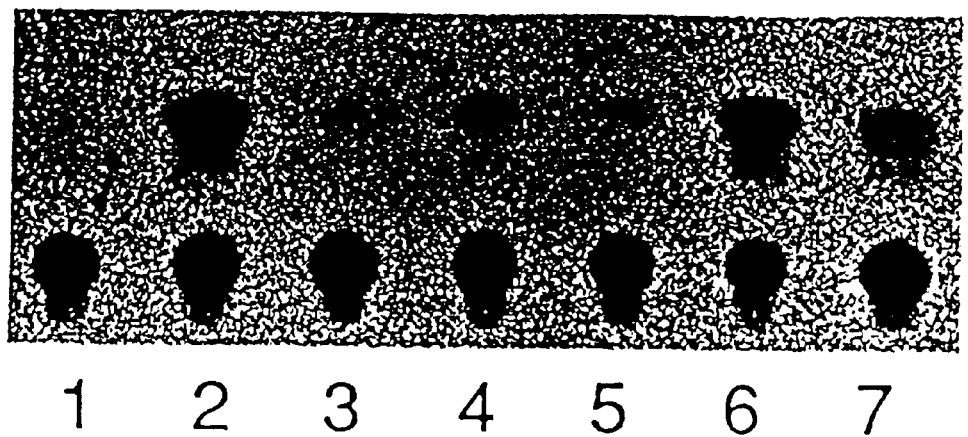

The present inventors have constructed expression vectors used by David Eisenberg's laboratory (Molecular Biology Institute, UCLA 405 Hilgard Avenue, Los Angeles, Calif. 90024) to purify and crystallize Tat.

The effectiveness of a transdominant Tat mutant is dependent on two criteria. One is defective activation of HIV LTR gene expression and the other is the ability to antagonize wild-type Tat function. The present disclosure also outlines methods by which additional transdominant Tat mutants may be constructed and used to generate mutants which satisfy these criteria and serve as better transdominant mutants.

The amino acid sequence of the first 72 amino acids and the nucleotide sequence encoding the amino acids of the Tat protein are illustrated in Table 1.

TABLE 1

| SEQUENCE ID NO: 2 |
| --- |

| Amino-Terminal Domain | | | | | | | | | | | | | | | |
| --- | --- | --- | --- | --- | --- | --- | --- | --- | --- | --- | --- | --- | --- | --- | --- |
| 1 | 2 | 3 | 4 | 5 | 6 | 7 | 8 | 9 | 10 | 11 | 12 | 13 | 14 | 15 | 16 |
| MET | Glu | Pro | Val | Asp | Pro | Asn | Leu | Glu | Pro | Trp | Lys | His | Pro | Gly | Ser |
| ATG | GAG | CCA | GTA | GAT | CCT | AAT | CTA | GAG | CCC | TGG | AAG | CAT | CCA | GGA | AGT |

| | | | | | | | | | | | | | Cysteine-Rich Domain | | |
| --- | --- | --- | --- | --- | --- | --- | --- | --- | --- | --- | --- | --- | --- | --- | --- |
| 17 | 18 | 19 | 20 | 21 | 22 | 23 | 24 | 25 | 26 | 27 | 28 | 29 | 30 | 31 | 32 |
| Gln | Pro | Arg | Thr | Ala | Cys | Asn | Asn | Cys | Tyr | Cys | Lys | Lys | Cys | Cys | Phe |
| CAG | CCT | AGG | ACT | GCT | TGT | AAC | AAT | TGC | TAT | TGT | AAA | AAG | TGT | TGC | TTT |
| 33 | 34 | 35 | 36 | 37 | 38 | 39 | 40 | 41 | 42 | 43 | 44 | 45 | 46 | 47 | 48 |
| His | Cys | Tyr | Ala | Cys | Phe | Thr | Arg | Lys | Gly | Leu | Gly | Ile | Ser | Tyr | Gly |
| CAT | TGC | TAC | GCG | TGT | TTC | ACA | AGA | AAA | GGC | TTA | GGC | ATC | TCC | TAT | GGC |

| Basic Domain | | | | | | | | | | | | | | | |
| --- | --- | --- | --- | --- | --- | --- | --- | --- | --- | --- | --- | --- | --- | --- | --- |
| 49 | 50 | 51 | 52 | 53 | 54 | 55 | 56 | 57 | 58 | 59 | 60 | 61 | 62 | 63 | 64 |
| Arg | Lys | Lys | Arg | Arg | Gln | Arg | Arg | Arg | Ala | Pro | Gln | Asp | Ser | Gln | Thr |
| AGG | AAG | AAG | CGG | AGA | CAG | CGA | CGA | AGA | GCT | CCT | CAG | GAC | AGT | CAG | ACT |
| 65 | 66 | 67 | 68 | 69 | 70 | 71 | 72 | | | | | | | | |
| His | Gln | Ala | Ser | Leu | Ser | Lys | Gln | | | | | | | | |
| CAT | CAA | GCT | TCT | CTA | TCA | AAG | CAG | TAA | | | | | | | |

Changes in the basic region of Tat protein and the tat gene are illustrated in Table 1 appear essential to generate transdominant Tat mutants. A number of neutral amino acid substitutions in the basic domain of Tat between amino acids 49 and 57 result in transdominant Tat mutants. According to the present invention, this basic region was further mutated by substituting neutral amino acids in various novel combinations between amino acids 49 and 57 of the tat gene. A variety of mutants will also be constructed which substitute glutamic acid, rather than the neutral amino acids glycine or alanine, for basic region amino acids. Each construct was assayed in cotransfection assays with HIV LTR CAT and wild-type tat plasmids to better determine the role of amino acid charge on the generation of transdominant Tat mutants. Previous mutagenesis studies have been analyzed by the present inventors, and indicate that preservation of at least three basic amino acids at positions 49, 50, and 51 of the tat gene are critical for the transdominant tat phenotype.

The HIV-1 TAR element is critical for the activation of gene expression by the transactivator protein, tat. Mutagenesis has demonstrated that a stable stem-loop RNA structure containing both loop and bulge structures transcribed from TAR is the major target for tat activation. Though transient assays have defined elements critical for TAR function, no studies have yet determined the role of TAR in viral replication due to the inability to generate viral stocks containing mutations in TAR. The present inventors have generated stable 293 cell lines which were capable of producing high titers of different viruses containing TAR mutations. Viruses generated from these cell lines were used to infect both T-lymphocyte cell lines and peripheral blood mononuclear cells. Viruses containing TAR mutations in either the upper stem, bulge, or loop exhibited dramatically decreased HIV-1 gene expression and replication in all cell lines tested. Lymphoid cell lines which stably expressed gene products from each of these TAR mutant viruses were isolated. Though the amount of virus in these cell lines was roughly equivalent, TAR mutant viruses were extremely defective for gene expression as compared to cell lines containing wild-type virus. The magnitude of this decrease in viral gene expression was much greater than previously seen in transient expression assays using HIV-1 LTR CAT constructs. In contrast to the defects in viral growth found in T-lymphocyte cell lines, several of the viruses containing TAR mutations were much less defective for gene expression and replication in activated peripheral blood mononuclear cells. These results indicate that maintenance of the TAR element is critical for viral gene expression and replication in all cell lines tested, though the cell type which is infected is also a major determinant of the replication properties of TAR mutant viruses.

The low levels of gene expression from viruses containing mutations in TAR prevent the generation of measurable levels of virus using previously described techniques. Though gene expression from HIV-1 TAR mutant proviral constructs can be induced by treatment of T-lymphocyte cell lines with phytohemagglutinin and phorbol esters (Harrich et al., 1990), this protocol to produce TAR mutant viruses is limited by the cytotoxicity of phorbol esters. Previous studies indicate that the adenovirus E1A/E1B can induce gene expression from the HIV-1 LTR (Kliewer et al., 1989; Nabel et al., 1988). This activation requires the SP1 and TATA elements but is not markedly dependent on the TAR element (Kliewer et al., 1989). In the present invention, 293 cells, an E1A/E1B transformed human embryonic kidney cell line (Graham et al., 1977), are used to produce a variety of HIV-1 TAR mutant viruses. These viruses contain mutations that alter either the TAR stem structure, delete the bulge, transpose the bulge to the opposite side of TAR, or change the sequence of the loop. The growth kinetics of each of these viruses are compared on several T-lymphocyte cell lines including H9 (Popovic et al., 1984), Jurkat (Weiss et al., 1984), and a Jurkat cell line constitutively expressing tat (Caputo et al., 1990). In addition, the growth of these viruses was tested on peripheral blood mononuclear cells (PBMCs). These studies demonstrate the importance of the HIV-1 TAR element on modulating viral gene expression and growth properties, though cell-type differences are also critical in regulating the function of TAR.

Previous mutagenesis studies established that the TAR RNA secondary structure, the primary sequence of the loop, and the bulge element were all critical for tat induced gene expression from the HIV-1 LTR (Feng et al., 1988; Garcia et al., 1987; Hauber et al., 1988; Jakobovits et al., 1988; Rosen et al., 1985; Roy et al., 1990a; Roy et al. 1990b; Selby et al., 1989). In the present examples, the present inventors used stable 293 cell lines to generate viruses that contained changes in a variety of different portions of TAR. The constitutive expression of the adenovirus E1A protein in 293 cells was able to provide high levels of HIV-1 gene expression which allowed for the production of these mutant viruses. The use of techniques similar to those described to generate HIV-1 TAR mutants should allow for the production of other types of retroviruses that contain mutations in critical regulatory elements. The ability to obtain sufficient quantities of such viruses should facilitate the study of regulatory elements which control retroviral gene expression and replication.

T-lymphocyte cell lines infected with either wild-type HIV-1 or the TAR stem restoration mutant virus, (+19/+22)/(+40/+43), resulted in a productive infection as determined by the levels of secreted p24 Ag and RT activity. However, all other viruses containing TAR mutations including (+19/+22), (+31/+34), (+40/+43), (+11/+14)/(+40/+43), (+23),Δ(+23/+25), and Δ(+23/+25)/(+37/+39) failed to yield detectable levels of replication in T-cell lines. These results indicate that any mutations that perturb TAR RNA stem structure, the loop, or the bulge are very deleterious for viral gene expression and replication. The defects in gene expression did not appear to be due to differences in the ability of these viruses to infect T-lymphocytes or initiate reverse transcription. Even though most TAR mutant viruses did not give a productive infection in T-lymphocyte cell lines, G418 was used to select Jurkat cells containing roughly equal quantities of each of the TAR mutant proviruses. Though G418 resistant Jurkat cells harboring either the wild-type or the TAR stem restoration mutant provirus (+19/+22)/(+40/+43) expressed similar quantities of p24 Ag, cells containing the TAR mutant proviruses resulted in decreases of viral gene expression ranging from 200 to 5000-fold as compared to Jurkat cells harboring the wild-type provirus. These studies of both viral growth and stable gene expression of integrated proviruses agree with previous studies that indicate TAR is critical for high levels of gene expression from the HIV-1 LTR. However, both of these assays demonstrate that the effects of TAR mutations are of much greater magnitude in the context of virus than with plasmid constructs assayed by transient expression.

It is not known if the decreased viral gene expression observed in drug selected Jurkat cells containing TAR mutant viruses was due to decreased transcriptional initiation and/or decreased elongation. There is considerable experimental evidence that tat has only minor effects on promoter-proximal transcription, but it markedly increases promoter distal transcriptions (Feinberg et al., 1986; Graham et al., 1977; Kao et al., 1987; Kato et al., 1992; Laspia et al., 1989; Laspia et al., 1990; Marciniak et al., 1991). Nuclear run-on studies previously performed with HIV-1 proviral constructs which contained a deleted tat gene demonstrated that the addition of recombinant tat protein to cells containing this HIV-1 proviral construct increased the RNA levels at promoter distal but not promoter proximal sites (Feinberg et al., 1986). Nuclear run on experiments on G418 selected Jurkat cells containing TAR mutant proviruses will be required to determine if these viruses are defective in transcriptional initiation, elongation, or whether some combination of these effects are present.

While most TAR mutant viruses were unable to replicate in cultured T-lymphocyte cell lines, differential replication rates were observed when these same viruses were assayed following infection of activated PBMCs. Mutations that altered the upper portion of the TAR RNA stem structure, (+19/+23) and (+40/+43), replicated slower and gave lower p24 Ag levels than viruses containing mutations of the bulge, (+23) and Δ(+23/+25), or the loop, (+31/+34). The ability of some TAR mutant viruses to replicate in activated PBMCs though at slower rates was intriguing. However, two mutations in TAR prevented viral replication in activated PBMCs. One mutation, (+11/+14)(+40/+43), disrupted both the upper and lower TAR stem structure while the other mutation, Δ(+23/+25)(+37/+39), transposed the bulge to the opposite side of the TAR RNA stem structure. These latter mutants indicate that the maintenance of the overall structure of TAR RNA was required for the activation of the HIV-1 promoter.

Surprisingly, mutations of the bulge, (+23) and (+23/+25), or the loop, (+31/+34), appeared to be less critical for viral replication in PBMCs than mutations that disrupted the upper stem structure, (+19/+22) and (+40/+43). Viruses containing mutations in the bulge or the loop exhibited decreases in both viral replication and gene expression, though these defects did not prevent viral growth. These results indicate that tat may activate HIV-1 gene expression in the absence of the TAR RNA bulge which is required for tat binding (Berkhout et al., 1990; Calnan et al., 1991; Cordingley et al., 1990; Dingwall et al., 1990; Dingwall et al., 1989; Roy et al., 1990a; Roy et al., 1990b; Weeks et al., 1991). However, activation of these viruses is not tat-independent because mutation of tat in these proviral constructs gave no detectable viral gene expression in either 293 cells or T-lymphocytes. In the absence of an intact bulge structure, it is possible that an alternative activation complex can form on TAR which is composed of tat and cellular proteins binding to the TAR RNA loop. Similarly it is possible that in viruses with mutations in the TAR RNA loop that tat bound to the TAR RNA bulge may interact with a complex of cellular proteins that normally bind to the loop.

Previous studies using wild-type and TAR mutant proviruses demonstrated that although the wild-type loop sequences and maintenance of TAR secondary structure were required for efficient gene expression in unstimulated Jurkat cells, a TAR-independent gene activation of these proviruses was observed in Jurkat cells treated with phorbol esters (Harrich et al., 1989). Viruses containing mutations of the loop sequence of disruption of the TAR RNA secondary structure expressed near wild-type levels of p24 Ag in Jurkat cells stimulated with phorbol esters. TAR-independent activation was eliminated by combining mutations of TAR with mutations of the enhancer or by disrupting the tat gene (Harrich et al., 1989). The current study revealed that activated PBMCs were more permissive for viral replication of TAR mutants than H9 or Jurkat cells. It seems likely that the ability of TAR mutant viruses to markedly increase their gene expression in stimulated T-lymphocytes was achieved by the activation of specific cellular transcription factors. The nature of these cellular factors and the HIV-1 control elements which they regulate to mediate high levels of tat-induced gene expression are not known (Barry et al., 1991). The ability to assay the role of different HIV-1 TAR RNA mutations in the context of the virus as provided herein should help elucidate the RNA elements and mechanisms involved in tat-induced gene expression.

Indirect Immunofluorescence

HeLa cells were grown on 100-mm tissue culture plates in Iscoves' medium supplemented with 5% newborn calf serum. At 70 to 80% confluency, the cells were trypsinized and washed twice with 25 to 30 volumes of media. The cells were centrifuged at 1500 rpm for 5 min, the pellet was resuspended in a proper volume of medium to reach about $10^7$ cells per milliliter. Cells ($2 \times 10^6$) were electroporated in the presence of 20 μg of plasmid with a BRL electroporator (at a capacitance of 1180 μF, low resistance, and 250 V). The electroporated cells were resuspended with 1 ml of medium and plated on gelatin-coated glass coverslips.

Cells on coverslips were rinsed with phosphate-buffered saline (PBS) and fixed with methanol at −20° C. for 5 min. After the cells were washed with PBS, they were placed in 50 mM Tris (pH 7.4), 150 mM NaCl, 5% normal goat serum (PBS-NGS), and 0.02% azide for at least 45 min. For indirect immunofluorescence, the samples were incubated with the primary antibody, which was a rabbit polyclonal antibody to a peptide corresponding to amino acids 1 to 17 of the Tat protein as described by Pearson et al., 1990, or a mouse monoclonal antibody directed against the basic domain of Tat as described by Brake et al., 1990, which references are both specifically incorporated herein by reference for this purpose, or both antibodies in the case of double staining. Incubation with the antibodies, diluted 1:400 with PBS-NGS, was at room temperature for 1 h. After washing three times with PBS-NGS, a 1:100 dilution of secondary antibody solution consisting of fluorescein-conjugated goat antiserum to mouse IgG or rhodamine-conjugated goat antisense to rabbit IgG was added to the samples, which were incubated for 1 h. After further washes, the coverslips were mounted on slides in Fluormount G mounting medium. Cells were visualized with a 63× Planapo lens on a light fluorescence microscope.

Plasmid Construction

The proviral construct pBRDH1 contains a permutation of HIV-1 sequences at a unique Mro I located in U3 region of the HIV-1 LTR. It was derived from the molecular clones SF2 Mro I (−156)/Sph I (+988), pBH10 Sph I (+988)/Xho I (+8486), and SF2 Xho I (+8486)/Mro I (+8982) (Sanchez et al., 1985). The complete Mro I DNA fragment was cloned into pBR322 at the unique Mro I site, cut with Cla I (end-filled) and Nru I to remove pBR322 sequences, and closed with T4 DNA ligase. The complete molecular clone was not infectious when transfected into permissive cells unless it was first linearized with the restriction enzyme Mro I. After transfection into a permissive cell line, the linear fragments concatenate and express HIV-1. The LTR mutations were previously described (Garcia et al., 1987; Wu et al., 1991). A vector was constructed from an Ava I (−160) (end filled)/Sph I (+988) DNA fragment from the HIV-1 SF2 isolate which was then cloned into pUC18 linearized with Sma I and Sph I. For each HIV-1 TAR mutant provirus, a Pvu I/Sph I DNA fragment containing each of the TAR mutants from each shuttle was ligated into pBRDH1 cut with the same restriction enzymes.

To insert the neo gene into pBRDH1, a Sma I site was introduced by M13 site directed mutagenesis into pBRDH1. This destroyed the nef (pBH10) initiating methionine and this construct was designated pBRDH2. Next, a Bcl I/Nae I (partial) DNA fragment from TN5 which contains the entire neo gene (Beck et al., 1982) was ligated into the pBSK vector (Stratagene) linearized with Hind II. An EcoRV/Xho I DNA fragment from this construct was ligated into wild-type and mutant pBRDH2 constructs linearized with Sma I (+8385) and Xho I (+8486) to generate the pBRDH2-neo construct.

Cell Lines, Viruses, and Infections

To generate stable cell lines producing wild-type and mutant HIV-1, the human embryonic kidney cell line 293 (Graham et al., 1977) was transfected using calcium phosphate precipitation with 20 µg of either Mro I linearized wild-type or the TAR mutant pBRDH2-neo plasmid. Three days post-transfection, the 293 cells were split 1:40 and maintained in Iscove's medium containing 5.0% newborn calf serum, 2.5% fetal bovine serum, 1% penicillin-streptomycin, and 1 mg/ml G418 (Geneticin, BRL). The media was changed every 4 days until foci appeared and grew to 2 mm in diameter. Cells were removed using cloning wells, expanded, and assayed for HIV (p24) antigen. Cell free supernatants were assayed for reverse transcriptase (RT) activity (Potts, 1990).

To produce supernatant for viral infection, freshly confluent 293 cells producing different HIV-1 mutants were grown for 12–16 hours in RPMI containing 10% fetal bovine serum (heat inactivated), 1% glutamine and 1% penicillin-streptomycin. The culture supernatant was removed, filtered through a 0.4 µm membrane, assayed for RT activity, and used immediately to infect either Jurkat (a human T-cell lymphocytic cell line) (Weiss et al., 1984), Jurkat-tat (Caputo et al., 1990) (the same cell line constitutively expressing the HIV transactivator protein tat), H9 (a human cutaneous T-cell lymphoma) (Popovic et al., 1984), or activated peripheral blood mononuclear cells (PBMCs). These cell lines were maintained in RPMI containing 10% fetal bovine serum, 1% glutamine, 1% penicillin-streptomycin medium. For infection of PBMCs from an HIV-1 seronegative donor, cells were activated for three days with PHA 1 µg/ml and maintained in the same culture medium supplemented with 30 U/ml of interleukin-2 (Ross et al., 1991).

For viral infection, $2 \times 10^6$ cells were incubated with 0.4 µm of filtered 293 supernatants containing $1 \times 10^6$ cpm of total $^{32}$P-RT activity. Cells were incubated with viral supernatants for 8 to 12 hours in 5 ml of culture medium. Next, the cells were pelleted at 400 g, washed three times with 10 ml of culture medium, and resuspended in 10 ml of RPMI containing 10% fetal bovine serum, 1% glutamine, and 1% penicillin-streptomycin. Cultures were split 1 to 7 every three or four days and following centrifugation of aliquots of media at 2000 g to remove cells, they were assayed for RT activity and p24 antigen. To obtain G418 resistant Jurkat cell lines containing TAR mutant viruses, aliquots of infected and uninfected Jurkat cells were placed in culture medium containing 2 mg/ml G418 at four weeks post-infection.

For single cycle HIV-1 infections, approximately $1.5 \times 10^6$ Jurkat cells were incubated with 293 supernatants containing the equivalent of $2 \times 10^6$ cpm of total $^{32}$P-RT activity. Cells were incubated for two hours and the samples were shaken every 15 minutes. The cells were spun at 400 g, washed three times with 10 ml of culture medium, and resuspended in 0.5 ml of cell lysis buffer (760 mM guanidine hydrochloride, 10 mM Tris-HCl, 10 mM EDTA, 10 mM NaCl, pH 8.5). Each sample was frozen and thawed, incubated at 50° C. in the presence of 25 µg proteinase K for one hour, extracted once with phenol/chloroform, and the nucleic acids were precipitated with two volumes of ethanol.

Reverse Transcriptase Assay and ELISA for p24 Ag

A "mini" reverse transcriptase (RT) assay was used to analyze the HIV-1 infected culture supernatants (Potts, 1990). Briefly, 10 µl of cell free supernatant was mixed for ninety minutes at 37° C. with a reaction cocktail containing 50 mM Tris pH 7.8, 7.5 mM KCl, 2 mM DTT, 5 mM $MgCl_2$, 0.05% NP40, 250 ng poly(rA) oligo(dT)$_{12-18}$ (Pharmacia), and 0.5 µCi 32P-dTTP (Amersham, PB 10167). The reactions were spotted onto DEAE paper (Schleicher & Schuell, NA45) and washed three times at room temperature in 2× SSC (0.3 M NaCl, 0.3 M sodium citrate, pH 7.0). Incorporated counts were measured by liquid scintillation. Cell free supernatants were assayed for p24 Ag at a detection limit of 10 pg/ml using an ELISA assay, HIVAG-1 (Abbott), according to the manufacturers instructions.

PCR Analysis

Chromosomal DNA from 293 cell lines and G418 selected Jurkat cells were obtained using Qiagen DNA extraction reagents and used in subsequent PCR analysis. The chromosomal DNA from either HIV-1 producing 293 cell lines or G418 selected Jurkat cells was used in PCR reactions using 0.5 µg of DNA and 0.5 µg of each oligonucleotide; 5'-CCCAAACAAGACAAGAGATTGA-3', SEQ ID NO:19, (sense,-436/-415) and 5'-CCTGCGTCGAGAGAGCTCCTCTGG-3', SEQ ID NO:20 (antisense, +242/+219). Each sample was subjected to 35 cycles at 55° C. for annealing, 72° C. for synthesis, and 95° C. for denaturing with 1 minute at each temperature. The resulting DNA fragments, which included most of the 5' LTR and the primer binding site, were ligated into the vector pCRII (Invitrogen) and sequenced using sequenase reagents (USB).

PCR conditions used to analyze the single cycle infections and G418 selected Jurkat cells containing TAR mutant viruses were previously described (Zack et al., 1990). Briefly, two oligonucleotide primers, 5'-GCTAACTAGGGAACCCACTGC3', SEQ ID NO:21 (sense, +44/+64) and 5'-CTGCTAGAGATTTTTCCACACTGAC-3', SEQ ID NO:22 (antisense, +183/+159), were used to amplify a 139 bp fragment from the R/U5 junction of the HIV-1 LTR. Approximately 0.1 µg of total DNA isolated from the infected cells was subjected to 25 cycles of PCR using 30 ng of $^{32}$P end-labeled sense primer ($5 \times 10^8$ cpm/µg) along with 100 ng of unlabeled antisense primer and reactions incubated first at 65° C. for two minutes and then at 92° C. for one minute. The HIV-1 standards used represent a molecular SF-2 (Sanchez et al., 1985) proviral clone present at either 0 copies, 10 copies, $10^2$ copies, $10^3$ copies, or $10^4$ copies containing 100 ng of sonicated herring sperm carrier DNA. A pair of oligonucleotide primers complementary to the first exon of the human β-globin gene nucleotide which generates a 110 bp band between positions 14–33 (5'-ACACAACTGTGTTCACTAGC-3', SEQ ID NO:23) and 123–104 (5'-CAACTTCATCCACGTTCACC-3', SEQ ID NO:24) were used as a control for the total amount of DNA in each reaction. PCR products were resolved on a 6% polyacrylamide gel followed by autoradiography.

Northern (RNA) Analysis

Total RNA was extracted from Jurkat and 293 cells with RNAsol B per manufactures instructions (Biotecx Laboratories). An agarose gel containing 1% formaldehyde was used in electrophoresis of 30 µg of total RNA at 100V for 3 hrs. The separated RNA was transferred overnight to nitrocellulose by the capillary method and the filter was baked for two hours at 80° C. A Bam HI(+8050)/Sma I(+8385) DNA fragment from pBRDH2 was labeled by random priming (Boehringer Mannheim) with $^{32}$P-dCTP which is capable of hybridizing to all spliced and unspliced HIV-1 RNA transcripts. Blots were pre-hybridized and then hybridized overnight at 47° C. in 1× hybridization solution (BRL) containing 50% formamide, 0.1% SDS, and 1×10$^6$ cpm/ml of denatured probe at 47° C. The filter was then washed with 2× SSC (0.3 M NaCl, 0.3 M sodium citrate, pH 7.0, 0.1 SDS) at room temperature and 0.2× SSC containing 0.1% SDS at 65° C. for 15 minutes prior to autoradiography.

Western Immunoblot Analysis

Whole cell supernatants were prepared from 293 cells and G418 selected Jurkat cell lines each containing different HIV-1 TAR mutants. A pellet containing 1×10$^7$ cells was frozen and thawed twice and then treated with 1000 units of micrococcal nuclease (Worthington Biochemical) at 37° C. for 30 minutes. Each cell pellet was resuspended in 1× Laemmli buffer at a concentration of 1×10$^8$ cells/ml, and heated to 95° C. for 10 minutes. Whole cell extract prepared from 5×10$^5$ Jurkat or 1×10$^6$ 293 cells was subject to electrophoresis on a 12% polyacrylamide gel, transferred to nitrocellulose, and probed with a 1:5000 dilution of purified human anti-HIV-1 IgG (NIG AIDS Research and Reagent Program #192). A second antibody, HRP conjugated rabbit anti-human IgG (Amersham), which was diluted 1:2000 was then used for enhanced chemiluminescence (ELC) detection (Amersham).

Even though the present invention has been described with a certain degree of particularity, it is evident that many alternatives, modifications, and variations will be apparent to those skilled in the art in light of the following disclosure. Accordingly, it is intended that all such alternatives, modifications, and variations which fall within the spirit and the scope of the invention be embraced by the defined claims.

The following examples are presented to describe preferred embodiments and utilities of the present invention, but should not be construed as limiting the claims thereof.

EXAMPLE 1

Construction of Truncated and Substituted Tat Mutants

To further characterize the requirements for transdominant inhibition by Tat, a series of mutant Tat proteins are described herein which were prepared by (i) introducing stop codons at different positions in the gene that would alter the basic domain of the protein, or (ii) substituting multiple neutral amino acid codons for basic amino acid codons.

Two types of mutations were used to construct the variety of proteins of the present invention having an altered basic domain (FIG. 1). In one type, stop codons that altered the basic domain of Tat between amino acids 49 and 58 were introduced and resulted in a variety of truncated Tat constructs. In the other type of mutations, we substituted different basic domain codons (A [tat 52/57], B[tat 54/57], and C[tat 55/58]) with codons for neutral amino acids thus changing the overall basic charge of the Tat protein (FIG. 1).

The fragment HincII-SspI corresponding to the second exon of tat was cloned into the HincII site of pUC19. For oligonucleotide-directed mutagenesis a HindIII-BamHI fragment was cloned into M13mp18 as previously described (Garcia et al., 1988). The oligonucleotides made to the coding strand of tat contained the mutations shown in FIG. 1. For substituted constructs, the A (tat 52/57) mutant containing Gly-Gly-Ala-Gly-Gly-Gly (SEQ ID NO: 4) in place of Arg-Arg-Gln-Arg-Arg-Arg (SEQ ID NO: 8) was prepared with the use of an oligonucleotide with the sequence 5'-GGG GGA GCC GGC GGA GGA-3 (SEQ ID NO: 9); the B (tat 54/57) mutant containing Ala-Gly-Gly-Gly (SEQ ID NO: 6) in place of Gln-Arg-Arg-Arg (SEQ ID NO: 10) was prepared with the use of an oligonucleotide with the sequence 5'-GCC GGC GGA GGA-3' (SEQ ID NO: 11); and the C (tat 55/58) mutant containing Gly-Ala-Gly-Gly (SEQ ID NO: 7) in place of Arg-Arg-Arg-Ala (SEQ ID NO: 12) was prepared with the use of an oligonucleotide with the sequence 5'-GGA GCC GGC GGT-3'(SEQ ID NO: 13). The synthesized oligonucleotides were treated with polynucleotide kinase in the presence of ATP and used for mutagenesis according to the conditions described by the manufacturer of a commercial site-directed mutagenesis kit (Amersham) which reference is specifically incorporated herein by reference.

In the case of the truncated constructs, three stop codons (TGA TAA TAA) were added in frame, followed by a BglII site. DH5αF' cells were transformed with the mutagenized plasmids, positive plaques were determined by screening, and the sequences were confirmed by the dideoxy sequencing method. Fragments containing the mutated tat genes were cloned into a eukaryotic expression vector, pDEX (Garcia et al., 1988).

These resulted in 3 substitution as well as truncated tat constructs. Each of these mutated tat constructs was cloned downstream of the RSV promoter in order to express the genes in transfection experiments.

EXAMPLE 2

Basic Domain Mutations and Production of Transdominant Tat Mutant Proteins

The present example is provided to demonstrate the utility of particular tat mutants for providing the synthesis of transdominant Tat mutant proteins and thereby demonstrate the in vivo utility of the claimed invention for inhibiting HIV expression and infection in vivo.

To demonstrate the effects of basic domain mutations on the ability of the mutant proteins to antagonize wild-type Tat activation, cotransfection experiments were performed.

Cell Transfection and CAT Assays

HeLa cells were maintained on complete Iscoves' medium supplemented with 5% newborn calf serum, 2.5% fetal bovine serum, and penicillin and streptomycin. At 24 h prior to transfection, the cell cultures were split and plated on 60-mm plates at a density that permitted them to reach between 50 and 70% confluency at the time of the transfection. The transfections were performed by the calcium phosphate technique in the presence of 5 μg of the HIV-1 LTR CAT construct and the amounts of RSV-Tat and the RSV-tat mutants indicated in each experiment. The total concentration of the RSV expression vector in each transfection was kept constant (5 μg) by the addition of an RSV-β-globin construct. At 4 h after transfection, the cells were subjected to a glycerol shock, and 48 h later they were harvested, washed, and resuspended in 100 μl of 0.25 M Tris, pH 7.8. The cell extracts were prepared and CAT assays were done as previously described (Gorman et al., 1982). CAT activity from the HIV-1 LTR CAT construct was determined by measuring both unacetylated and acetylated $^{14}$C-labeled chloramphenicol. The specific level of HIV-1 LTR CAT trans-activation of each tat construct was determined by subtracting the basal level obtained with the RSV-β-globin construct alone. Using the specific levels of trans-activation, the percent conversion of each tat construct was calculated relative to the trans-activation seen with wild-type Tat.

The HIV-1 LTR CAT plasmid was transfected with an RSV expression construct (Garcia et al., 1989) containing a mutated tat gene and a similar construct containing a wild-type tat gene in equimolar concentrations (FIG. 2A) or a 20-fold molar excess of the mutated tat construct over the wild-type tat construct (FIG. 2B). Transfected cells were harvested at 48 h and the level of trans-activation by Tat proteins was calculated by measuring CAT activity. The basal level of expression and the percentage of trans-activation were determined as described supra.

As shown in FIG. 2A, a number of truncations of the tat gene between the codons for amino acids 49 and 58 resulted in proteins that inhibited Tat activation when the vector expressing the mutant protein was transfected at equimolar concentrations with a vector expressing wild-type Tat (FIG. 2A, lanes 2 to 11). For most of these mutants, the degree of inhibition was 3- to 4-fold compared to the wild-type protein (FIG. 2A). However, equimolar concentrations of vectors expressing wild-type Tat and constructs A (tat 52/57), B (tat 54/57), and C (tat 55/58) (the substitution mutants) resulted in a 5- to 7-fold inhibition of wild-type Tat activation (FIG. 2A, lanes 12 to 14). Thus, proteins with the specific truncations or substitutions in the basic domain described above were able to inhibit Tat activation when their expression vectors were present in equimolar concentrations with a vector expressing wild-type Tat. This is in contrast to the inventors previously described Δtat mutant, which exhibited its maximal phenotype only when the vector expressing it was present in an 5- to 30-fold molar excess over a vector expressing the wild-type Tat.

When the concentration of each of the vectors expressing Tat proteins with truncations in the basic domain was increased to a 20-fold molar excess over the vector expressing the wild-type protein, further inhibition of wild-type Tat activation of the HIV-1 LTR was seen (FIG. 2B, lanes 2 to 11). Maximum inhibition occurred with constructs derived by introducing stop codons at positions 52, 53, and 54 (FIG. 2B, lanes 5 to 7). These constructs resulted in a 10- to 15-fold inhibition of wild-type Tat trans-activation of the HIV-1 LTR (FIG. 2B).

The substitution mutants, which include substitutions in the basic domain, also resulted in marked inhibition in Tat activation at these same molar excesses (FIG. 2B, lanes 12 to 14). This inhibition was most evident with a protein that had a substitution of six amino acids in the basic domain, C (tat 52/57) (FIG. 2B, lane 14). This mutant routinely resulted in a 15- to 20-fold inhibition of wild-type Tat activation when the vector expressing it was present in at least a 5-fold molar excess over the vector expressing the wild-type Tat.

These results indicated that both truncations and substitutions that alter the basic domain of Tat result in proteins that antagonize wild-type Tat activation of the HIV-1 LTR. However, the potency of each of the various mutant constructs is demonstrated to vary, depending on the particular substitution examined.

EXAMPLE 3

Trans-Activation of the HIV-1 LTR by Tat Proteins with an Altered Basic Domain

To determine if the degree of inhibition correlates with residual trans-activation capability of the transdominant Tat mutants, each of the transdominant Tat mutants was tested for its ability to trans-activate the HIV-1 LTR (FIG. 3A and 3B). The HIV-1 LTR CAT construct was cotransfected with the wild-type tat vector or each of the vectors expressing a transdominant Tat mutant. As in Example 1, the total concentration of the RSV expression vector in each transfection was kept constant by the addition of an RSV-β-globin vector.

As shown in FIG. 3A, cotransfections of vectors expressing a mutant tat (0.1 μg) and HIV-1 LTR CAT constructs revealed that each of the proteins with an altered basic domain was defective in its ability to activate the HIV-1 LTR (FIG. 3A, lanes 2 to 14) compared to similar concentrations of a vector expressing wild-type Tat (FIG. 3A, lane 1). The maximum activation of the HIV-1 LTR with the mutant proteins was only 20% of that seen with wild-type Tat.

When the concentration of vectors expressing mutant Tat proteins was increased 20-fold (2.0 μg), mutants with truncations of the basic domain downstream of amino acid 55 reduced the level of activation of the HIV-1 LTR to 40 to 60% of that obtained with similar concentrations of the vector expressing wild-type Tat (FIG. 3B, lanes 8 to 11). However, at these same DNA concentrations, constructs containing multiple substitutions in the Tat basic domain were still severely defective in their ability to activate the HIV-1 LTR (FIG. 3B, lanes 12 to 14).

These results indicated that at low vector concentrations, proteins with an altered (substituted) basic domain were very defective in their ability to activate the HIV-1 LTR, while at higher vector concentrations, proteins with truncations between amino acids 55 to 58 were able to produce nearly wild-type levels of activation.

EXAMPLE 4

HIV Replication is Inhibited by the tat 52/57 Construct

The present example provides a comparative analysis of the truncated mutant, ▲tat(STOP3), of Pearson et al. and the transdominant mutant 52/57 (TDN3) of the present application in their ability to protect a lymphoid cell line from HIV-infection.

Figure 8:
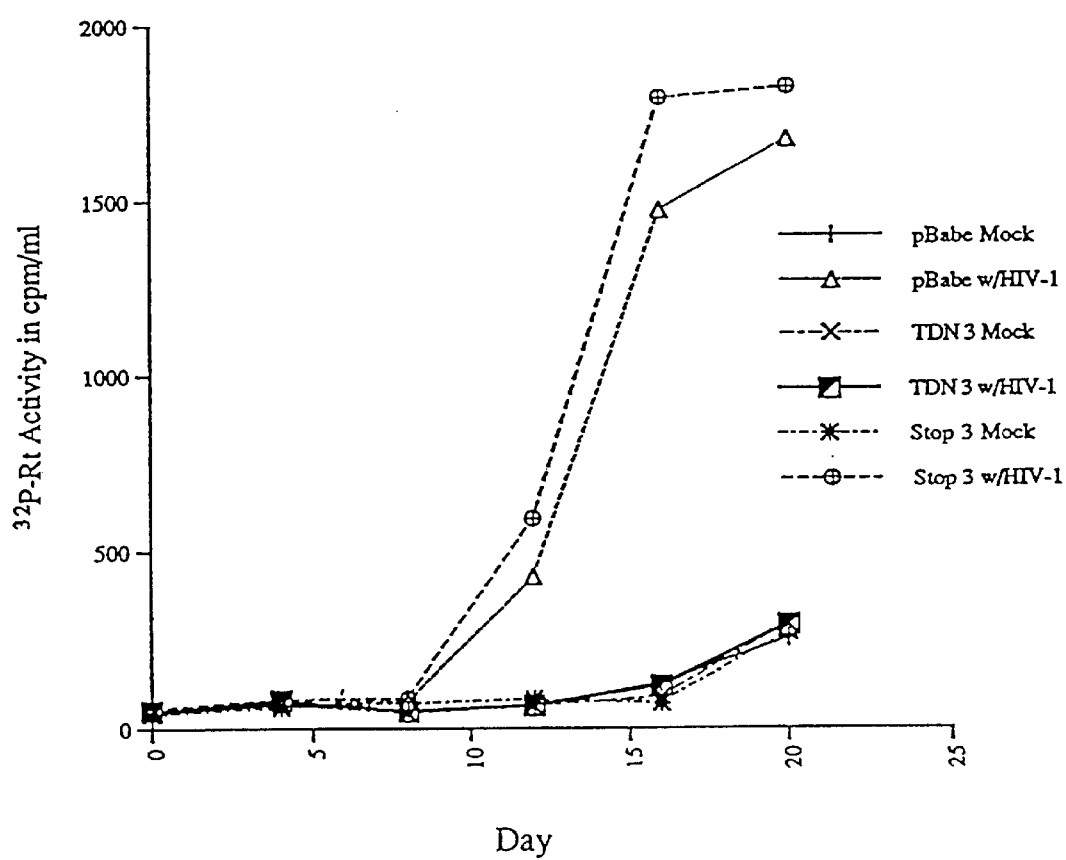
Figures 9D, 9E, 9F:
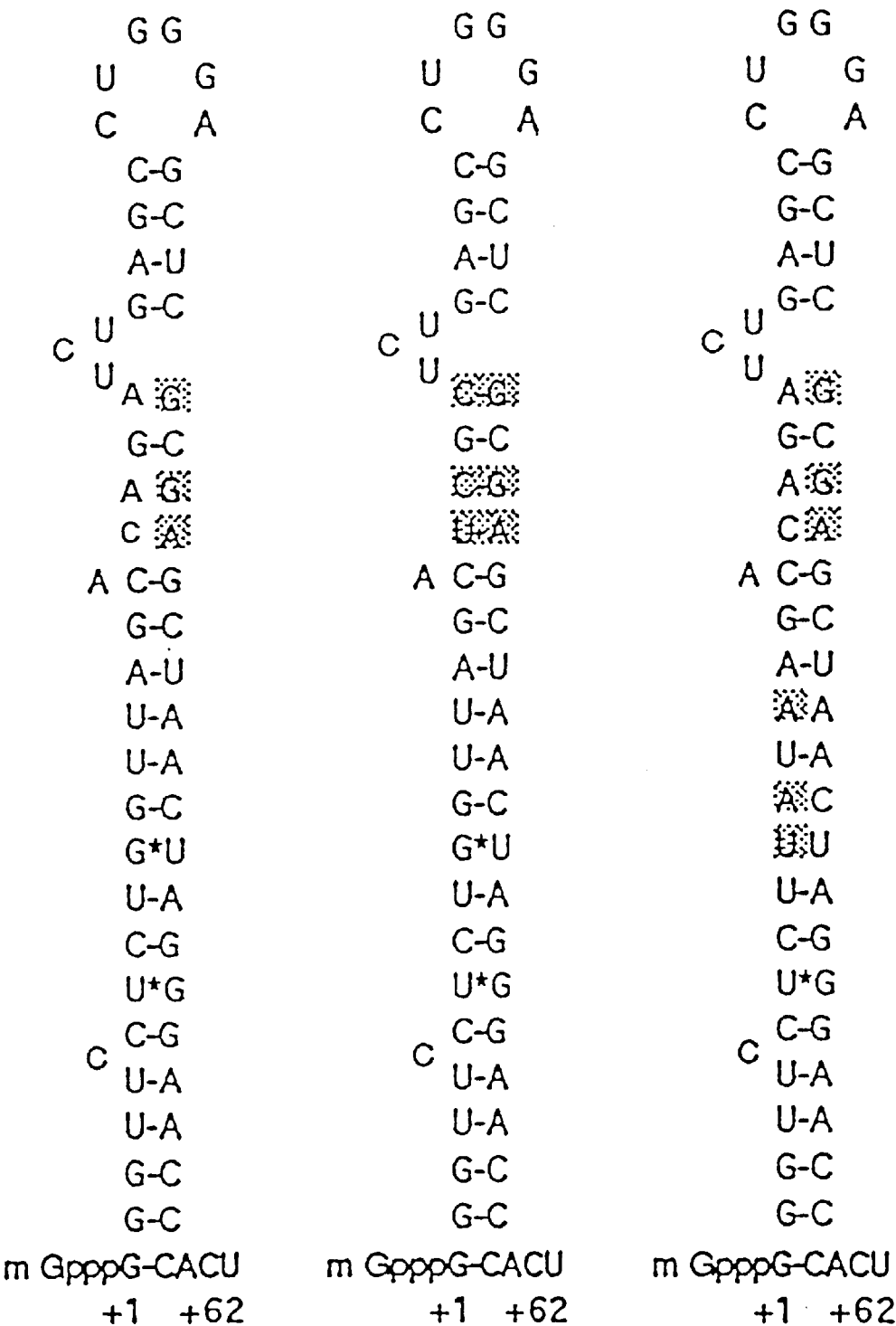
Figures 9G, 9H, 9I:
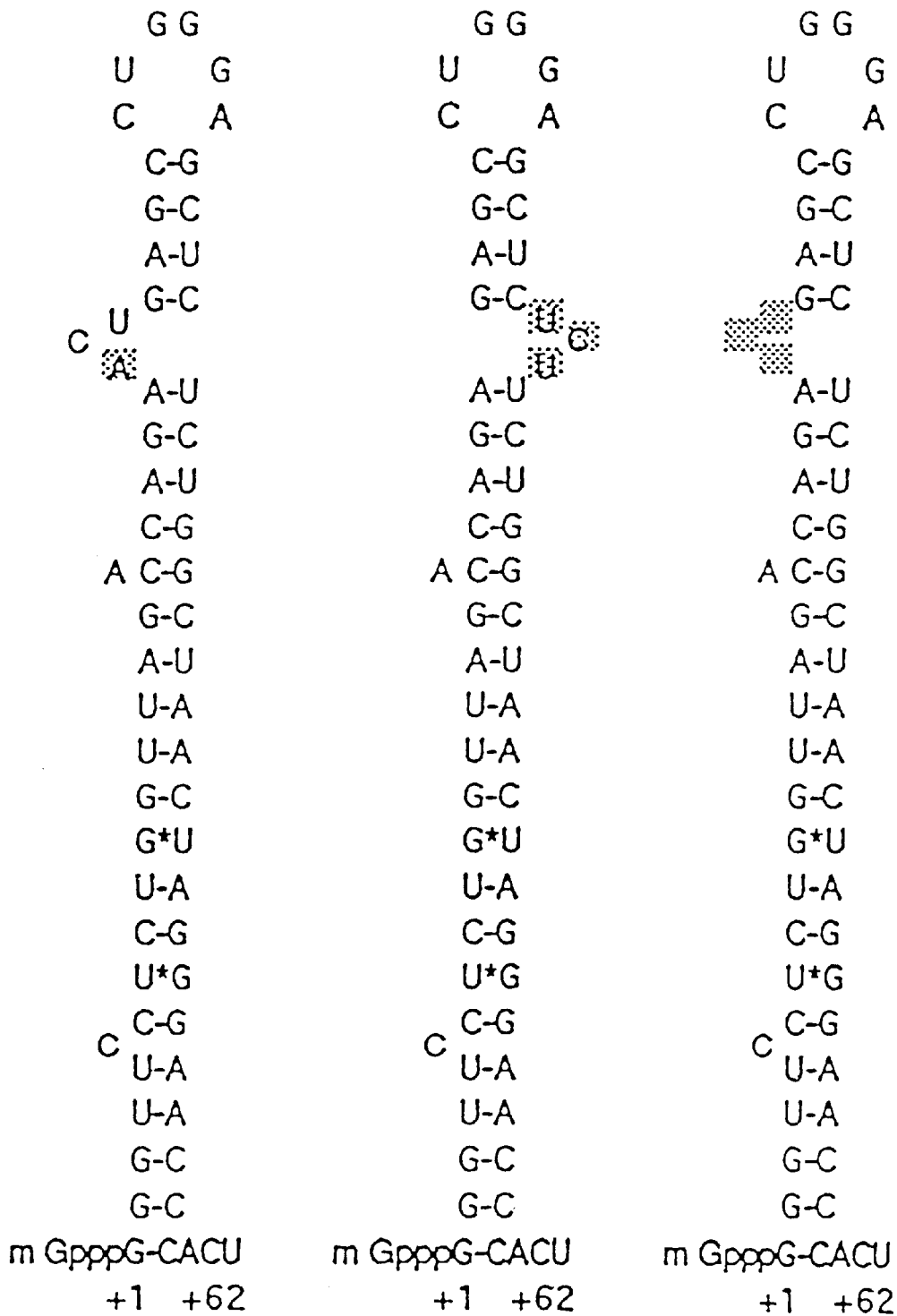

In this experiment, twenty nanograms of p24 antigen from wild-type HIV-1 was used to infect $10^7$ H9 lymphoid cells containing either vector alone (pBabe), ▲tat (Stop 3 of Pearson et al.) or 52/57 (of the present application, also named TDN 3) constructs. Reverse transcriptase assays were performed every 4 days. FIG. 8 demonstrates the results of the comparative analysis. The figure legend is as follows:

pBabe mock—control vector without HIV,
pBabe w/HIV-1—control vector with HIV,
TDN 3 Mock—52/57 construct
TDN 3 w/HIV-1—52/57 construct with HIV
Stop 3 Mock—▲tat construct
Stop 3 w/HIV-1—▲tat construct with HIV The data show that stable H9 lymphoid cell lines containing the ▲tat gene of Pearson et al. were infected with wild-type HIV in a manner that was similar to infection of control H9 cells. In contrast, H9 cell lines containing the 52/57 construct markedly inhibited HIV replication for up to three weeks as compared to control cell lines. Thus, the ▲tat cell line did not protect from HIV infection whereas the 52/57 cell line did protect from HIV infection.

The results of this comparative analysis demonstrate: i) those cells unchallenged by HIV demonstrated background reverse transcriptase activity; ii) cells having the transdominant mutant 52/57 of the present invention and challenged by HIV also demonstrated background reverse transcriptase activity; iii) cells having no construct or the Pearson et al. Stop 3 construct were infected by HIV upon challenge by HIV as seen by the significant increase in reverse transcriptase activity beginning at day 8. Therefore, the truncation mutant of Pearson et al. did not inhibit HIV-1 growth whereas the substitution mutant of the present invention did inhibit HIV-1 growth.

EXAMPLE 5

Effect of TAR Element Mutations on Transdominant Inhibition

The present example is provided to demonstrate that mutations in the TAR RNA stem structure, the sequence of the bulge region, and the primary sequence of the loop of the TAR RNA structure influence to varying amounts the degree of transdominant inhibition with the tat 52/57 construct.

Figure 4B:
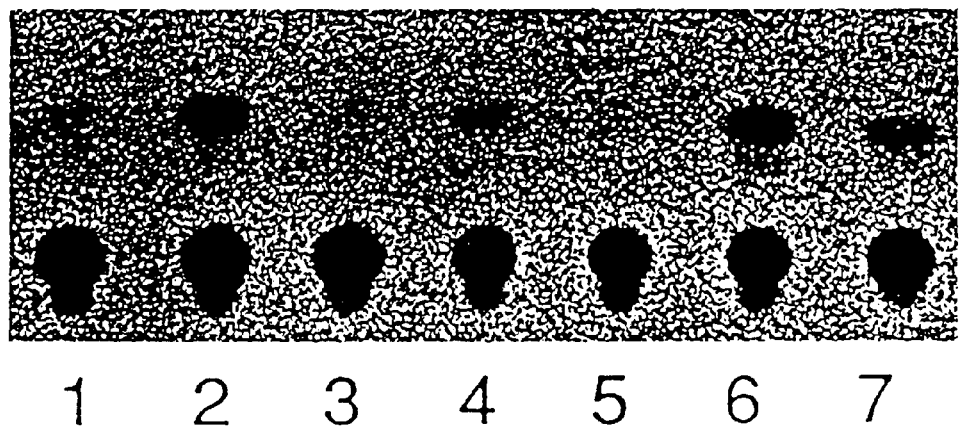

CAT activity produced by HIV-1 LTR constructs containing either wild-type TAR, or a variety of TAR mutants in the presence of a vector expressing wild-type Tat alone (FIG. 4A), or both wild-type Tat and tat 52/57 (FIG. 4B), were assayed as described herein. As shown in FIG. 4A, compared to wild-type TAR, mutations of the loop, stem, or bulge of TAR resulted in a marked decrease in wild-type Tat activation (FIG. 4A, lanes 2 to 7). By including tat 52/57 in these transfections in a 5-fold molar excess over the vector expressing wild-type Tat, the level of CAT activity produced with both wild-type and mutant TAR constructs was reduced approximately 5- to 10-fold (FIG. 4B, lanes 2 to 7).

These results demonstrate that transdominant inhibition by the substitution mutant tat 52/57, was not dependent on any single element of the TAR RNA structure, but was due to a general mechanism of Tat function.

EXAMPLE 6

Transdominant Activation and the Effect of Native TAR Element

The lack of dependence of transdominant inhibition on the structure of the TAR RNA was confirmed and extended in the present example with tat 52/57 mutant effect on Tat-R17 fusion proteins.

Figure 5A:
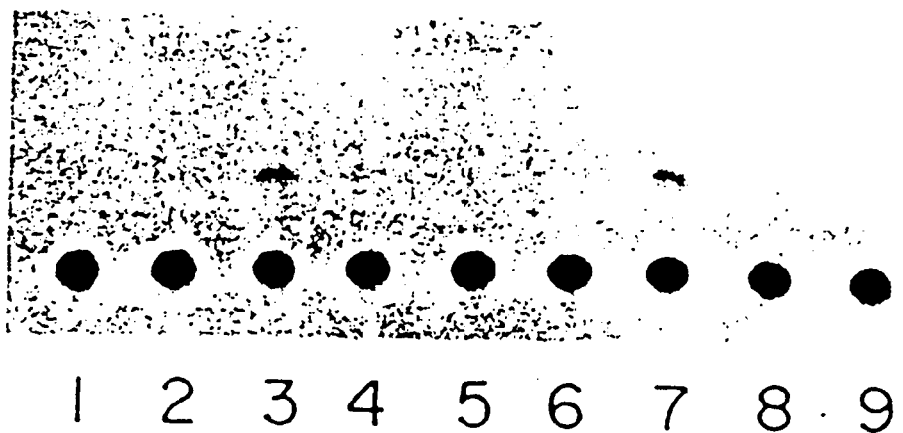
Figure 5B:

Both the tat-R17 construct (FIG. 5A, lane 3) and the tat-R17 construct with the basic domain deletion (FIG. 5A, lane 7) were able to activate the HIV-1 LTR that contained the R17 recognition element inserted into the TAR element to about 5% of the level of activation obtained with the wild-type HIV-1 LTR (FIG. 5B, lane 3). A previous report indicates that Tat-R17 fusion proteins were capable of activating the HIV-1 LTR containing R17 binding sites (Selby et al., 1990).

It was next determined whether either an equimolar or a 5-fold molar excess of tat 52/57 could inhibit HIV-1 LTR activation by tat-R17 constructs.

As demonstrated in FIG. 5, tat 52/57 was able to severely inhibit activation of R17 recognition element by both the Tat-R17 fusion protein (FIG. 5A, lanes 5 and 6) and the Tat-R17 protein with the basic domain deletion (FIG. 5A, lanes 8 and 9). CAT activity was inhibited by at least 10-fold compared to the activity measured in the absence of tat 52/57. Thus, the presence of an intact TAR element was not critical for transdominant inhibition. Furthermore, transdominant inhibition could occur in the absence of the wild-type Tat basic domain in Tat-R17 fusion proteins.

EXAMPLE 7

Effect of Transdominant Tat Mutants on Tat Nuclear Localization

It was important to study the mechanism by which transdominant mutants inhibited activation of the HIV-1 LTR by Tat. One potential mechanism of this inhibition was a defect in the nuclear localization of Tat in the presence of a transdominant Tat mutant (Pearson et al., 1990). The present example demonstrates co-transfection of a vector expressing wild-type Tat and a vector expressing a transdominant Tat mutant do not inhibit the nuclear localization of wild-type Tat.

To perform these studies, two types of antibodies were used. One was a rabbit polyclonal antibody to an amino-terminal Tat peptide corresponding to amino acids 1 to 17 of the Tat protein (Pearson et al., 1990) which was capable of recognizing both wild-type Tat and transdominant Tat mutant protein. The other was a mouse monoclonal antibody directed against a portion of the basic domain of Tat (Brake et al., 1990); this antibody reacts with wild-type Tat but not tat 52/57. A construct expressing wild-type Tat and an excess of a construct expressing a transdominant Tat mutant were transfected into HeLa cells. The cells were examined by immunofluorescence with the two antibodies, each one labeled with either rhodamine or FITC. The site of localization of both Tat and the transdominant mutant in the cotransfection assays could then be determined.

Figure 6A:
Figure 6B:
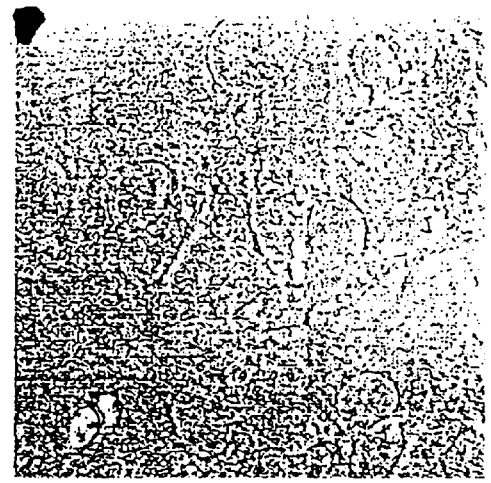
Figure 6C:
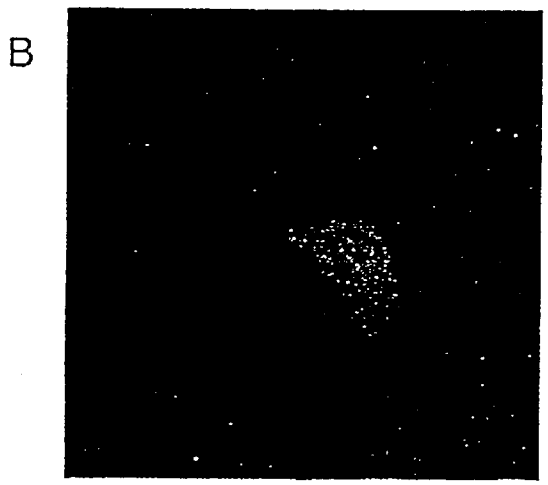
Figure 6D:
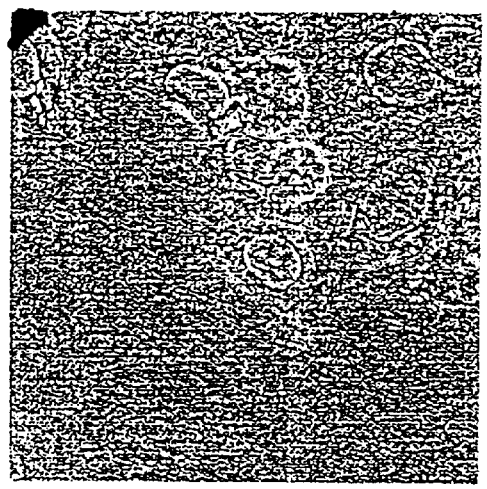

As shown in FIG. 6A, Tat was localized primarily in the nucleus when the wild-type construct was transfected alone into HeLa cells (Hauber et al., 1987; Ruben et al., 1989; Hauber et al., 1989; Siomi et al., 1990;). When the tat 52/57 construct was transfected alone, tat 52/57 was present in both the nucleus and the cytoplasm (FIG. 6C–6D). When the tat 52/57 vector was present in cotransfections in a 5-fold molar excess over the vector expressing wild-type Tat, the transdominant mutant protein was present in both the nucleus and the cytoplasm (FIG. 6D) and wild-type Tat was present only in the nucleus (FIG. 6E).

These results demonstrate that the transdominant mutant did not inhibit Tat function by significantly impairing its transport to the nucleus.

EXAMPLE 8

Construction of Cell Lines Containing Transdominant Tat Mutants

The present example is provided to demonstrate a preferred method for preparing cell lines which contain transdominant Tat mutants, and to demonstrate the utility of the present invention for creating a transdominant Tat mutant cell line from virtually any cell line. Cell lines containing transdominant tat mutants are also described at Example 11.

Previous studies with a herpes virus transdominant mutant in the transactivator protein VP16 revealed that this gene can be used to create stable cell lines which are resistant to infection by herpesvirus. The present inventors will use similar approaches to develop cell lines which are resistant to HIV-1 infection. Either the transdominant tat mutant, tat 52–57 (which substitutes glycine or alanine residues between amino acids 52 and 57 of Tat), or another tat mutant Δcys (which changes three critical cysteine residues at amino acids 22, 27, and 34 of the tat gene), was introduced into one of two Moloney virus derived retroviral vectors both of which contain neomycin resistance genes (Wu et al., 1991). However, any of the transdominant tat mutants as described in the present disclosure may be inserted to provide cell lines with those particular corresponding transdominant Tat mutants.

One vector will use the Moloney LTR to direct expression of the tat genes. In the other vector, a metallothionein promoter inserted downstream of the Moloney LTR will direct synthesis of the tat cDNA. These retroviral vectors have been used to successfully express the transforming growth factor, b1.

Following insertion of the tat gene into these vectors, each vector will be transfected into the ecotropic-vector cell line, Y2, and cell lines selected with G418 as described. Ecotropic vector stocks will be used to infect PA317 cells, and following G418 selection, amphotropic stocks will be harvested and titers determined (Morganstern, J. P. and Land, H. (1990) *Nucl. Acids Res.*, 18:3587–3596). These stocks can be used to infect a variety of T-cells and monocyte cell lines. Each of these viruses will be used to infect a variety of T-lymphocyte cell lines including Jurkat and H9 and the monocyte cell line U937. Following selection with G418, resistant cell lines will be isolated and the presence of the transdominant tat gene confirmed by PCR analysis of DNA isolated from these cells and Western blot analysis using polyclonal Tat antibodies. These cells will then be tested for their ability to be infected with HIV-1. Cell free supernatant containing HIV-1 will be used to infect cells and p24 Ag and reverse transcriptase levels will be performed daily as described. The metallothionein promoter within the retroviral vector is expected to be useful in production of the Tat protein.

The present inventors have found that production of high levels of the Tat proteins in stable lymphoid cell lines frequently proves toxic. Thus, the ability to induce tat with cadmium sulfate (1 mM) may make it possible to better propagate the cells and induce Tat production at the time of HIV-1 infection. This level of cadmium appears to be free of significant cellular toxicity, but control cell lines will be included in each study. Thus, the determination of whether either constitutive or inducible expression of transdominant tat mutants in stable cell lines alters their ability to be infected by HIV-1 may be made.

Transdominant tat mutants will also be introduced into HIV proviral constructs in place of the wild-type tat gene. Since the tat gene is critical for HIV-1 gene expression, very little viral expression would be expected in virus containing mutant tat genes, and it would likely prove difficult to obtain high titer stocks of such a virus. However, the advantages of using such a virus as a vector to deliver transdominant tat mutants to cells would be its low endogenous expression in uninfected cells and its potential inducibility by wild-type Tat protein produced by wild-type HIV infection. After infection of cells containing the virus with the transdominant tat gene by wild-type HIV, the transdominant protein would likely be induced and wild-type HIV-1 gene expression could potentially be decreased.

Example 11 describes a vector for this use under "Proviral construction". A human embryonic kidney cell line, 293 cells, that constitutively produces the adenovirus E1A and E1B proteins, have been demonstrated by the present inventors to induce high level gene expression from tat mutant proviruses. Thus, it is possible to select G418 resistant 293 cell lines containing tat mutants so that viral stocks of high titer can be obtained. These stocks will be used to infect H9, Jurkat and U937 cells and G418 resistant cells will be selected. The ability of such cell lines containing transdominant tat mutants to express their gene products will first be determined by addition of wild-type Tat protein to the tissue culture media as described. Both p24 and reverse transcriptase will be assayed to determine if these proviruses are capable of producing high levels of their gene products in the presence of wild-type Tat.

These stable cell lines will then be tested for their ability to be infected with wild-type HIV. Uninfected neomycin resistant cell lines and cell lines containing proviruses with large internal deletions in their tat genes will be used as controls. Monoclonal antibodies directed against the carboxyl terminus of Tat will be used in immunoprecipitation assays to determine the ability of the wild-type virus to infect these cells. Following infection with wild-type virus, p24 and reverse transcriptase assays will be performed. Due to the extremely low expression of these mutant viruses, it is unlikely that they will result in decreased CD4 antigen levels preventing infection by the wild-type virus. Thus, it can be determined whether virus containing the transdominant tat gene can inhibit wild-type HIV gene expression.

The transdominant tat mutant viruses will also be used to infect monocytes, lymphocytes, and peripheral blood lymphocytes previously infected with HIV. This type of study may prove difficult because wild-type viral infection may decrease CD4 levels preventing superinfection. PCR analysis of cellular RNA using primers flanking the neomycin gene will be performed to determine if infection by the virus containing the transdominant tat mutant occurs. A reduction in the levels of p24 and reverse transcriptase in response to infection by the transdominant tat mutant virus but not other viruses containing tat deletions will be interpreted to indicate that viruses carrying transdominant tat mutants inhibit wild-type viral gene expression. These studies will serve as a useful model for the development of viruses with anti-viral properties.

EXAMPLE 9

Production of Transdominant Tat Mutant Proteins which Inhibit HIV-1 Gene Expression The present example is provided to outline the method which will be employed to demonstrate the production of transdominant tat mutant protein within cell lines.

Several studies indicate that bacterial produced Tat protein is capable of entering cells in culture by endocytosis (Jones et al., 1986; Rice et al., 1990). This process is stimulated by the addition of protamine sulfate and inhibited by agents such as heparin. The work of the present inventors has demonstrated that both Tat and a transdominant Tat mutant with a substituted amino acid sequence 52 to 57, tat 52–57, could be produced in bacteria as fusions with the glutathione S-transferase protein (Wu et al., 1991). Authentic proteins can be produced following binding of these fusion proteins to glutathione-agarose columns and cleavage of the Tat moiety by treatment with thrombin at a recognition site engineered between the two proteins.

The wild-type Tat protein was greater that 95% pure and bound to TAR RNA with high affinity. The transdominant Tat mutant was also greater than 95% pure but bound poorly to TAR RNA. As a positive control for defective activation of HIV gene expression, a Tat protein with several critical cysteine residues substituted with other amino acids, Δcys, which is known to result in defective activation of HIV gene expression, will also be produced in this bacterial expression system (Garcia et al., 1988; Wu et al., 1991).

The ability of either wild-type Tat protein, tat 52–57, or Δcys added to Hela cells to alter gene expression of a transfected HIV LTR CAT construct in both the presence and absence of a tat expression construct will be determined. If no inhibition of Tat activation of the HIV LTR CAT construct is seen with tat 52–57, it will then be determined whether the construct gains entry into the cells and its cytoplasmic and nuclear localization. Either protamine sulfate or heparin will be added with these bacterial synthesized Tat proteins to attempt to alter their cellular uptake as described (Mann, D. A. and Frankel, A. D. (1991), *EMBO J.*, 10:1733–1739). The ability of the tat 52–57 mutant to inhibit HIV-1 gene expression in infected cells will be further investigated. From 1 to 40 mg of either tat 52–57 or Δcys will be added to either HIV-infected Jurkat, H9, or U937 cells every 24 hours. Both p24 and reverse transcriptase assays will be performed to determine the potential role of these Tat proteins on inhibiting HIV-1 gene expression. Tritiated thymidine labeling of cells will be performed to rule out potential toxic effects due to associated contaminant bacterial proteins.

The present inventors believe it is possible that Tat synthesized in bacterial expression systems may not have the same functional activity as similar proteins produced in eucaryotic cells. In addition, bacterial contaminant proteins may prove toxic to cells. To circumvent these problems a wild-type tat and tat mutants tat 52–57 and Δcys will also be produced in eucaryotic cells. A number of viral and cellular proteins have been successfully produced to high levels using vaccinia expression systems. Various tat constructs will be cloned downstream of the T7 promoter in the vaccinia expression vector pTM1. (Elroy-Stein, O., Fuerst, T. R. and Moss, B. (1989), *Proc. Natl. Acad. Sci. USA*, 86:6126–6130). This vector also contains a T7 polymerase terminator sequence and a thymidine kinase gene which undergoes insertional activation upon recombination with wild-type vaccinia virus.

These constructs will be transfected into CV1 cells previously infected with wild-type vaccinia virus and thymidine-kinase negative recombinant virus will be identified following infection of 143 cells. Expression from the recombinant virus will be induced by coinfection with a vaccinia virus containing T7 polymerase. Recently, a modification of this expression system has been used in which an epitope from the influenza hemagglutinin with the amino acid sequence, MYFYDVPDYASLGGP (SEQ ID NO:14) (Field, J. et al. (1988), *Mol. Cell Biol.*, 8:2159–2165), is fused to the protein of interest. A monoclonal antibody known as 12CA5 directed against this epitope sequence binds proteins containing this sequence avidly and peptides corresponding to this sequence can be used to elute epitope-tagged proteins from affinity columns containing these monoclonal antibodies (Field, J. et al. (1988), *Mol. Cell Biol.*, 8:2159–2165). These techniques were used to characterize the human retinoblastoma protein which was expressed in vaccinia and purified by monoclonal antibody affinity chromatography (Templeton, D. (1992), *Mol. Cell Biol.*, 12:435–443). Both wild-type and mutant tat genes will be cloned into vaccinia vectors containing the influenza epitope sequences in their carboxyl terminus to allow synthesis of a Tat-epitope fusion protein. Transfection assays in our laboratory indicate that properties of wild-type tat and transdominant tat genes were not altered when fused with the epitope in their carboxyl terminus.

Recombinant vaccinia viruses will be isolated and dot blot analysis performed to assay for the presence of tat DNA as described (Elroy-Stein et al. (at p. 42)). These recombinant viruses will be used to infect HeLa cells in combination with helper virus encoding T7 polymerase to induce high level expression of the Tat proteins. Whole cell extracts will be prepared from infected HeLa cells and chromatographed on a heparin agarose column using a 0.1 to 1.0 M KCL gradient. Fractions from this column will be assayed by Western blot analysis using both influenza epitope monoclonal antibody (Field et al. (at p. 42)) and monoclonal Tat antisera (Modesti, N. et al. (1991), *New Biol.*, 3:759–768). Fractions containing Tat proteins will be bound to a Sepharose column containing influenza epitope monoclonal antibody 12CA5 and eluted using peptide corresponding to the epitope amino acid sequence. Thus, purified Tat proteins can be produced and purified in large quantities from eucaryotic cells using these vaccinia expression system.

Between 1 to 10% of the total cellular protein is frequently the product of cDNAs cloned into vaccinia. Purified wild-type Tat, tat 52–57, and Δcys proteins prepared using vaccinia expression systems will be placed into the tissue culture media and their effects on the expression of HIV LTR CAT reporter constructs transfected into HeLa cells in both the presence and absence of a cotransfected tat gene will be assayed. The effects of these proteins on the expression of HIV-1 in infected cells will also be assayed. These results will be correlated with those obtained using Tat protein from bacterial expression systems. Both vaccinia and bacterial produced Tat proteins will also be assayed using in vitro transcription of the HIV LTR to determine potential differences in their activity (Marciniak, R. A. et al. (1990), *Cell*, 63:791–802) and subjected to structural studies.

Upon identifying transdominant Tat mutants of minimal size using transfection assays with HIV LTR CAT and tat constructs, peptides corresponding to these Tat proteins will be synthesized. Following HPLC purification and amino acid sequence analysis of these peptides, their effects on the expression of HIV LTR CAT constructs and on HIV-1 infected cell lines by addition of the peptides to tissue culture media will be tested. Control peptides will also be used to rule out nonspecific effects of synthesis and purification. This will provide a third method to assay transdominant proteins in an attempt to inhibit HIV-1 gene expression.

EXAMPLE 10

Mechanisms of Transdominant Tat Inhibition

The mechanism by which transdominant Tat mutants inhibit wild-type Tat function is not understood. However, several lines of evidence suggest potential mechanisms. For example, immunofluorescence analysis indicates that the transdominant Tat mutant does not prevent the nuclear localization of the wild-type Tat protein. Transdominant Tat mutants are able to inhibit the function of Tat-R17 protein fusions which are capable of activating HIV-1 gene expression via R17 binding sites inserted in place of the TAR element. These results suggest that transdominant mutants do not function by competing with Tat for binding to TAR RNA. The inventors have not yet been able to demonstrate dimerization between Tat and the transdominant Tat mutant. Though none of these results definitively addresses the mechanism of transdominant Tat function, it may be that the transdominant Tat mutants may interact with cellular proteins required for wild-type Tat function. Thus it is important to further investigate the existence of such cellular factors.

Low level expression from stable cell lines containing an integrated tat gene, the quality of Tat antibodies available, and the difficulty of eluting Tat from cells while maintaining interaction with cellular factors have been difficulties associated with determining if cellular factors, such as EIA, tax, and cyclin, directly complex with Tat.

One approach that may solve several of these problems is to infect either HeLa, lymphoid, or monocyte cell lines with vaccinia expression vectors containing either wild-type tat, tat 52–57, or Δcys containing the influenza epitope in their carboxyl terminus and immunoprecipitating Tat and potential associated cellular proteins with monoclonal antibody 12

CA5 directed against the influenza hemagglutinin epitope. From 18 to 24 hours post infection, cells will be labeled with $^{35}S$ cysteine and immunoprecipitation will be performed using the monoclonal antibody 12CA5 or an unrelated monoclonal antibody. At these times post-infection inhibition of host protein syntheses is limited. A number of different protocols will be utilized to attempt to identify conditions that result in the elution of Tat from cells, but prevent its potential dissociation from associated cellular factors. This will involve elution with various salt concentrations ranging from 100 mM to 500 mM in both the presence and absence of NP-40. Following immunoprecipitation and autoradiography, the pattern of cellular factors associated with tat, tat 52–57, and Δcys will be compared. Cellular factors in common with wild-type Tat and the transdominant mutant would potentially be targets for involvement in Tat activation.

Next, these associated cellular proteins will be produced in sufficient quantities for further analysis. Large quantities of epitope-tagged Tat can be produced in vaccinia and bound to Sepharose columns containing 12CA5 monoclonal antibody. Following column elution with low concentrations of KCl (0.1M), both Tat and associated cellular proteins will be eluted with increasing KCl concentrations. Associated proteins eluted from this column will be identified by Coomassie staining. The potential role of these proteins in HIV-1 gene expression will be determined by performing gel retardation assays with various HIV LTR DNA and RNA regulatory elements and in vitro transcription assays with the HIV-1 LTR (Marciniak et al. (at p. 44)).

A similar approach to analyze cellular factors that bind to both the Tat protein and the transdominant Tat mutant would be to couple glutathione S-transferase Tat fusion proteins to glutathione-agarose (Wu et al., 1991). Nuclear extracts will be chromatographed through these columns, eluted with increasing concentrations of KCl, and analyzed as described above. The pattern of associated cellular proteins will be compared to that obtained from immunoprecipitation of cells infected with vaccinia expression vectors containing tat. Thus the pattern of cellular factors associated with both Tat and the transdominant Tat mutant can be determined. Common factors will be extensively analyzed and potentially preparative scale purification and cloning of the genes encoding these proteins will be performed.

EXAMPLE 11

Construction of Mutant Tat HIV Retroviral Vectors and Infected Cell Lines

The present example is provided to demonstrate one particularly preferred method whereby an HIV vector which includes at least one of the mutant tat genes described herein, such as the tat 52/57 mutant, the tat 54/57 mutant or the tat 55/58 mutant, may be prepared.

Like most retroviruses, the human immunodeficiency virus (HIV) genome encodes two structural genes gag and env, as well as the enzyme reverse transcriptase from the pol gene. In addition, HIV makes the regulatory proteins rev and tat, which are essential for the virus life cycle, and nef which is not essential and acts to reduce virus expression. HIV proviral constructs with tat mutations are extremely defective, producing little or no detectable viral antigen when transfected into the lymphocytic cell lines. Other viral transactivators can stimulate transcription from the HIV LTR independent of tat. These include the E1a and E1b proteins from adenovirus and the immediate early proteins of cytomegalovirus. 293 cells are CD4⁻ human embryonic kidney cells that express E1a and E1b proteins from adenovirus. Early experiments demonstrated that these cells could produce mutated virus but at low levels. The cells produce virus for about two weeks but after a month no viral antigens are detectable. This suggests that 293 cells are not easily reinfected, even cell to cell on plates, and are likely sensitive to the cytopathic effects of HIV. Another possibility is the infected cells do not grow as well as uninfected cells and are eventually diluted from the pool of cells. It is now demonstrated that introducing a drug resistance gene into the HIV genome will overcome these difficulties by selecting for a purified population of cells producing recombinant HIV. The drug resistance genes chosen provide protection against puromycin or G418 and were inserted into HIV at the nef open reading frame.

Pro Viral Construction

The plasmid pBR322 was cut with Nru I (bp 972) and Cla I (bp23) and end-filled with Klenow and religated. This vector was cut with Mro I (bp 1664) and ligated with HIV pro viral DNA which contain nucleotides 359–1455 from ARV-2B, nucleotides 1451–8955 from the HTLV IIIB derivative pBH10, and nucleotides 8920–9475 from ARV-2B. The composite construct produces virus when cut with Mro I and transfected into a number of cell lines including Hela, Jurkat, and 293. Using PCR mutagenesis, a Sma I restriction site was introduced at the initiating ATG of the nef gene of HIV.

```
bp 8847 nef ATG
    aagatgggtgg          (SEQ ID NO: 15)

aagatcccggg          (SEQ ID NO: 16)
       Sma I
```

The puromycin gene was excised as a Hind III/Cla I fragment from the vector pBabepuro and was subcloned in pBKS-. An Eco RV/Xho I fragment from this plasmid was subcloned into the pro viral construct which contains the mutagenized NEF gene. This creates a functional and fully expressed puromycin gene from the HIV LTR. The neomycin gene was excised from the transposon Tn-5 as a Bcl I/Nae I (Partial), endfilled with klenow, and subcloned into the Eco RV site of pBKS-. The Fragment was screened for the desired orientation and excised as a Sma I/Xho I. This fragment was inserted into the pro viral construct containing the mutagenized nef gene. The resulting constructs are pBRHIV-ΔNEF, pBRHIV-puro, and pBRHIV-neo.

Construction of Pro Viral tat Mutant Stop 3

An Eco RI (bp5781)/Asp 718 (bp6390) from pBH10 was subcloned into pUC 19 and used as a template for PCR mutagenesis using the pUC 19 reverse sequencing primer AGCGGATAACAATTTCACACAGGA (SEQ ID NO: 17) and the

```
oligomer TCCTATGGCAGGAAGAAGCGGAGATAGTGATGAAGACCTCCTCAA    (SEQ ID NO: 18).
         EcoNI.                    stop stop stop
```

This mutation does not affect the amino acid sequence of rev in an overlapping reading frame. The PCR product was confirmed by sequencing and subcloned as an EcoNI/Asp 718 fragment into an intermediate containing HIV nucleotides 5781–6641 from pBH10. A Sal I/DraIII fragment from this intermediate was subcloned into pBRHIV-ΔNEF, pBRHIV-puro, and pBRHIV-neo. The new constructs are pBRHIV-ΔNEF/stop3, pBRHIV-puro/stop3, and pBRHIV-neo/stop3.

Production and Analysis of tat Stop3 HIV Virus (1) Transfection and Tissue Culture Techniques To produce the mutant tat virus, the proviral constructs pBRHIV-puro/stop3 and pBRHIV-neo/stop3, as well as the corresponding wild type constructs, were cut with the restriction enzyme Mro I and transfected into the human embryonic kidney cell line 293 on 100 mm plates by the calcium phosphate technique. 293 cells were grown and maintained in complete Iscove's supplemented with 5% fetal bovine serum, 5% new born calf serum, penicillin, streptomycin, and gentamicin. The transfected plates were split 48 hours post-transfection 1:20 into media supplemented with either 1.5 ug/ml puromycin or 1.0 mg/ml G418 where appropriate. The cells were fed fresh media every three or four days. In approximately two weeks small cell patches were visualized on the plates and allowed to grow until they became about 3 mm in diameter. Cell foci were removed from the plates with cloning wells and transferred to a 24 well plate. The cells were allowed to grow to confluence then transferred to a 12 well plate, then to a 60 mm plate and finally to a 100 mm plate.

293 Spinner cell lines were currently under development. The process is similar but cell line are isolated by limiting dilution of a transfected pool of cells.

(2) Analysis of Virus Production

A reverse transcription (RT) assay as well as a commercial ELISA assay to the viral antigen p24 (Abbott Laboratories) were used to assay supernatant from the cloned cell lines. 293 cells expressing either HIV-neo or HIV-puro produce 30–250 ng/ml of p24 antigen and from $5 \times 10^5$ cpm/ml to $3 \times 10^6$ cpm/ml RT units of activity. 293 cells expressing either HIV-neo/stop3 or HIV-puro/stop3 produce from 3–30 ng/ml p24 antigen and these supernatants are RT positive. To insure that the mutations were faithfully maintained, two approaches were used to verify the tat stop3 gene. First, chromosomal DNA was isolated from each cloned cell line. Next, oligomer primers which flank the entire first exon of Tat were used to synthesize the Tat gene by PCR. This fragment was cloned into pUC 19 and the entire gene sequenced. A second approach was to isolate a viral pellet, extract the viral RNA, reverse transcribe this RNA and directly sequence tat stop3 using a PCR sequencing technique.

The above-described unique methodologies include the introduction of the Tat and tat mutants into HIV and the successful growth of these viruses on 293 cells. In addition, 293 cells constitute a preferred cell line for the growth of mutant HIV virus, which can then be used for preparing a vaccine according to standard formulation strategies known to those of skill in the medical and pharmaceutical arts (see Remmingtons Pharmaceutical Sciences, 18th edition (1990), specifically incorporated herein by reference in pertinent part).

PROPHETIC EXAMPLE 12

Methods for Treating HIV-Related Infections in an Animal

The present prophetic example is provided to outline a method for using the herein described mutant tat gene containing vectors and/or mutant Tat proteins encoded by the mutant gene, in the treatment of an HIV or HTLV viral infection in an animal, such as a human. Most particularly, the present example outlines a method which may be used in the treatment of humans for the HIV-1 infection known as AIDS. The described methods and therapeutic agents are also contemplated to be effective for the treatment of AIDS related diseases, such as ARC.

To develop transdominant Tat mutant peptides for therapeutic use, it is important to develop transdominant mutants of minimal size, such as the particular substitution mutants and truncated mutants described herein. Minimal size for a proposed peptide mutant is important as the incidence of partial products and yields of peptide is known to decrease significantly as the size of the peptide increases. The minimal size of the claimed transdominant Tat mutant peptides is therefore of advantage in that they provide for both a highly effective and stable product in vivo, as well as for providing for the cost effective efficient production of small peptides.

The basic domain of the Tat protein is known to be critical for nuclear localization and RNA binding (Fisher et al., 1986; Frankel et al., 1988), and enhances HIV gene expression by binding to a particular bulge region of the TAR RNA, which defines the role of this protein in HIV-1 trans-activation. HIV-1 trans-activation is also demonstrated to be critical in HIV gene expression. Therefore, mutation of this basic domain at the particular amino acid residues of the tat gene, as indicated in the foregoing examples, will effectively shut down HIV gene expression. It is contemplated that the information collected by the inventors regarding the effect of various basic domain tat gene mutants on HIV gene expression may be used to develop a vaccine of purified viral antigen which would render animals immunized with the vaccine immune to HIV infection. Specifically, and antigen consisting of a peptide corresponding to the basic domain of the tat gene, specifically at amino residues 49–57, may be employed as part of a vaccine to immunize animals against HIV and AIDS diseases.

Cloned Viral tat DNA

Information generated regarding the effect of mutation of the basic domain of the tat gene (between amino acids 49–57), specifically in the production of tat gene substitution mutants (A-52/57; B-54/57; C-55–58) or truncated mutants (truncated at amino acid 49–53, 55, 56, 57 or 58), may be used to prepare a vaccine useful in the immunization of animals, including humans, against HIV and other HIV-like infections, such as AIDS. Specifically, it is contemplated that the segment of the HIV tat gene corresponding to at least part of the basic domain between amino acids 49–57 may be cloned and used to generate specific, purified HIV Tat basic domain peptide, most preferably as part of an insoluble, fused bacterial-viral protein. Such a fusion protein will then be combined with an effective adjuvant safe and acceptable for use in humans.

The tat gene encoding the basic domain peptide may most preferably be cloned into a prokaryotic cell using a plasmid or bacteriophage vector. Subsequently, the cloned viral DNA for the tat gene basic domain may be expressed as viral protein in either prokaryotic or eukaryotic cells. Most preferably, a eukaryotic cell will be employed to achieve expression of the viral basic domain tat gene.

EXAMPLE 13

Construction of Infectious TAR Mutant Viruses and Production by 293 Cells

The present example provides for the construction of infectious TAR mutant viruses and production of the viruses by 293 cells. Utility of the TAR mutant viruses as providing highly efficient cells for the production of useful materials in the development of viral vaccines, particularly vaccines against HIV infection, is also illustrated in the present example.

The preservation of the upper stem structure of TAR RNA between +18 and +43 is critical for tat activation (Berkhout et al., 1989; Feng et al., 1988; Garcia et al., 1989; Hauber et al., 1988; Jakobotis et al., 1988; Roy et al., 1990; Selby et al., 1989). In addition, the upper portion of TAR RNA contains two important regulatory elements that are also important for tat activation. One is the three nucleotide bulge between positions +23 and +25 (Berkhout et al., 1989; Calnan, et al., 1991; Dingwall et al., 1990; Roy et al., 1990a; Roy et al. 1990b) and the other is a six nucleotide loop between positions +30 and +35 (Berkhout et al., 1989; Calnan, et al., 1991; Dingwall et al., 1990; Roy et al., 1990a; Roy et al. 1990b). A variety of TAR mutations that disrupted the upper stem, (+19/+22) and (+40/+43), changed the primary sequence of the loop (+31/+34), altered the bulge, (+25) and Δ(+23/+25), transposed the bulge to the opposite side of the stem structure, Δ(+23/+25)/(+37/+39), disrupted both the upper and lower stem structure (+11/+14)/(+40/+43), or restored stem structure but altered the primary sequence (+19/+22)/(+40/+43) (FIG. 9A–9I). HIV LTR CAT reporter plasmids containing these or similar mutations resulted in a 3 to 20-fold decrease in tat mediated gene expression when compared to a wild-type construct (Berkhout et al., 1989; Feng et al., 1988; Garcia et al., 1989; Hauber et al., 1988; Jakobovits et al., 1988; Rosen et al., 1985; Roy et al., 1990b; Selby et al., 1989). However, another construct (+19/+22)/(+40/+43), which maintained stem secondary structure, but altered the primary sequence of TAR was not defective for tat-induced gene expression (Garcia et al., 1989; Wu et al., 1991).

Each of these TAR mutations was inserted into the proviral vector pBRDH1 that contains the entire HIV-1 genome permuted at a unique Mro I site in the HIV-1 LTR. This construct contains only one copy of HIV-1 LTR, but it is not infectious unless linearized with the restriction enzyme Mro I and transfected into permissive cells. The DNA is efficiently ligated when transfected into mammalian cells generating concateramized fragments that express viral RNAs (York-Higgins et al., 1990). Though significant quantities of wild-type virus were generated using this procedure, attempts to produce similar levels of TAR mutant viruses in a variety of human cell lines including HeLa, Jurkat, H9, and Jurkat-tat cells were unsuccessful. This was likely due to the marked defects in gene expression seen with these TAR mutants.

The present inventors improved upon the low level of gene expression seen with HIV-1 TAR mutants by performing transfection of these constructs onto cell lines which expressed the adenovirus transactivator E1A. E1A can markedly increase HIV-1 gene expression in the absence of tat in a manner which is not strictly dependent on TAR structure (Kliewer et al., 1989). For these experiments, the human embryonic kidney cell line, 293 which stably expresses E1A in addition to a second adenovirus protein E1B was used. Transfection of 20 μg of linearized HIV-1 proviral DNA containing each of the TAR mutants into 293 cells produced low levels of secreted p24 antigen (Ag). However, no detectable reverse transcriptase activity was identified and passage of these transfected 293 cells resulted in the complete loss of viral gene expression indicating that gene expression from these mutants was transient.

Figure 10:
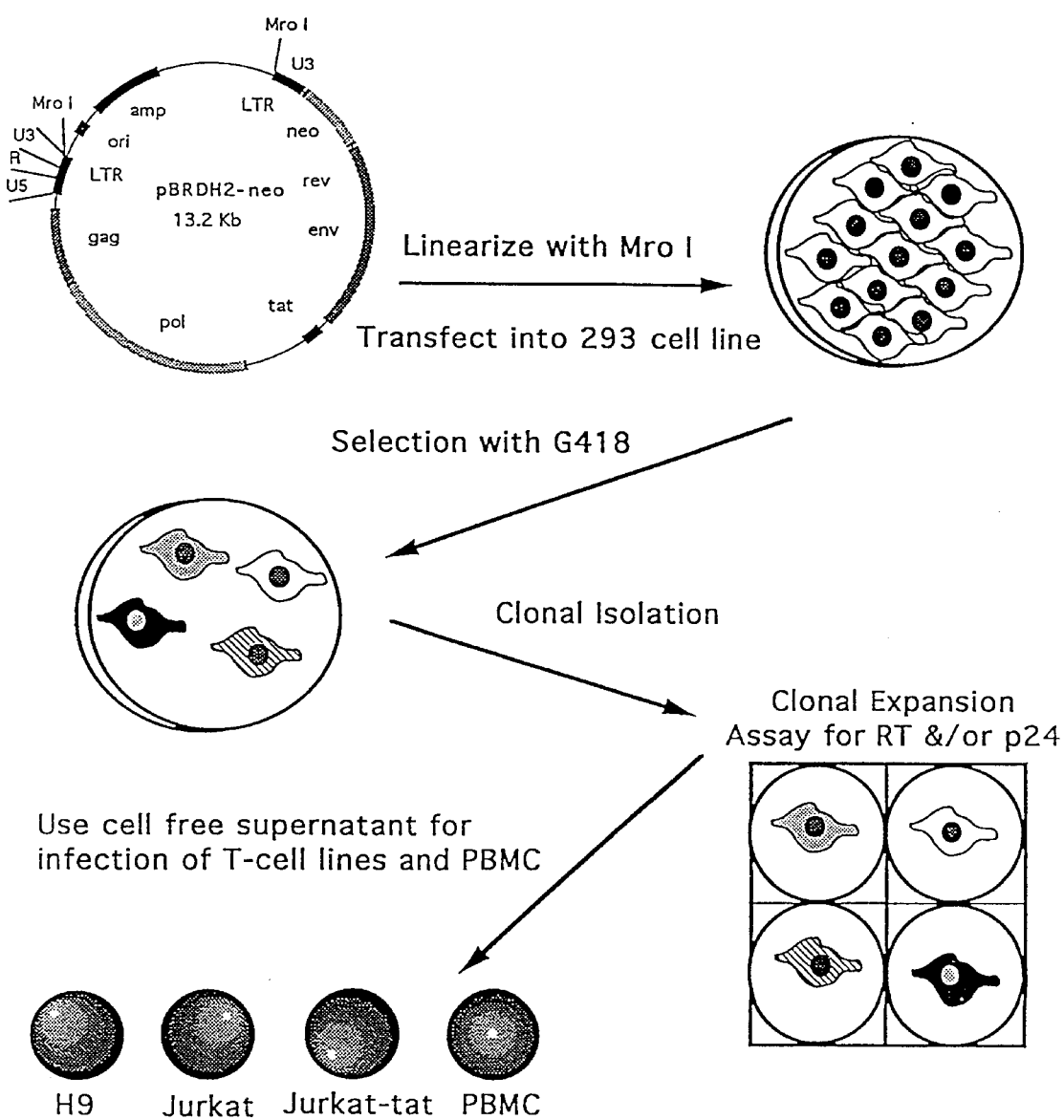

The present inventors isolated stable 293 cell lines which express HIV-1 TAR mutant viruses. To perform these experiments, the neomycin phosphotransferase II or neo gene (Beck et al., 1982) was inserted into the nef open reading frame so that cells containing these viruses could be selected with G418. This was possible because the nef gene is not essential for HIV-1 replication in tissue culture (Fisher et al., 1986; Terwilliger et al., 1986). Oligonucleotide-directed mutagenesis was performed to eliminate the nef initiating methionine prior to the insertion of the neo gene into the nef open reading frame of wild-type HIV-1 and each of the TAR mutants. Following the transfection of HIV-1 proviral constructs containing TAR mutations into 293 cells, cell lines were selected with G418 that contained each of these viruses. The procedures used to generate stable 293 cell lines containing each of the HIV-1 TAR mutant viruses is diagrammed in FIG. 10.

The HIV-1 TAR mutant virus produced by 293 cell lines were assayed for their ability to replicate in both human peripheral blood mononuclear cells and cultured T-lymphocyte cells. The inventors demonstrated that several TAR mutant viruses, particularly (+11/+14)/(+40/+43) and (+30/+34), replicated poorly in IL-2 stimulated human peripheral blood mononuclear cells as well as the cultured T lymphocyte cell lines H9, Jurkat, and a Jurkat cell line stably expressing HIV-1 Tat protein. These HIV-1 TAR mutant viruses behave as genetically attenuated viruses and thus are suitable for use as a live attenuated vaccine. The use of 293 cells is unique and desirable. Virus produced by this cell line are genetically stable since 293 cells are not subject to super infection by other HIV-1 viruses since they lack the CD4 receptor necessary for HIV-1 entry and do not suffer from cytotoxic effects due to virus production. 293 cell lines containing TAR mutant viruses may be adapted to large scale synthesis using hollow fiber culture or spinner culture techniques. The cellular supernatants produced by these cell lines contain virus which is easily purified by either centrifugation or a two step gel filtration column chromatography. Purified virus may be resuspended in appropriate pharmacological buffer for use as a genetically attenuated live vaccine.

Figure 11A:
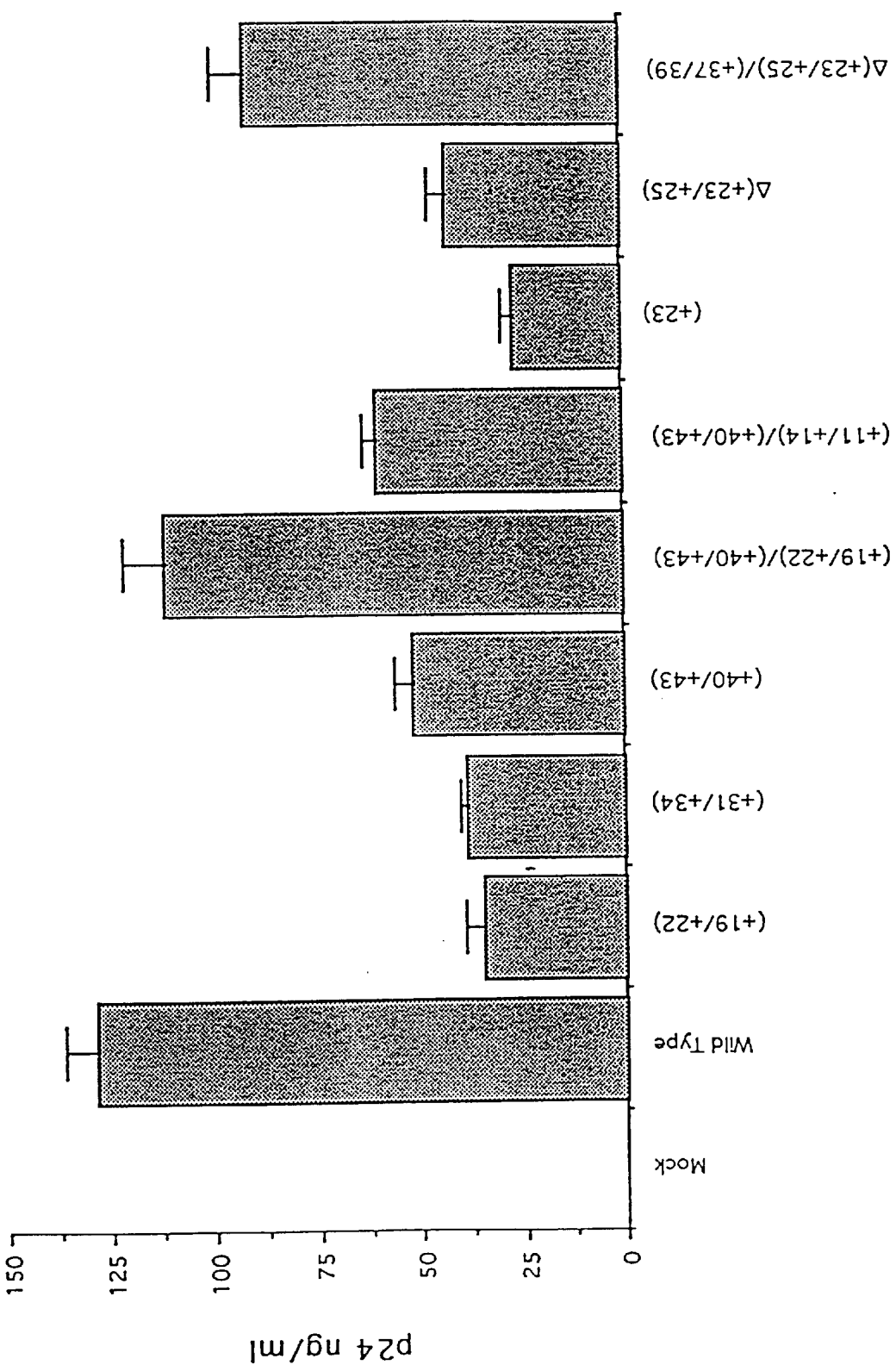
Figure 11B:
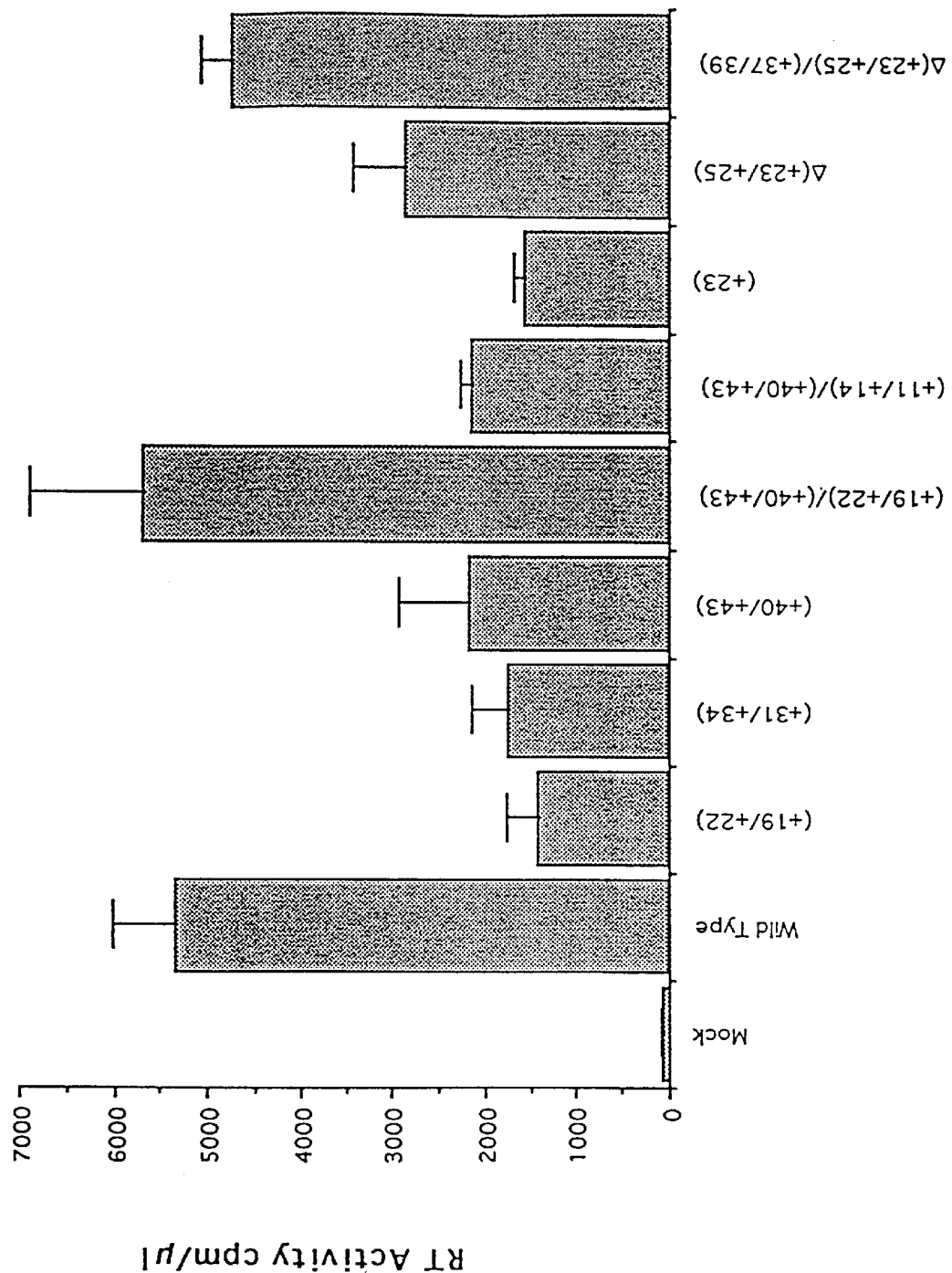

Supernatants from each of the 293 cell lines containing either wild-type or TAR mutant viruses were assayed for p24 antigen (Ag) and reverse transcriptase (RT) activity. The 293 isolates expressing TAR mutuant proviruses (+19/+22), (+31/+34), or (+23) produced 25–35 ng/ml of released p24 Ag, the cell lines expressing (+40/+43), (+11/+14)/(+40/+43), or Δ(+23/+25) produced 50 to 60 ng/ml, and cells expressing Δ(+23/+25)/(+37/+39), (+19/+22)/(+40/+43) or the wild-type virus produced 95 to 130 ng/ml of p24 Ag (FIG. 11A). The $^{32}$P-RT activity in the same culture supernatants ranged from $1.4 \times 10^6$ to $5.5 \times 10^6$ cpm/μl as indicated in FIG. 11B. The amounts of secreted p24 Ag correlated well with the RT activity such that a ratio of $^{32}$P-RT activity to p24 Ag was approximately 40–53 {(cpm/μl)/p24(ng/ml)}. Northern and Western blot analysis was also performed and confirmed the presence of viral specific RNAs and proteins. It was also critical to determine whether any DNA rearrangements occurred in the long terminal repeats of these proviruses. To confirm the integrity of the integrated provirus in each 293 cell line, PCR amplification was performed with specific oligonucleotide primer pairs corresponding to both the 5' and 3' LTRs. The primers amplified either a region extending from −436 to +242 which included the 5' LTR and the primer binding site or a region from +9146 to +9722 which included both the polypurine tract and the 3' LTR. Each primer pair produced the expected 678 bp and 576 bp DNA fragments respectively and the integrity of each mutation was confirmed by DNA sequence analysis of the PCR amplified fragments. Thus, 293 cell lines were obtained containing each of the TAR mutant proviruses shown in FIGS. 9A–9I.

EXAMPLE 14

HIV-1 TAR Mutant Viruses are Competent for Viral Entry and Reverse Transcription The present example demonstrates that TAR mutant viruses do not exhibit defects in their ability to either infect lymphocytes or to initiate reverse transcription. The present example also illustrates the utility of the present invention for providing efficient methods of providing stably infected cell lines, these cell lines being useful in turn in the production of enhanced quantities of mutant virus for vaccine preparation.

The T-lymphocyte cell lines H9 and Jurkat were infected with $1 \times 10^6$ $^{32}$P-RT cpm equivalents of either wild-type HIV-1 produced by 293 cells or with the HIV-1 isolates IIIb (Popovic et al., 1984) and SF-2 (Sanchez et al., 1985). There were no significant differences in the replication kinetics among these three viruses indicating that the neo gene did not alter viral replication properties. Next it was important to determine whether alterations in TAR structure affected the ability of viruses to infect T-lymphocytes or undergo reverse transcription. To directly test whether TAR mutations altered either viral cell entry or the initiation of reverse transcription, single cycle infections of Jurkat cells with wild-type and TAR mutant viruses were performed and analyzed by PCR. Jurkat cells were incubated with $2 \times 10^6$ $^{32}$P-RT cpm equivalents of wild-type or the TAR mutant viruses, (+19/+22), (+31/+34), (+40/+43), (+19/+22)/(+40/+43), (+11/+14)/(+40/+43) and Δ(+23/+25). As controls, Jurkat cells were incubated with either heat inactivated wild-type virus or supernatant from uninfected cells. After 2 hrs of infection at 37° C., the cells were washed three times and approximately 0.1 μg of total DNA from these cells was subjected to PCR analysis.

Figure 12A:
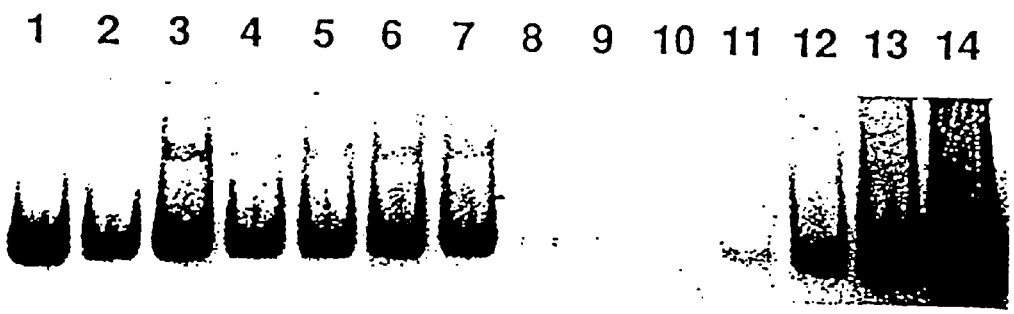
Figure 12B:
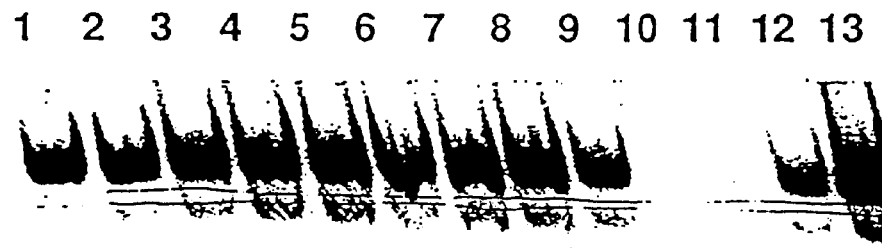

$^{32}$P labeled oligonucleotide primers (+44/+64, sense) and (+183/+159, antisense) complementary to the R and U5 regions of the HIV-1 LTR respectively should amplify a specific band of 139 base pairs. A species of the expected size was amplified from Jurkat cells infected with wild-type virus (FIG. 12A, lane 7). As shown in FIG. 12A, PCR amplification of DNA from Jurkat cells infected with the TAR mutants (+19/+22) (lane 1), (+31/+34) (lane 2), (+40/+43) (lane 3), (+19/+22)/(+40/+43) (lane 4), (+11/+14)/(+40/+43) (lane 5), (+23/+25) (lane 6) gave the same size species of comparable intensity. Heat inactivation of the wild-type virus reduced the signal approximately 50-fold (FIG. 12A, lane 8) and no species was detected in mock infected cells (FIG. 12A, lane 9). Since PCR is specific for DNA targets, each of the viruses likely have relatively equal ability to gain entry to the cell and initiate reverse transcription. Titration of a molecular HIV-1 provirus present at either 0, 10, $10^2$, $10^3$ or $10^4$ copies (FIG. 12A, lanes 10–14) demonstrated that the PCR reaction was linear and quantitative. Oligonucleotide primers specific to the first intron of the human β-globin gene, which amplify a specific 110 bp band, were included as a control for the amount of DNA in each PCR analysis. There were no significant differences in the intensity of this band among the different samples (FIG. 12B, lane 1–9). PCR amplification as shown in FIG. 12B for 0 μg (lane 10), $2 \times 10^{-3}$ μg (lane 11), $2 \times 10^{-2}$ μg (lane 12), and 0.2 μg (lane 13) of Jurkat chromosomal DNA normalized with herring sperm DNA demonstrated that the amplification reaction of the β-globin gene was linear and quantitative.

These results indicate that TAR mutant viruses do not exhibit defects in their ability to either infect lymphocytes or to initiate reverse transcription.

EXAMPLE 15

TAR Mutant Viruses are Defective for Replication in T-Lymphocyte Cell Lines The present example demonstrates that the constitutive expression of tat could not compensate for the deleterious effect of the mutant TAR viruses on HIV-1 gene expression in T-lymphocytes.

Figure 13A:
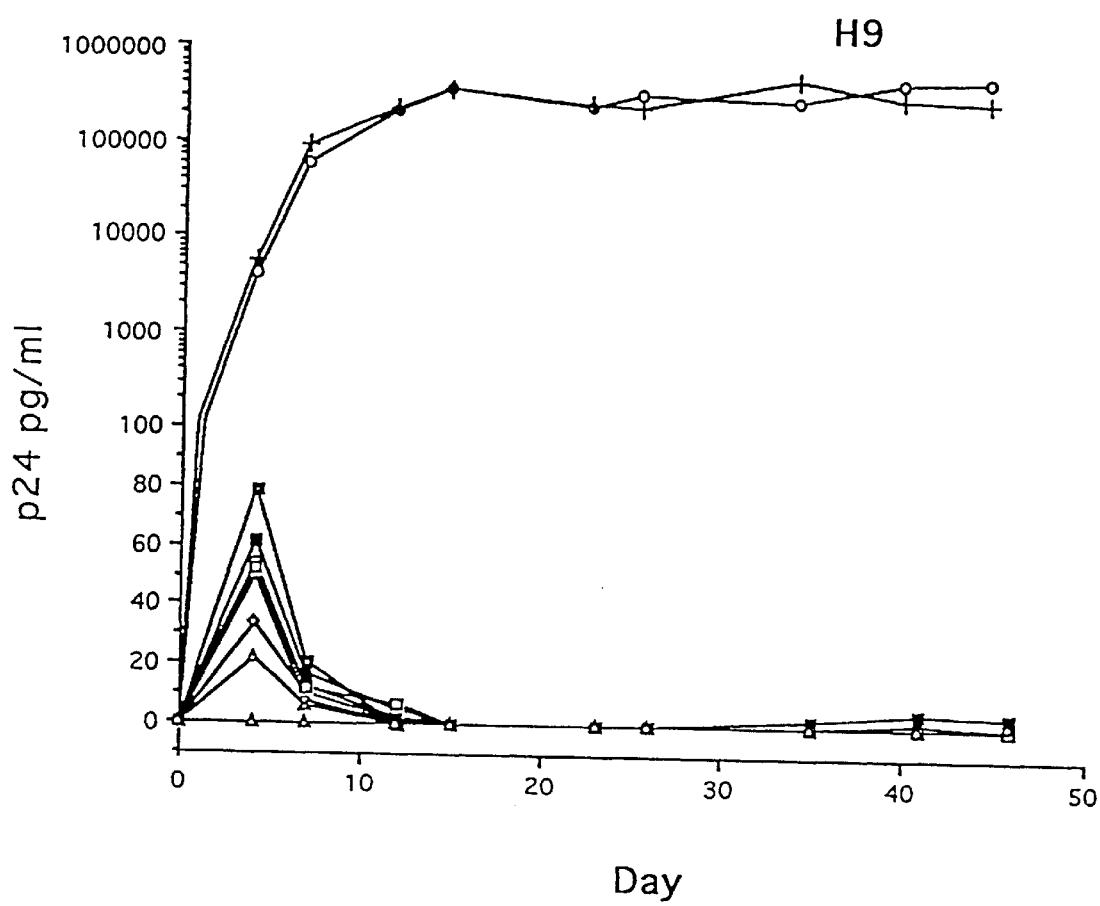
Figure 13B:
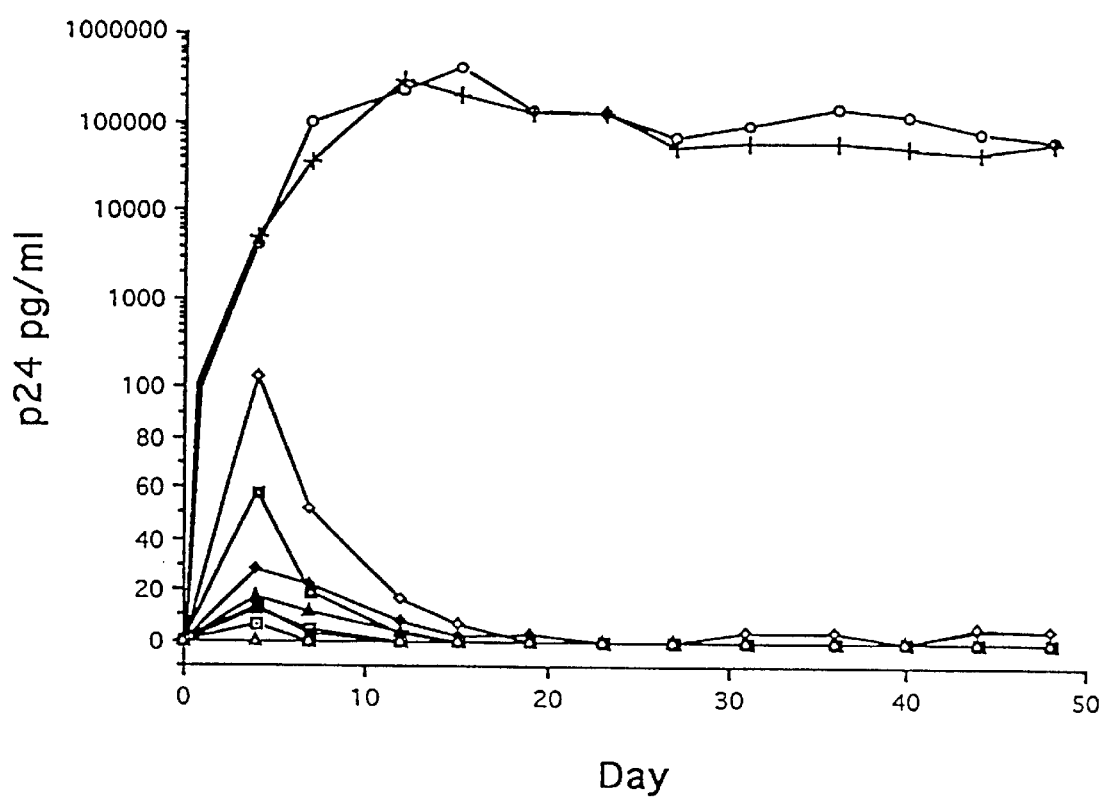

To determine if mutation of the TAR element influenced viral gene expression and growth kinetics, supernatants containing viruses produced from the cloned 293 cell lines were used to infect the T-lymphocyte cell lines H9 and Jurkat. Subsequent virus production was monitored by assays for the expression of both p24 Ag and RT activity. For each infection, $2 \times 10^6$ cells were infected with $1 \times 10^6$ $^{32}$P-RT cpm of either wild-type or TAR mutant viruses. The p24 Ag data showed that both the wild-type and the TAR stem restoration mutant virus, (+19/+22)/(+40/+43), replicated efficiently in H9 and Jurkat cell lines (FIG. 13A and 13B). The p24 expression increased rapidly over the first week and reached maximal expression in approximately 12–14 days. Cultures carried 48–50 days remained positive for p24 Ag (FIGS. 13A and 13B). In sharp contrast, infection of either H9 or Jurkat cells with TAR mutant viruses, (+19/+22), (+31/+43) (+40/+43), (+11/+14)/(+40/+43), (+23), Δ(+23/+25), Δ(+23/+25)/(+37/+39), produced a low, 20–100 pg/ml, transient release of p24 Ag after four days (FIGS. 13A and 13B). However the levels of p24 by day seven were two to four-fold lower ranging from 15–20 pg/ml and decreased markedly by ten days of infection. Jurkat cells infected with the TAR mutant (+23) which contains a point mutation in the bulge virus produced the largest burst of p24 Ag which was maintained for 14 days but decreased approximately two to three-fold after each passage. This data indicated that most of the HIV-1 TAR mutant viruses were capable of only transient expression of low levels of p24 Ag over a fifty day period of infection.

Figure 13C:
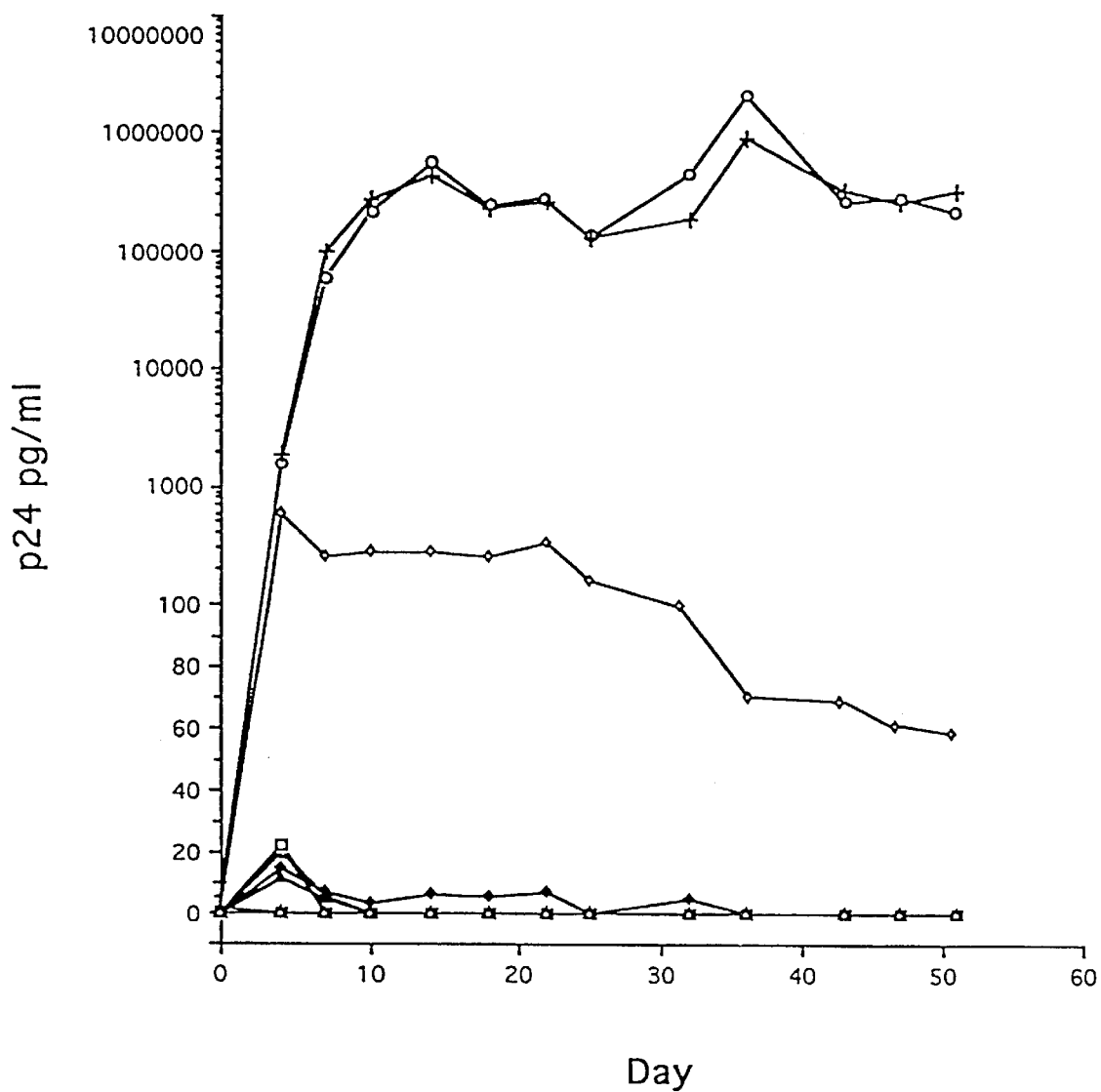

To test if the low levels of gene expression from the different TAR mutant viruses were due to the lack of expression of the tat protein, a Jurkat cell line constitutively expressing tat (Caputo et al., 1990) was infected with the same panel of viruses (FIG. 13C). As expected, the wild-type and TAR stem restoration mutant, (+19/+22)/(+40/+43), replicated with similar kinetics in these cells as with parental Jurkat cells. The maximal p24 Ag expression in this cell line was roughly two-fold higher than in the Jurkat cells lacking tat (1300 ng/ml, FIG. 13C, versus 600 ng/ml, FIG. 13B). However, the transient levels of p24 for several TAR mutant viruses on day four were four to five-fold lower than observed when these viruses were used to infect H9 or Jurkat cells (FIG. 13B and 13C). One mutant, Δ(+23/+25), produced no detectable transient burst, while another TAR mutant, (+40/+43), expressed marginally detectable p24 Ag (10–15 pg/ml) for 30 days. A virus harboring a point mutation in the bulge, (+23), expressed 600 pg/ml of p24 Ag by day 4 (50% of wild-type expression), but this expression decreased by ten-fold over 52 days. Similar results were seen using reverse transcription assays. This data demonstrated that the constitutive expression of tat could not compensate for the deleterious effect of these altered TAR structures on HIV-1 gene expression.

EXAMPLE 16

Growth Kinetics in Peripheral Blood Mononuclear Cells of HIV-1 TAR Mutant Viruses The present example provides data demonstrating that several of the mutant TAR viruses were able to replicate in activated peripheral blood mononuclear cells.

Previous data indicated that activation of T-lymphocyte proliferation markedly increased the gene expression of HIV-1 TAR mutants (Harrich et al., 1990). This effect was likely due to the stimulation of binding of NF-kB proteins to the HIV-1 enhancer (Harrich et al., 1990; Nabel et al., 1987). Thus, the present inventors assayed the growth properties of TAR mutant viruses on peripheral blood mononuclear cells (PBMCs) that were stimulated with PHA and IL-2. PBMCs were obtained from an HIV-1 seronegative donor and activated for three days in culture media supplemented with 1 $\mu$g/ml PHA. The cells were washed three times and $1\times10^6$ cells were infected with $1\times10^6$ $^{32}$P-RT units of either wild-type or TAR mutant viruses. The cells were infected for 2 hours, then washed three times with culture media and resuspended in complete media supplemented with 30 U/ml of IL-2 (Ross et al., 1991).

Figure 14:
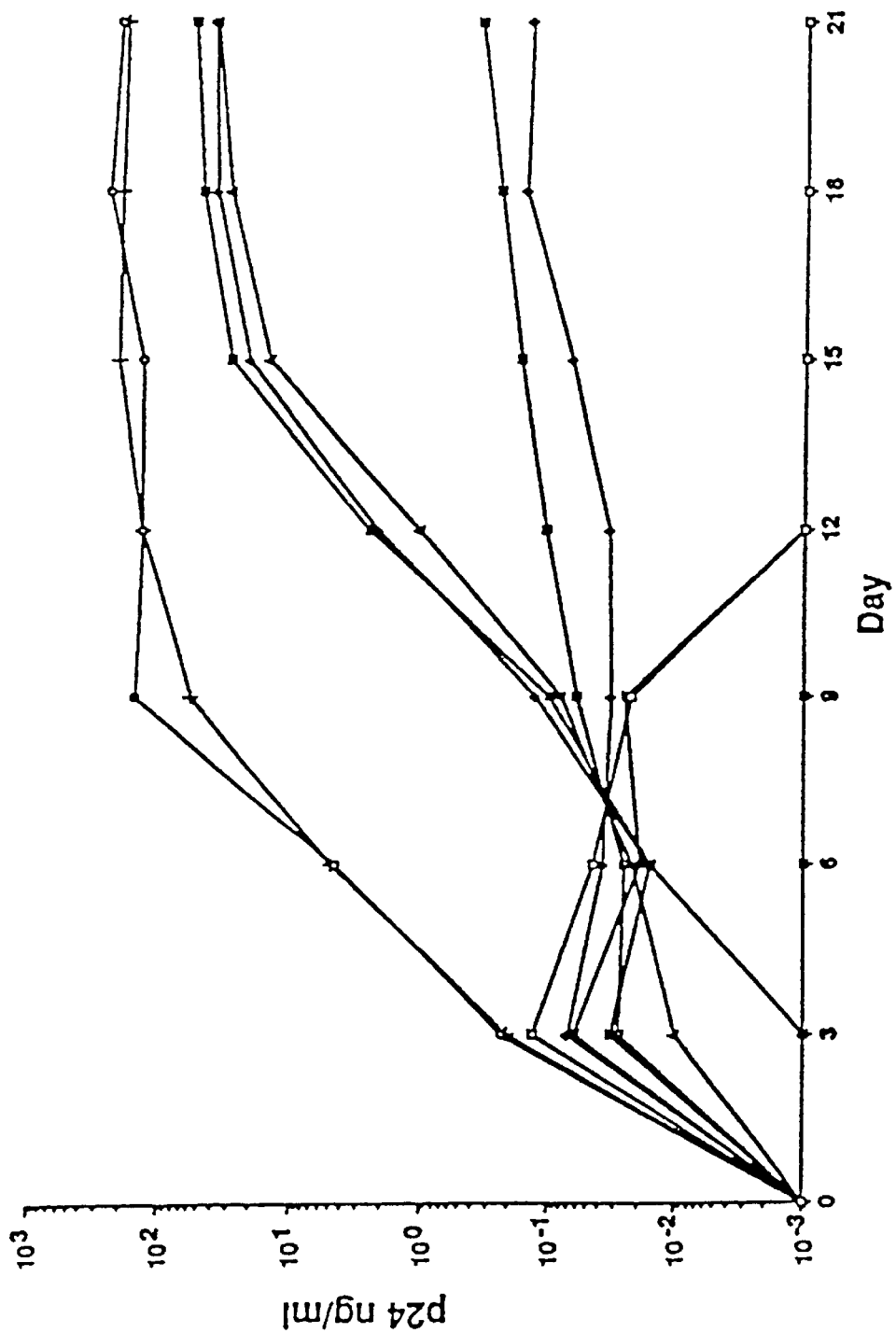

In contrast to the results found using T-cell lines, TAR mutant viruses displayed differential growth kinetics in activated PBMCs. As noted with T-lymphocyte cell lines, the virus containing the TAR stem-restoration mutant (+19/+23)/(+40/+43) replicated as well as wild-type virus (FIG. 14). However, viruses containing mutations that altered either the loop sequence, (+31/+34), the bulge sequence, (+23), or deleted the bulge altogether, Δ(+23/+25), displayed somewhat reduced growth kinetics and five to eight-fold decreases in p24 antigen by day 18 (FIG. 14). This was in contrast to the results seen with these viruses when infections were performed on T-lymphocyte cell lines where it was found that these viruses were much more defective (FIG. 13A–13C). Mutations that altered TAR RNA secondary structure, (+19/+23) and (+40/+43), produced 800 to 1400-fold less p24 Ag by day 18 than wild-type virus. Viruses containing mutations that disrupted the TAR RNA secondary structure, (+11/+14)/(+40/+43), or transposed the bulge to the opposite side of the TAR RNA stem, Δ(+23/+25)/(+37/+39), produced p24 Ag transiently, but it was not detectable (sensitivity threshold is 10 pg/ml) by day 18 (FIG. 14). Reverse transcriptase assays were also performed and though the levels for most of the TAR mutants were low as compared to wild-type, they correlated well with the amount of p24 Ag. These results indicate that several of the TAR mutants were not as defective for gene expression in stimulated PBMCs as compared to T-lymphocyte cell lines. However, several of the TAR mutants were unable to replicate in activated PBMCs indicating that TAR was critical for viral growth in these cells.

EXAMPLE 17

TAR Mutant Viruses Demonstrate Defective Transcription

Because viruses used in this study contained the neo gene, cells containing an integrated provirus could be resistant to the toxicity of G418. Even though significant levels of p24 Ag were not detected in Jurkat cells infected with different TAR mutant viruses, the present inventors tested whether it was possible to obtain populations of Jurkat cells containing the different TAR mutant viruses. G418 was added to aliquots of both HIV-1 infected and uninfected Jurkat cells at 28 days post-infection. Jurkat cells infected with either wild-type or each of the TAR mutant viruses were drug resistant in times ranging from two weeks for the wild-type and the TAR stem restoration mutant to four to five weeks for the other TAR mutants. No viable Jurkat cells were observed in the mock infected cultures treated with G418. Chromosomal DNA purified from these HIV-1 infected cells were subjected to PCR using the oligonucleotide primer pairs (−436/−415, sense) and (+242/+219, antisense) which were specific for the 5' LTR. The 678 bp DNA fragments generated by PCR for each of the HIV-1 isolates were subjected to DNA sequence analysis and in each case the correct TAR mutation was confirmed.

Figure 15A:
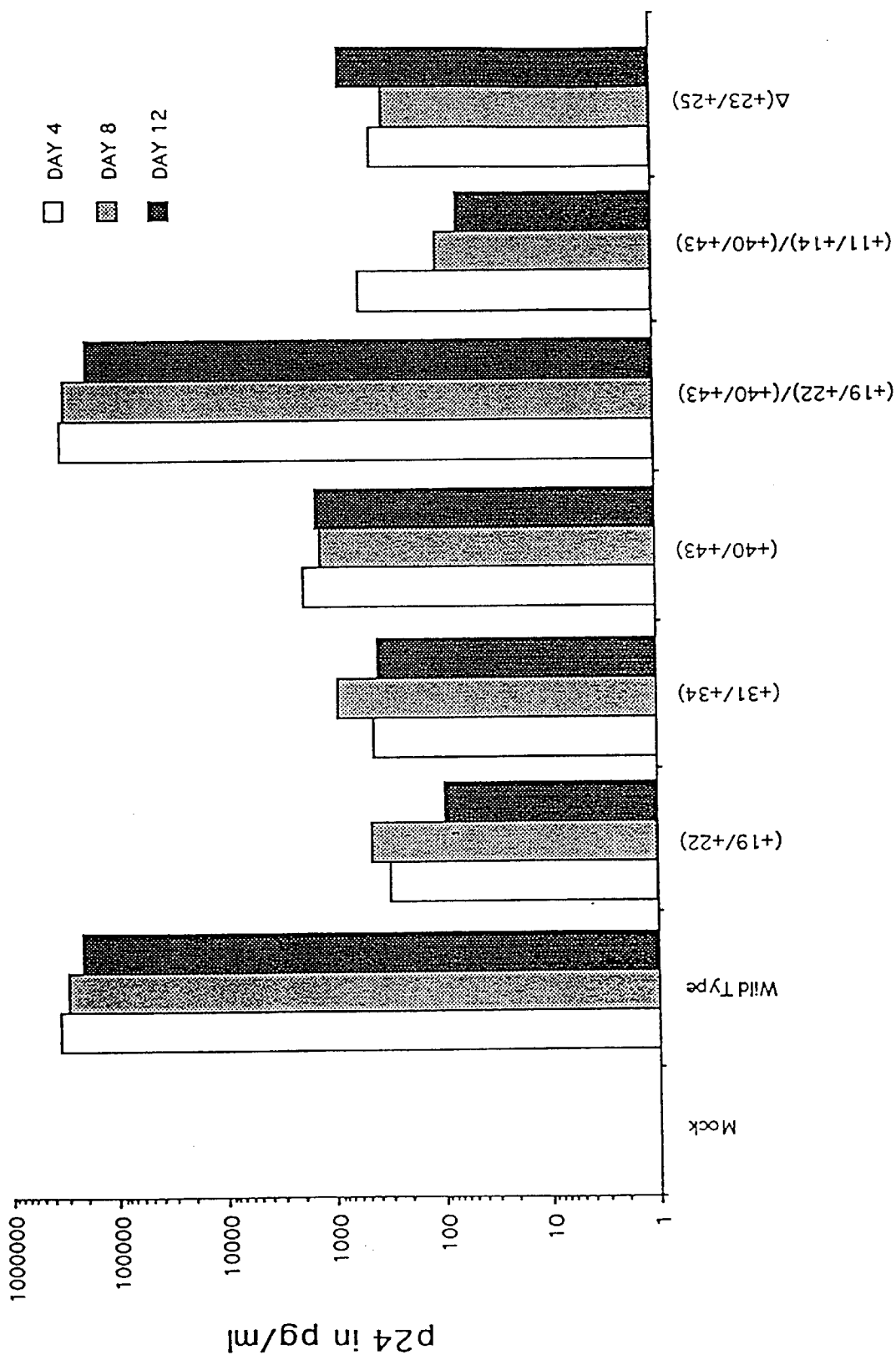

To assess the level of viral expression in these G418 selected Jurkat cell lines, the amounts of p24 Ag and RT detected in cell free supernatants from three consecutive passages of each cell line were determined (FIG. 15A and 15B). Jurkat cells infected with the wild-type or the TAR mutant viruses (+99/+22)/(+40/+43) produced 200–400 ng/ml p24 Ag, while Jurkat cells harboring other TAR mutant proviruses produced substantially less p24 Ag (FIG. 15A). The levels of p24 Ag in these different cells ranged from 100 to 500 pg/ml for (+19/+22), 400–900 pg/ml for (+31/+34), 1–2 ng/ml for (+40/+43), 70–600 pg/ml for (+11/+14)/(+40/+43), and 400–800 pg/ml for Δ(+23/+25) (FIG. 15A). The same viral supernatants were also assayed for RT activity (FIG. 15B). As expected, only supernatants from the wild-type or (+19/+22)/(+40/+43) had detectable RT activity (FIG. 15B). All other TAR mutant viruses including (+19/+22), (+31/+34), (+40/+43), (+11/+14)/(+40/+43), and Δ(+23/+25) produced no detectable RT activity.

These data indicate that while G418 selected Jurkat cells express low levels of HIV-1 specific antigens, they are unable to produce virus at detectable levels. Attempts by the inventor to infect a puromycin resistant H9 cell line by a co-culture with a Jurkat cell line stably infected with the (+11/+14)/(+40/+43) TAR mutant virus failed to produce an H9 cell line resistant to both puromycin and G418. This suggests that Jurkat cells infected with TAR mutant virus are not producing infectious HIV-1. Such a virus could comprise the foundation of a genetically attenuated live virus vaccine. An attractive addition to this vaccine would eliminate the integration process of HIV-1 TAR mutant virus by deleting the HIV-1 integrase gene from the genetic construct pBRHIV-neo and pBRHIV-puro.

Figure 16A:
Figure 16B:
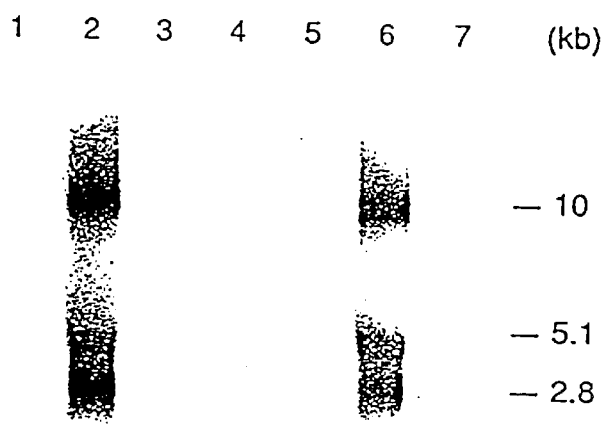
Figure 16C:
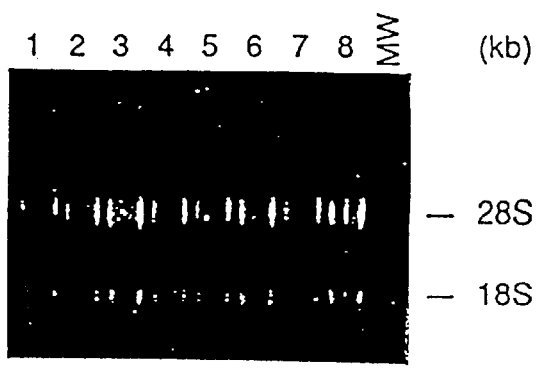

A Northern blot which contained 30 $\mu$g of total RNA isolated from each G418 selected Jurkat cell line was probed with an HIV-1 DNA fragment extending from nucleotides 8050 to 8385 to detect both spliced and unspliced HIV-1 RNA transcripts. The Northern blot in FIG. 16A showed a decrease in the steady state levels of RNA with the TAR mutant proviruses (+19/+22) (lane 3), (+31/+34) (lane 4), (+40/+43) (lane 5), (+11/+14)/(+40/+43) (lane 7), and Δ(+23/+25) (lane 8) compared to either the wild-type virus (lane 2) or the TAR mutant virus (+19/+22)/(+40/+43) (lane 6). An overnight exposure was sufficient to identify the 2.8 kb, 5.1 kb, and 10 kb RNA transcripts in Jurkat cells containing the wild-type or (+19/+22)/(+40/+43) proviruses (FIG. 16B) while a longer exposure was needed to detect these transcripts with the other TAR mutants (FIG. 16A). However, note that the 5.1 kb transcript was only faintly visible (FIG. 16A). HIV-1 transcripts were not detected in uninfected Jurkat cells (FIG. 16A and 16B, lane 1), nor were there significant differences in the amount of RNA loaded for these samples (FIG. 16C).

Figure 17:
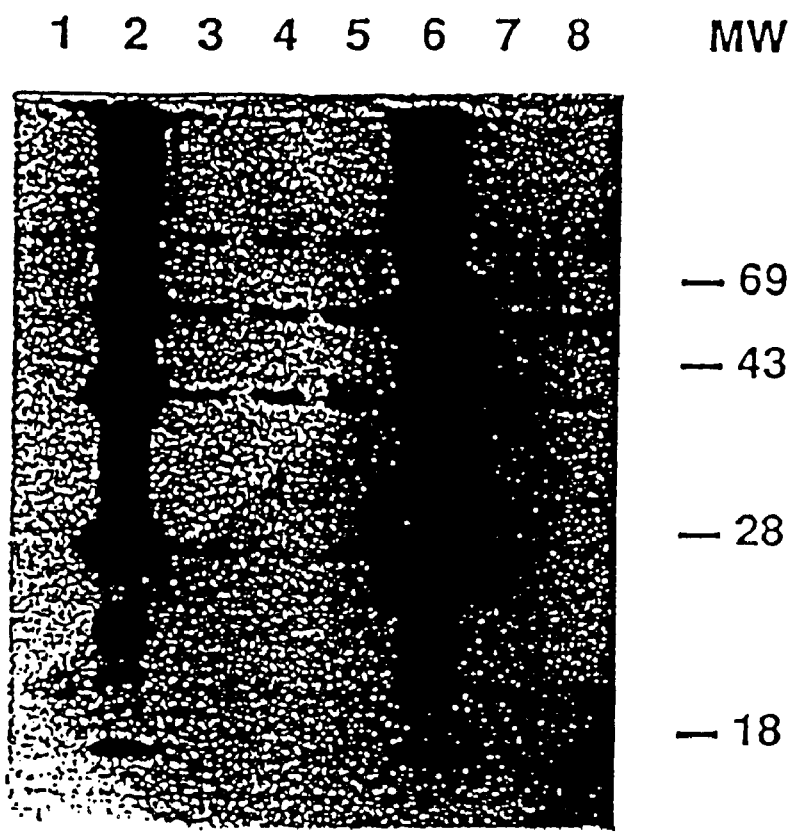

Whole cell lysates were prepared from each of the G418 selected Jurkat cell lines for Western blot analysis using purified human anti-HIV-1 IgG (FIG. 17). No proteins were detected in lysates made from uninfected Jurkat cells (FIG. 17, lane 1). Three predominant proteins of 55 kDa, 41 kDa, and 24 kDa were detected in lysates prepared from all HIV-1 infected Jurkat cells. As shown in FIG. 17, the TAR mutant proviruses (+19/+22) (lane 3), (+31/+34) (lane 4), (+40/+43) (lane 5), (+11/+14)/(+40/+43) (lane 7), and Δ(+23/+25) (lane 8) made substantially less of these proteins than either the wild-type (lane 2) or (+19/+22)/(+40/+43) viruses (lane 6). The level of viral proteins was consistent with the levels of steady state RNA detected for each proviral construct (FIG. 16A–16B).

Figure 18A:
Figure 18B:

One possible explanation for the decrease in the levels of viral RNA and protein in the G418 resistant Jurkat cells harboring TAR mutant viruses was that they contained a substantially lower proviral load than found in cells containing wild-type virus. PCR analysis of chromosomal DNA isolated from each of the Jurkat cell lines was performed using $^{32}$P labeled primer pairs (+44 to +64, sense) and (+183 to +159, antisense) that were specific to the R/U5 region of the HIV-1 LTR. No significant differences were observed in the level of the 139 bp specific band between the chromosomal DNA isolated from Jurkat cells containing the TAR mutant proviruses (+19/+22) (lane 1), (+31/+34) (lane 2), (+40/+43) (lane 3), (+11/+14)/(+40/+43) (lane 5) and Δ(+23/+25) (lane 6) as compared to (+19/+22)/(+40/+43) (lane 4) or the wild-type (lane 7) (FIG. 18A). Oligonucleotide primer pairs specific to the human β-globin gene, which generated a 100 base pair PCR product, were used as an internal control for the quantity of chromosomal DNA in each of the Jurkat cell lines. This primer pair demonstrated no significant differences (FIG. 18B). Thus the decrease in gene expression in Jurkat cells containing TAR mutant viruses was not due to differences in proviral copy number, but rather was due to a decreased level of transcription as the result of mutations in TAR.

EXAMPLE 18

Vector Delivery System for Transdominant tat Mutants

Mutant TAR viruses may be used with 293 cells to provide a delivery system for delivering transdominant tat mutant genes and the protein products encoded therein to a targeted host.

Two vector delivery systems are constructed that are capable of delivering transdominant tat and rev mutant genes. The first is a recombinant HIV-1 virus produced by a 293 cell line. To accomplish this, the Rous sarcoma virus LTR was inserted into the HIV-1 genome directly preceding the tat gene. This promoter can express the tat, env, rev, and puromycin resistance genes. This vector contains an HIV-1 LTR containing a TAR mutation such as (+11/+14)/(+40/+43) or (+30/+34) to limit gene expression directed by the HIV-1 LTR. Additional mutations in the HIV-1 LTR SP1, NFκB, or TATA regulatory elements could further reduce basal gene expression from the HIV-1 LTR. When 293 cells were transfected with this construct, 293 cell lines producing HIV-1 recombinant virus were obtained. This vector is unique in that it can express both transdominant tat and rev from a single vector. The second vector delivery system, similarly, expresses transdominant Tat and Rev protein along with the puromycin resistance gene, but not HIV-1env gene. To accomplish this, a 293 cell line which expresses HIV-1 gag, pol, and env was constructed. This cell line cannot produce HIV-1 virus.

EXAMPLE 19

Defective HIV-1 Constructs for Live Attenuated Vaccines

The present example is provided to demonstrate the utility of the claimed infected HIV cell lines, and particularly the enhanced amount of virus that they produce for the preparation of attenuated vaccines for treatment of viral disease, particularly for the treatment of HIV and diseases caused by this virus.

293 cells can produce substantial quantities of HIV-1 TAR mutant viruses. Small scale preparations have produced as much as 150 ng/ml of p24 in 12–16 hours. The production of HIV-1 TAR mutant viruses by 293 cell lines could be adapted for large scale production by either hollow fiber constant flow culturing or by spinner cell technology. HIV-1 TAR mutant virus could be separated from the culture supernatant by either centrifugation or two step gel-filtration column chromatography. The genetically attenuated live virus could be resuspended in the appropriate pharmacological buffers and adjuvant and used as vaccine.

The previous examples have demonstrated that an HIV-1 virus has been constructed that expresses transdominant Tat protein. This vector contains a wild type HIV-1 LTR and a transdominant tat gene. This virus can be produced in the 293 cell line expressing the activating proteins E1a and E1b. This virus can infect CD4+ human lymphocytes but can not replicate due to the inability of the transdominant tat gene to activate HIV-1 gene expression. If human lymphocytes previously infected with the inhibitory virus where later to be infected with a wild-type HIV-1 virus, a negative feedback loop would be established in which the wild-type Tat would activate the inhibitory virus expressing the transdominant Tat protein. This protein would then act to inhibit the replication of the wild type virus.

A further example of an attenuated virus for a vaccine would utilize an internal promoter incorporated into a TAR mutant virus. Specifically, the Rous sarcoma virus LTR is inserted into the HIV-1 genome just upstream of the tat gene. This promoter can constitutively express the transdominant tat gene. The HIV-1 LTR of this virus contains TAR mutations which would limit HIV-1 LTR directed gene expression. The TAR mutant viruses produced in 293 cells could be used to infect CD4+ human lymphocytes. Because this virus contains TAR mutations in the HIV-1 LTR as well as a transdominant tat gene, it is not able to replicate. In this system, constitutive expression of the transdominant tat gene would inhibit wild type HIV-1 virus replication in these cells.

BIBLIOGRAPHY

The following references are specifically incorporated herein by reference for the purposes indicated.

Barry, P. A. et al. 1991. *J. Virol.* 65:1392–1399.
Beck, E. et al. 1982. *Gene* 19:327–336.
Berkhout, B. et al. 1992. *J. Virol.* 66:139–149.
Berkhout, B. et al. 1990. *Cell* 62:757–767.
Berkhout B. et al., (1989a) *J. Virol.,* 63:5501–5504.
Berkhout B. et al. (1989b) *Cell,* 59:273–282.
Brake D. A. et al. (1990) *J. Virol.,* 64:962–965.
Calnan B. J. et al. (1991) *Genes Dev.,* 5:201–210.
Caputo, A. et al. 1990. *Acq. Imm. Defic.* 3:372–377.
Cordingley, M. G. et al. 1990. *Proc. Natl. Acad. Sci. USA* 87:8985–8989.
Dayton A. I. et al. (1986) *Cell,* 44:941–947.
Dingwall C. et al. (1990) *EMBO J,* 9:4145–4153.
Dingwall, C. et al. 1989. *Proc. Natl. Acad. Sci. USA* 86:6925–6929.
Elroy-Stein, O. et al. (1989) *Proc. Natl. Acad. Sci. USA,* 86:6126–6130.
Feinberg, M. B. et al. 1986. *Cell* 46:807–817.
Feineberg, M. B. et al. 1991. *Proc. Natl. Acad. Sci. USA* 88:4045–4049.

Feng S. and Holland E. C. (1988) *Nature,* 334:165–167.
Field, J. et al. (1988) *Mol. Cell, Biol.,* 8:2159–2169.
Fisher A. G. et al. (1986) *Nature,* 320:367–371.
Frankel A. D. et al. (1988) *Science,* 240:70–73.
Friedman, A. D. et al. (1988) *Nature,* 335:452–454.
Garcia J. A. et al. (1988) *EMBO J,* 7:3143–3147.
Garcia, J. A. et al. 1987. *EMBO J.* 6:3761–3770.
Garcia J. A. et al. (1989) *EMBO J,* 8:765–778.
Gatignol, A. et al. 1991. *Science* 251:1597–1600.
Gaynor, R. 1992. *AIDS* 6:347–363.
Gentz, R., Chen, C. H. and Rosen, C. A. *Proc. Natl. Acad. Sci. USA,* 86:821–824.
Glen G. M. and Ricciardi R. P. (1987) *Mol Cell Biol,* 7:1004–1010.
Gorman C. M. et al. (1982) *Mol Cel Biol,* 2:1044–1051.
Graeble, M. A. et al. 1993. *Proc. Natl. Acad. Sci. USA* 90:6184–6188.
Graham, F. L. et al. 1977. *J. Gen. Virol.* 36:59–72.
Harrich, D. et al. 1989. *J. Virol.* 63:2585–2591.
Harrich D. et al. (1990) *EMBO J,* 9:4417–4424.
Hauber J. et al. (1987) *Proc Natl Acad Sci. USA,* 84:6364–6368.
Hauber, J. and Cullen, B. R. 1988. *J. Virol.* 62:673–679.
Hauber J. et al. (1989) *J. Virol,* 63:1181–1187.
Jakobovits, A. et al. 1988. *Mol. Cell. Biol.* 8:2555–2561.
Jones K. A. et al. (1986) *Science* 232:755–759.
Jones, K. A. et al. 1988. *Genes & Dev.* 2:1101–1114.
Kao, S. Y. et al. 1987. *Nature* 330:489–493.
Kato, H. et al. 1991. *Science* 251:1476–1479.
Kim, S. Y. et al. 1989. *J. Virol.* 63:3708–3713.
Kliewer, S. J. et al. 1989. *J. Virol.* 63:4616–4625.
Laspia, M. F. et al. 1990. *Genes & Dev.* 4:2397–2408.
Laspia, M. F. et al. 1989. *Cell* 59:283–292.
Leonard J. et al. 1989. *J. Virol.* 63:4919–4924.
Lu, X. et al. 1993. *J. Virol.* 67:1752–1760.
Lu, Y. et al. 1989. *J. Virol.* 63:4115–4119.
Malim et al. (1989) *Cell,* 58:205–214.
Mann, D. A. and Frankel, A. D. (1991) *EMBO J.,* 10:1733–1739.
Marciniak R. A. et al. (1990) *Cell,* 63:791–802.
Marciniak, R. A. and Sharp, P. A. 1991. *EMBO J.* 10:4189–4196.
Modesti, N. et al. (1991) *New Biol.,* 3:759–768.
Morganstern, J. P. and Land, H. (1990) *Nucl. Acids Res.,* 18:3587–3596.
Muesing, M. A. et al. 1987. *Cell* 48:691–701.
Nabel, G. J. et al. 1988. *Science* 239:1299–1300.
Nabel G. and Baltimore D. (1987) *Nature,* 326:711–713.
Okamoto, T. and Wong-Staal, F. 1986. *Cell* 47:29–35.
Olsen, H. S. and Rosen, C. A. 1992 *J. Virol.* 66:5594–5597.
Parrot, C. et al. 1991. *J. Virol.* 65:1414–1419.
Pearson, L. et al. (1990) *Proc. Natl. Acad. Sci., USA,* 87:5079–5083.
Peterlin, B. M. et al. 1986. *Proc. Natl. Acad. Sci. USA* 83:734–9738.
Popovic,M. et al. 1984. *Science* 224:497–500.
Potts, B. 1990. In: Techniques in HIV Research; ed. Aldovini, A. and Walker, B. D. Stockton Press.
Rappaport J. et al. (1989) *New Biol.,* 1:101:110.
Ratnasabapathy, R. et al. 1990. *Genes & Dev.* 4:2061–2074.
Remmingtons Pharmaceutical Science (1990) 18th edition, Mack Publishing Company, Easton, Pa., A. Gennaro, editor.
Rice A. P. and Carlotti F. (1990) *J. Virol.,* 64:1864–1868.
Rosen C. A. et al. (1985) *Cell,* 41:813:823.
Rosen, C. A. et al. 1985. *Proc. Natl. Acad. Sci. USA* 82:6502–6506.
Ross, E. K. et al. 1991. *J. Virol.* 65:4350–4358.
Roy S. et al. (1990b) *Genes. Dev;* 4:1365–1373.
Roy S. et al. (1990a) *J. Virol.,* 64:1402–1406.
Ruben S. et al. (1989) *J. Virol.,* 63:1–8.
Sadaie M. R. et al. (1988) *Science,* 239:910–913.
Sanchez, P. R. et al. 1985. *Science* 227:484–492.
Selby M. J. et al. (1989) *Genes Dev.,* 3:547–558.
Selby M. J. and Peterlin B. M. (1990) *Cell,* 62:769–776.
Sheldon, M. R. et al. 1993. *Mol. Cell. Biol.* 13:1251–1263.
Sheline, C. T. et al. 1991. *Genes & Dev.* 5:2508–2520.
Siomi H. et al. (1990) *J. Virol.,* 64:1803–1807.
Sodroski J. et al. (1985) *Science,* 227:171–173.
Templeton, D. (1992) *Mol. Cell. Biol.,* 12:435–443.
Terwilliger, E. et al. 1986. *J. Virol.* 60:754–760.
Trono D. et al. (1989) *Cell,* 59:113–120.
Wachsman W. et al. (1987) *Science,* 235:674–677.
Weeks, K. M. et al. (1990) *Science,* 249:1281–1285.
Weeks, K. M. and Crothers, D. M. 1991. *Cell* 66:577–588.
Weiss, A. L. et al. 1984. *J. Immunol.* 133:123–128.
Wright C. M. et al. (1986) *Science,* 234:988–992.
Wu, F. et al. 1991. *Genes & Dev.* 5:2128–2140.
Wu, F. K. et al. 1988. *EMBO J.* 7:2117–2130.
Wu, F. et al. (1991) *Genes Dev.,* 5:2128–2140.
York-Higgins, D. et al. 1990. *J. Virol.* 64:4016–4020.
Zack, J. A. et al. 1990. *Cell* 61:213–222.

---

What is claimed is:

1. A 293 cell line that produces wild-type levels of HIV TAR mutant virus in the presence of a transactivator protein, said cell line being infected with a mutant HIV TAR virus having a mutation in the loop sequence on the bulge sequence.

2. The HIV TAR mutant virus of claim 1 wherein the mutation in the loop sequence is a mutant +31/+34.

3. The HIV TAR mutant virus of claim 1 wherein the mutation in the bulge sequence is +23 or (+23/+25).

4. The 293 cell line of claim 1 wherein the HIV TAR mutant virus is +19/+22, +31/+34, +23, +40/+43, (+11/+14)/(+40/+43), +23/+25, (+23/+25)/(+37/+39), or (+19/+22)/(+40/+43).

5. The 293 cell line of claim 1 wherein the transactivator protein is an adenovirus transactivator E1A protein.

6. The 293 cell line of claim 1 wherein the transactivator protein is an adenovirus transactivator E1A and E1B protein.

7. The 293 cell line of claim 1 wherein the HIV TAR mutant virus is (+11/+14)/(+40/+43).

8. A method of producing HIV TAR mutant viruses in a stably infected 293 cell line comprising:

transfecting a 293 cell line producing a transactivator protein with a HIV virus harboring an HIV-1 TAR mutation in the loop sequence on the bulge sequence to provide a stably HIV TAR mutant infected 293 cell line; and collecting the HIV TAR mutant viruses produced by the stably infected 293 cell line, wherein the stably infected 293 cell line produces elevated levels of HIV TAR mutant virus in the presence of transactivator protein relative to levels of TAR mutant virus produced in the absence of transactivator protein.

9. The method of claim 8 where the mutation in the loop sequence is mutant +31/+34.

10. The method of claim 8 where the mutation in the bulge sequence is +23 or (+23/+25).

11. The method of claim 8 wherein the HIV-1 TAR mutant virus is +19/+22, +31/+34, +23, +40/+43, (+11/+14)/(+40/+43), ▲(+23/+25), ▲(+23/+25)/(+37/+39), or (+19/+22)/(+40/+43).

12. A composition comprising a HIV TAR mutant virus selected from the group consisting of (+19/+22), +31/+34, +23, (+40/+43), (+11/+14)/(+40/+43), ▲(+23/+25), ▲(+23/+25)/(+37/+39), or (+19/+22)/(+40/+43).

* * * * *

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
      (A) LENGTH:     219 base pairs
      (B) TYPE:       nucleic acid
      (C) STRANDEDNESS: single
      (D) TOPOLOGY:   linear (ii) MOLECULE TYPE: DNA (genomic)

(xi) SEQUENCE DESCRIPTION: SEQ ID NO:1:

```
ATG GAG CCA GTA GAT CCT AAT CTA GAG CCC TGG AAG CAT CCA            42
Met Glu Pro Val Asp Pro Asn Leu Glu Pro Trp Lys His Pro
```

```
     -1    1                   5                        10
GGA  AGT  CAG  CCT  AGG  ACT  GCT  TGT  AAC  AAT  TGC  TAT  TGT  AAA          84
Gly  Ser  Gln  Pro  Arg  Thr  Ala  Cys  Asn  Asn  Cys  Tyr  Cys  Lys
          15                  20                       25

AAG  TGT  TGC  TTT  CAT  TGC  TAC  GCG  TGT  TTC  ACA  AGA  AAA  GGC         126
Lys  Cys  Cys  Phe  His  Cys  Tyr  Ala  Cys  Phe  Thr  Arg  Lys  Gly
               30                       35                      40

TTA  GGC  ATC  TCC  TAT  GGC  AGG  AAG  AAG  GGG  GGA  GCC  GGC  GGA         168
Leu  Gly  Ile  Ser  Tyr  Gly  Arg  Lys  Lys  Gly  Gly  Ala  Gly  Gly
                    45                       50                      55

GGA  GCT  CCT  CAG  GAC  AGT  CAG  ACT  CAT  CAA  GCT  TCT  CTA  TCA         210
Gly  Ala  Pro  Gln  Asp  Ser  Gln  Thr  His  Gln  Ala  Ser  Leu  Ser
                         60                       65

AAG  CAG  TAA                                                                219
Lys  Gln
70
```

(2) INFORMATION FOR SEQ ID NO:2:

(i) SEQUENCE CHARACTERISTICS:
        (A) LENGTH:       219 base pairs
        (B) TYPE:         nucleic acid
        (C) STRANDEDNESS:  single
        (D) TOPOLOGY:     linear (ii) MOLECULE TYPE: DNA (genomic)

(xi) SEQUENCE DESCRIPTION: SEQ ID NO:2:

```
ATG  GAG  CCA  GTA  GAT  CCT  AAT  CTA  GAG  CCC  TGG  AAG  CAT  CCA          42
Met  Glu  Pro  Val  Asp  Pro  Asn  Leu  Glu  Pro  Trp  Lys  His  Pro
-1    1                   5                        10

GGA  AGT  CAG  CCT  AGG  ACT  GCT  TGT  AAC  AAT  TGC  TAT  TGT  AAA          84
Gly  Ser  Gln  Pro  Arg  Thr  Ala  Cys  Asn  Asn  Cys  Tyr  Cys  Lys
          15                  20                       25

AAG  TGT  TGC  TTT  CAT  TGC  TAC  GCG  TGT  TTC  ACA  AGA  AAA  GGC         126
Lys  Cys  Cys  Phe  His  Cys  Tyr  Ala  Cys  Phe  Thr  Arg  Lys  Gly
               35                       40                      45

TTA  GGC  ATC  TCC  TAT  GGC  AGG  AAG  AAG  CGG  AGA  CAG  CGA  CGA         168
Leu  Gly  Ile  Ser  Tyr  Gly  Arg  Lys  Lys  Arg  Arg  Gln  Arg  Arg
                    50                       55                      60

AGA  GCT  CCT  CAG  GAC  AGT  CAG  ACT  CAT  CAA  GCT  TCT  CTA  TCA         210
Arg  Ala  Pro  Gln  Asp  Ser  Gln  Thr  His  Gln  Ala  Ser  Leu  Ser
                         65                       70

AAG  CAG  TAA                                                                219
Lys  Gln
75
```

(2) INFORMATION FOR SEQ ID NO:3:

(i) SEQUENCE CHARACTERISTICS:
        (A) LENGTH:       219 base pairs
        (B) TYPE:         nucleic acid
        (C) STRANDEDNESS:  single
        (D) TOPOLOGY:     linear (ii) MOLECULE TYPE: DNA (genomic)

(xi) SEQUENCE DESCRIPTION: SEQ ID NO:3:

```
ATG  GAG  CCA  GTA  GAT  CCT  AAT  CTA  GAG  CCC  TGG  AAG  CAT  CCA          42
Met  Glu  Pro  Val  Asp  Pro  Asn  Leu  Glu  Pro  Trp  Lys  His  Pro
-1    1                   5                        10

GGA  AGT  CAG  CCT  AGG  ACT  GCT  TGT  AAC  AAT  TGC  TAT  TGT  AAA          84
Gly  Ser  Gln  Pro  Arg  Thr  Ala  Cys  Asn  Asn  Cys  Tyr  Cys  Lys
          15                  20                       25
```

```
AAG TGT TGC TTT CAT TGC TAC GCG TGT TTC ACA AGA AAA GGC        126
Lys Cys Cys Phe His Cys Tyr Ala Cys Phe Thr Arg Lys Gly
         30                  35                  40

TTA GGC ATC TCC TAT GGC AGG AAG AAG CGG AGA GCC GGC GGA        168
Leu Gly Ile Ser Tyr Gly Arg Lys Lys Arg Arg Ala Gly Gly
             45                  50                  55

GGA GCT CCT CAG GAC AGT CAG ACT CAT CAA GCT TCT CTA TCA        210
Gly Ala Pro Gln Asp Ser Gln Thr His Gln Ala Ser Leu Ser
                 60                  65

AAG CAG TAA                                                    219
Lys Gln
70
```

(2) INFORMATION FOR SEQ ID NO:4:

(i) SEQUENCE CHARACTERISTICS:
        (A) LENGTH:      6 amino acid residues
        (B) TYPE:        amino acid
        (D) TOPOLOGY:    linear (ii) MOLECULE TYPE: Peptide (xi) SEQUENCE DESCRIPTION: SEQ ID NO:4:

```
Gly Gly Ala Gly Gly Gly
1               5
```

(2) INFORMATION FOR SEQ ID NO:5:

(i) SEQUENCE CHARACTERISTICS:
        (A) LENGTH:      219 base pairs
        (B) TYPE:        nucleic acid
        (C) STRANDEDNESS: single
        (D) TOPOLOGY:    linear (ii) MOLECULE TYPE: Peptide (xi) SEQUENCE DESCRIPTION: SEQ ID NO:5:

```
ATG GAG CCA GTA GAT CCT AAT CTA GAG CCC TGG AAG CAT CCA         42
Met Glu Pro Val Asp Pro Asn Leu Glu Pro Trp Lys His Pro
 -1  1               5                  10

GGA AGT CAG CCT AGG ACT GCT TGT AAC AAT TGC TAT TGT AAA         84
Gly Ser Gln Pro Arg Thr Ala Cys Asn Asn Cys Tyr Cys Lys
     15                  20                  25

AAG TGT TGC TTT CAT TGC TAC GCG TGT TTC ACA AGA AAA GGC        126
Lys Cys Cys Phe His Cys Tyr Ala Cys Phe Thr Arg Lys Gly
         35                  40                  45

TTA GGC ATC TCC TAT GGC AGG AAG AAG CGG AGA CAG GGA GCC        168
Leu Gly Ile Ser Tyr Gly Arg Lys Lys Arg Arg Gln Gly Ala
             50                  55                  60

GGC GGT CCT CAG GAC AGT CAG ACT CAT CAA GCT TCT CTA TCA        210
Gly Gly Pro Gln Asp Ser Gln Thr His Gln Ala Ser Leu Ser
                 65                  70

AAG CAG TAA                                                    219
Lys Gln
75
```

(2) INFORMATION FOR SEQ ID NO:6:

(i) SEQUENCE CHARACTERISTICS:
        (A) LENGTH:      4 amino acid residues
        (B) TYPE:        amino acid
        (D) TOPOLOGY:    linear (ii) MOLECULE TYPE: Peptide (xi) SEQUENCE DESCRIPTION: SEQ ID NO:6:

```
Ala Gly Gly Gly
 1

(2) INFORMATION FOR SEQ ID NO:7:

(i) SEQUENCE CHARACTERISTICS:
          (A) LENGTH:       4 amino acid residues
          (B) TYPE:         amino acid
          (D) TOPOLOGY:     linear (ii) MOLECULE TYPE: Peptide (xi) SEQUENCE DESCRIPTION: SEQ ID NO:7:

Gly Ala Gly Gly
 1

(2) INFORMATION FOR SEQ ID NO:8:

(i) SEQUENCE CHARACTERISTICS:
          (A) LENGTH:       6 amino acid residues
          (B) TYPE:         amino acid
          (D) TOPOLOGY:     linear (ii) MOLECULE TYPE: Peptide (xi) SEQUENCE DESCRIPTION: SEQ ID NO:8:

Arg Arg Gln Arg Arg Arg
 1               5

(2) INFORMATION FOR SEQ ID NO:9:

(i) SEQUENCE CHARACTERISTICS:
          (A) LENGTH:       18 base pairs
          (B) TYPE:         nucleic acid
          (C) STRANDEDNESS: single
          (D) TOPOLOGY:     linear (ii) MOLECULE TYPE: DNA (Genomic)

(xi) SEQUENCE DESCRIPTION: SEQ ID NO:9:

GGGGGAGCCG GCGGAGGA                                              18

(2) INFORMATION FOR SEQ ID NO:10:

(i) SEQUENCE CHARACTERISTICS:
          (A) LENGTH:       4 amino acid residues
          (B) TYPE:         amino acid
          (D) TOPOLOGY:     linear (ii) MOLECULE TYPE: Peptide (xi) SEQUENCE DESCRIPTION: SEQ ID NO:10:

Gln Arg Arg Arg
 1

(2) INFORMATION FOR SEQ ID NO:11:

(i) SEQUENCE CHARACTERISTICS:
          (A) LENGTH:       12 base pairs
          (B) TYPE:         nucleic acid
          (C) STRANDEDNESS: single
          (D) TOPOLOGY:     linear (ii) MOLECULE TYPE: DNA (Genomic)

(xi) SEQUENCE DESCRIPTION: SEQ ID NO:11:

GCCGGCGGAG GA                                                    12

(2) INFORMATION FOR SEQ ID NO:12:
```

```
      (i) SEQUENCE CHARACTERISTICS:
           (A) LENGTH:         4 amino acid residues
           (B) TYPE:           amino acid
           (D) TOPOLOGY:       linear (ii) MOLECULE TYPE: Peptide (xi) SEQUENCE DESCRIPTION: SEQ ID NO:12:

Arg Arg Arg Ala
1

(2) INFORMATION FOR SEQ ID NO:13:

(i) SEQUENCE CHARACTERISTICS:
           (A) LENGTH:         12 base pairs
           (B) TYPE:           nucleic acid
           (C) STRANDEDNESS:   single
           (D) TOPOLOGY:       linear (ii) MOLECULE TYPE: DNA (Genomic)

(xi) SEQUENCE DESCRIPTION: SEQ ID NO:13:

GGAGCCGGCG GT                                                         12

(2) INFORMATION FOR SEQ ID NO:14:

(i) SEQUENCE CHARACTERISTICS:
           (A) LENGTH:         15 amino acid residues
           (B) TYPE:           amino acid
           (D) TOPOLOGY:       linear (ii) MOLECULE TYPE: Peptide (xi) SEQUENCE DESCRIPTION: SEQ ID NO:14:

Met Tyr Phe Tyr Asp Val Pro Asp Tyr Ala Ser Leu Gly Gly Pro
1               5                   10                  15

(2) INFORMATION FOR SEQ ID NO:15:

(i) SEQUENCE CHARACTERISTICS:
           (A) LENGTH:         11 base pairs
           (B) TYPE:           nucleic acid
           (C) STRANDEDNESS:   single
           (D) TOPOLOGY:       linear (ii) MOLECULE TYPE: DNA (Genomic)

(xi) SEQUENCE DESCRIPTION: SEQ ID NO:15:

AAGATGGGTG G                                                          11

(2) INFORMATION FOR SEQ ID NO:16:

(i) SEQUENCE CHARACTERISTICS:
           (A) LENGTH:         11 base pairs
           (B) TYPE:           nucleic acid
           (C) STRANDEDNESS:   single
           (D) TOPOLOGY:       linear (ii) MOLECULE TYPE: DNA (Genomic)

(xi) SEQUENCE DESCRIPTION: SEQ ID NO:16:

GGGCCCTAGA A                                                          11

(2) INFORMATION FOR SEQ ID NO:17:

(i) SEQUENCE CHARACTERISTICS:
           (A) LENGTH:         24 base pairs
           (B) TYPE:           nucleic acid
           (C) STRANDEDNESS:   single
```

-continued

```
        (D) TOPOLOGY:      linear (ii) MOLECULE TYPE: DNA (Genomic)

(xi) SEQUENCE DESCRIPTION: SEQ ID NO:17:

AGCGGATAAC AATTTCACAC AGGA                                              24

(2) INFORMATION FOR SEQ ID NO:18:

(i) SEQUENCE CHARACTERISTICS:
         (A) LENGTH:       45 base pairs
         (B) TYPE:         nucleic acid
         (C) STRANDEDNESS: single
         (D) TOPOLOGY:     linear (ii) MOLECULE TYPE: DNA (Genomic)

(xi) SEQUENCE DESCRIPTION: SEQ ID NO:18:

TCCTATGGCA GGAAGAAGCG GAGATAGTGA TGAAGACCTC CTCAA                       45

(2) INFORMATION FOR SEQ ID NO:19:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:19:

CCCAAACAAG ACAAGAGATT GA                                                22

(2) INFORMATION FOR SEQ ID NO:20:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:20:

CCTGCGTCGA GAGAGCTCCT CTGG                                              24

(2) INFORMATION FOR SEQ ID NO:21:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:21:

GCTAACTAGG GAACCCACTG C                                                 21

(2) INFORMATION FOR SEQ ID NO:22:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:22:
```

CTGCTAGAGA TTTTTCCACA CTGAC                                                                25

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

ACACAACTGT GTTCACTAGC                                                                      20

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

CAACTTCATC CACGTTCACC                                                                      20

(2) INFORMATION FOR SEQ ID NO:25:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:25:

GGGGUUCCUC UGGUUAGACC AGAUCUGAGC CUGGGAGCUC UCUGGCUAAC UAGGGAACCC        60

ACU                                                                                        63

(2) INFORMATION FOR SEQ ID NO:26:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:26:

GGGGUUCCUC UGGUUAGACU CGCUCUGAGC CUGGGAGCUC UCUGGCUAAC UAGGGAACCC        60

ACU                                                                                        63

(2) INFORMATION FOR SEQ ID NO:27:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:27:

```
GGGGUUCCUC UGGUUAGACC AGAUCUGAGC CCAAAAGCUC UCUGGCUAAC UAGGGAACCC        60

ACU                                                                     63
```

(2) INFORMATION FOR SEQ ID NO:28:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:28:

```
GGGGUUCCUC UGGUUAGACC AGAUCUGAGC CUGGGAGCUC GCGAGCUAAC UAGGGAACCC        60

ACU                                                                     63
```

(2) INFORMATION FOR SEQ ID NO:29:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:29:

```
GGGGUUCCUC UGGUUAGACU CGCUCUGAGC CUGGGAGCUC GCGAGCUAAC UAGGGAACCC        60

ACU                                                                     63
```

(2) INFORMATION FOR SEQ ID NO:30:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:30:

```
GGGGUUCCUC UUAUAAGACC AGAUCUGAGC CUGGGAGCUC GCGAGCUAAC UAGGGAACCC        60

ACU                                                                     63
```

(2) INFORMATION FOR SEQ ID NO:31:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:31:

```
GGGGUUCCUC UGGUUAGACC AGAACUGAGC CUGGGAGCUC UCUGGCUAAC UAGGGAACCC        60

ACU                                                                     63
```

(2) INFORMATION FOR SEQ ID NO:32:

(i) SEQUENCE CHARACTERISTICS:
        (A) LENGTH: 63 base pairs
        (B) TYPE: nucleic acid
        (C) STRANDEDNESS: single
        (D) TOPOLOGY: linear -continued

```
    (ii) MOLECULE TYPE: RNA (genomic)

(xi) SEQUENCE DESCRIPTION: SEQ ID NO:32:

GGGGUUCCUC UGGUUAGACC AGAGAGCCUG GGAGCUCUCU UCUGGCUAAC UAGGGAACCC     60

ACU                                                                   63

(2) INFORMATION FOR SEQ ID NO:33:

(i) SEQUENCE CHARACTERISTICS:
          (A) LENGTH: 60 base pairs
          (B) TYPE: nucleic acid
          (C) STRANDEDNESS: single
          (D) TOPOLOGY: linear (ii) MOLECULE TYPE: RNA (genomic)

(xi) SEQUENCE DESCRIPTION: SEQ ID NO:33:

GGGGUUCCUC UGGUUAGACC AGAGAGCCUG GGAGCUCUCU GGCUAACUAG GGAACCCACU     60
```